United States Patent
Guo et al.

(10) Patent No.: US 11,555,038 B2
(45) Date of Patent: Jan. 17, 2023

(54) CRYSTALLINE FORMS OF (S)-7-(1-(BUT-2-YNOYL)PIPERIDIN-4-YL)-2-(4-PHENOXYPHENYL)-4,5,6,7-TETRAHYDROPYRAZOLO[1,5-A]PYRIMIDINE-3-CARBOXAMIDE, PREPARATION, AND USES THEREOF

(71) Applicant: BEIGENE, LTD., Grand Cayman (KY)

(72) Inventors: Yunhang Guo, Beijing (CN); Desheng Yu, Beijing (CN); Zhiwei Wang, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 534 days.

(21) Appl. No.: 16/479,709

(22) PCT Filed: Jan. 25, 2018

(86) PCT No.: PCT/CN2018/074108
§ 371 (c)(1),
(2) Date: Jul. 22, 2019

(87) PCT Pub. No.: WO2018/137681
PCT Pub. Date: Aug. 2, 2018

(65) Prior Publication Data
US 2021/0332049 A1    Oct. 28, 2021

(30) Foreign Application Priority Data
Jan. 25, 2017   (WO) ............... PCT/CN2017/072553

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................. C07D 487/04
USPC ........................................................ 544/282
See application file for complete search history.

(56) References Cited

U.S. PATENT DOCUMENTS

| | | |
|---|---|---|
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,393,848 B2 | 7/2008 | Currie et al. |
| 7,414,171 B2 | 8/2008 | Honjo et al. |
| 7,416,726 B2 | 8/2008 | Ravetch |
| 7,488,802 B2 | 2/2009 | Collins et al. |
| 7,514,444 B2 | 4/2009 | Honigberg et al. |
| 7,563,869 B2 | 7/2009 | Honjo et al. |

(Continued)

FOREIGN PATENT DOCUMENTS

| | | |
|---|---|---|
| CN | 1753912 A | 3/2006 |
| CN | 1771231 A | 5/2006 |

(Continued)

OTHER PUBLICATIONS

Extended European Search Report for European Application No. 14787642.9, dated Jan. 26, 2016, 5 pages.

(Continued)

*Primary Examiner* — Douglas M Willis
(74) *Attorney, Agent, or Firm* — Cooley LLP

(57) ABSTRACT

The present invention relates to a crystalline form of (S)-7-(1-(but-2-ynoyl)piperidin-4-yl)-2-(4-phenoxyphenyl)-4,5,6,7-tetrahydropyrazolo[1,5-a]pyrimidine-3-carboxamide (Compound 1) for inhibiting Btk, methods of preparation thereof and pharmaceutical compositions, and use of the crystalline form above in the treatment of a disease, or in the manufacturing of a medicament for the treatment of a disease, such as an allergic disease, an autoimmune disease, an inflammatory disease, and a cancer.

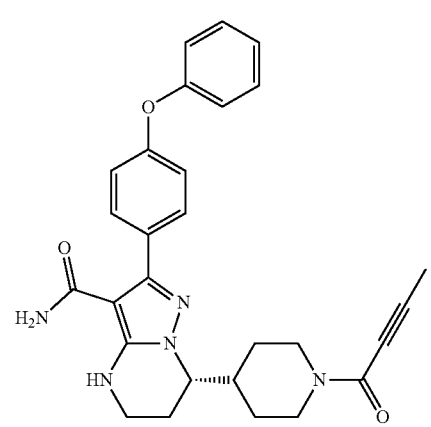

Compound 1

7 Claims, 27 Drawing Sheets

(56) References Cited

U.S. PATENT DOCUMENTS

| | | |
|---|---|---|
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,718,662 B1 | 5/2010 | Chen et al. |
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,084,620 B2 | 12/2011 | Liu et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,246,955 B2 | 8/2012 | Honjo et al. |
| 8,354,509 B2 | 1/2013 | Carven et al. |
| 8,552,154 B2 | 10/2013 | Freeman et al. |
| 8,617,546 B2 | 12/2013 | Kang et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,911,726 B2 | 12/2014 | Takahashi et al. |
| 8,945,561 B2 | 2/2015 | Davis |
| 9,067,999 B1 | 6/2015 | Honjo et al. |
| 9,073,994 B2 | 7/2015 | Honjo et al. |
| 9,084,776 B2 | 7/2015 | Korman et al. |
| 9,139,653 B1 | 9/2015 | Campbell et al. |
| 9,175,082 B2 | 11/2015 | Zhou et al. |
| 9,217,034 B2 | 12/2015 | Li et al. |
| 9,447,106 B2 | 9/2016 | Wang et al. |
| 9,492,540 B2 | 11/2016 | Korman et al. |
| 9,556,188 B2 | 1/2017 | Wang et al. |
| 9,624,298 B2 | 4/2017 | Nastri et al. |
| 9,834,606 B2 | 12/2017 | Li et al. |
| 9,920,123 B2 | 3/2018 | Irving et al. |
| 9,988,450 B2 | 6/2018 | Li et al. |
| 10,005,782 B2 | 6/2018 | Wang et al. |
| 10,058,609 B2 | 8/2018 | Zhou et al. |
| 10,487,147 B2 | 11/2019 | Nastri et al. |
| 10,519,235 B2 | 12/2019 | Li et al. |
| 10,544,225 B2 | 1/2020 | Li et al. |
| 10,550,185 B2 | 2/2020 | Bernett et al. |
| 10,570,139 B2 | 2/2020 | Wang et al. |
| 10,793,632 B2 | 10/2020 | Bernett et al. |
| 10,858,435 B2 | 12/2020 | Finlay |
| 10,864,203 B2 | 12/2020 | Song et al. |
| 10,927,117 B2 | 2/2021 | Wang et al. |
| 2002/0094989 A1 | 7/2002 | Hale et al. |
| 2004/0038339 A1 | 2/2004 | Kufer et al. |
| 2005/0064514 A1 | 3/2005 | Stavenhagen et al. |
| 2005/0202028 A1 | 9/2005 | Ledbetter et al. |
| 2006/0121032 A1 | 6/2006 | Dahiyat et al. |
| 2006/0134105 A1 | 6/2006 | Lazar et al. |
| 2006/0178367 A1 | 8/2006 | Currie et al. |
| 2006/0183746 A1 | 8/2006 | Currie et al. |
| 2006/0263856 A1 | 11/2006 | Gillies et al. |
| 2007/0160597 A1 | 7/2007 | Lazar et al. |
| 2008/0076921 A1 | 3/2008 | Honigberg et al. |
| 2008/0139582 A1 | 6/2008 | Honigberg et al. |
| 2009/0068175 A1 | 3/2009 | Lazar et al. |
| 2009/0105209 A1 | 4/2009 | Dewdney et al. |
| 2009/0155256 A1 | 6/2009 | Black et al. |
| 2009/0217401 A1 | 8/2009 | Korman et al. |
| 2009/0318441 A1 | 12/2009 | Brain et al. |
| 2010/0004231 A1 | 1/2010 | Dewdney et al. |
| 2010/0016296 A1 | 1/2010 | Singh et al. |
| 2010/0016301 A1 | 1/2010 | Dewdney et al. |
| 2010/0029610 A1 | 2/2010 | Singh et al. |
| 2010/0035841 A1 | 2/2010 | Jankowski et al. |
| 2010/0087464 A1 | 4/2010 | Mi et al. |
| 2010/0105676 A1 | 4/2010 | Liu et al. |
| 2010/0144705 A1 | 6/2010 | Miller |
| 2010/0151492 A1 | 6/2010 | Ahmed et al. |
| 2010/0160292 A1 | 6/2010 | Whitney et al. |
| 2010/0160303 A1 | 6/2010 | Liu et al. |
| 2010/0197924 A1 | 8/2010 | Gould et al. |
| 2010/0222325 A1 | 9/2010 | Berthel et al. |
| 2010/0249092 A1 | 9/2010 | Singh et al. |
| 2010/0254905 A1 | 10/2010 | Honigberg et al. |
| 2010/0317834 A1 | 12/2010 | Lazar et al. |
| 2011/0008369 A1 | 1/2011 | Finnefrock et al. |
| 2011/0052584 A1 | 3/2011 | Ravetch |
| 2011/0054151 A1 | 3/2011 | Lazar et al. |
| 2011/0118233 A1 | 5/2011 | Blomgren et al. |
| 2011/0124640 A1 | 5/2011 | Liu et al. |
| 2011/0159023 A1 | 6/2011 | Langermann |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0224235 A1 | 9/2011 | Honigberg et al. |
| 2011/0271358 A1 | 11/2011 | Freeman et al. |
| 2011/0287032 A1 | 11/2011 | Lazar et al. |
| 2011/0301145 A1 | 12/2011 | Barbosa, Jr. et al. |
| 2012/0028981 A1 | 2/2012 | Miller |
| 2012/0040961 A1 | 2/2012 | Gray et al. |
| 2012/0053189 A1 | 3/2012 | Loury |
| 2012/0058996 A1 | 3/2012 | Liu et al. |
| 2012/0076726 A1 | 3/2012 | Gellerfors et al. |
| 2012/0077832 A1 | 3/2012 | Witowski et al. |
| 2012/0082702 A1 | 4/2012 | DeLucca et al. |
| 2012/0129852 A1 | 5/2012 | Duan et al. |
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2012/0237522 A1 | 9/2012 | Kang et al. |
| 2012/0251531 A1 | 10/2012 | Baehner et al. |
| 2013/0004514 A1 | 1/2013 | Zahn et al. |
| 2013/0079327 A1 | 3/2013 | Yamamoto et al. |
| 2013/0089541 A1 | 4/2013 | D'Angelo et al. |
| 2013/0096118 A1 | 4/2013 | Liu et al. |
| 2013/0116213 A1 | 5/2013 | Cha et al. |
| 2013/0259868 A1 | 10/2013 | Roschke et al. |
| 2013/0261103 A1 | 10/2013 | Currie et al. |
| 2013/0281432 A1 | 10/2013 | Currie et al. |
| 2013/0309250 A1 | 11/2013 | Cogswell et al. |
| 2014/0044738 A1 | 2/2014 | Langermann et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162316 A1 | 6/2014 | O'Neil et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2014/0243504 A1 | 8/2014 | Davis et al. |
| 2014/0245468 A1 | 8/2014 | McWhirter et al. |
| 2014/0271642 A1 | 9/2014 | Murphy et al. |
| 2014/0314714 A1 | 10/2014 | Honjo et al. |
| 2014/0341902 A1 | 11/2014 | Maecker et al. |
| 2014/0356363 A1 | 12/2014 | Zhou et al. |
| 2014/0377269 A1 | 12/2014 | Mabry et al. |
| 2015/0044231 A1 | 2/2015 | Kjaergaard et al. |
| 2015/0079109 A1 | 3/2015 | Li et al. |
| 2015/0125444 A1 | 5/2015 | Tsui et al. |
| 2015/0210763 A1 | 7/2015 | Kuramochi et al. |
| 2015/0259354 A1 | 9/2015 | Wang et al. |
| 2015/0315274 A1 | 11/2015 | Li et al. |
| 2015/0337053 A1 | 11/2015 | McCarthy et al. |
| 2015/0353631 A1 | 12/2015 | Buttini et al. |
| 2016/0083392 A1 | 3/2016 | Wang et al. |
| 2017/0044260 A1 | 2/2017 | Baruah et al. |
| 2017/0073349 A1 | 3/2017 | Wang et al. |
| 2018/0037655 A1 | 2/2018 | Hegde et al. |
| 2018/0215825 A1 | 8/2018 | Li et al. |
| 2018/0251466 A1 | 9/2018 | Wang et al. |
| 2018/0251551 A1 | 9/2018 | Li et al. |
| 2019/0169201 A1 | 6/2019 | Wang et al. |
| 2020/0030339 A1 | 1/2020 | Wang et al. |

(56) References Cited

U.S. PATENT DOCUMENTS

| | | |
|---|---|---|
| 2020/0069666 A1 | 3/2020 | Song et al. |
| 2020/0148690 A1 | 5/2020 | Wang et al. |
| 2020/0181150 A1 | 6/2020 | Wang et al. |
| 2020/0216535 A1 | 7/2020 | Li et al. |
| 2020/0283527 A1 | 9/2020 | Li et al. |
| 2020/0368237 A1 | 11/2020 | Hilger et al. |
| 2021/0040213 A1 | 2/2021 | Song et al. |
| 2021/0130363 A1 | 5/2021 | Wang et al. |
| 2021/0147543 A1 | 5/2021 | Wang et al. |
| 2021/0228553 A1 | 7/2021 | Song et al. |
| 2021/0230274 A1 | 7/2021 | Li et al. |
| 2021/0275530 A1 | 9/2021 | Hu et al. |

FOREIGN PATENT DOCUMENTS

| | | |
|---|---|---|
| CN | 101104640 A | 1/2008 |
| CN | 101213297 A | 7/2008 |
| CN | 101355965 A | 1/2009 |
| CN | 101899114 A | 12/2010 |
| CN | 102245640 A | 11/2011 |
| CN | 102264762 A | 11/2011 |
| CN | 102656173 A | 9/2012 |
| CN | 104884458 A | 9/2015 |
| CN | 105531288 A | 4/2016 |
| CN | 106103485 A | 11/2016 |
| CN | 107011441 A | 8/2017 |
| CN | 107090041 A | 8/2017 |
| GB | 1412017 | 10/1975 |
| JP | H 07-278148 A | 10/1995 |
| JP | 2006510582 A | 3/2006 |
| JP | 2008544755 A | 12/2008 |
| JP | 2009155338 A | 7/2009 |
| JP | 2010504324 A | 2/2010 |
| JP | 2010528993 A | 8/2010 |
| JP | 2012511329 A | 5/2012 |
| JP | 2012254092 A | 12/2012 |
| KR | 20080011428 A | 2/2008 |
| KR | 20100054780 A | 5/2010 |
| WO | WO-9429351 A2 | 12/1994 |
| WO | WO 2001/016138 A1 | 3/2001 |
| WO | WO 2001/019829 A2 | 3/2001 |
| WO | WO 2002/050071 A1 | 6/2002 |
| WO | WO 2002/072576 A1 | 9/2002 |
| WO | WO 2003/004497 A1 | 1/2003 |
| WO | WO 2004/017908 A2 | 3/2004 |
| WO | WO 2005/005429 A1 | 1/2005 |
| WO | WO 2005/011597 A2 | 2/2005 |
| WO | WO 2005/014599 A1 | 2/2005 |
| WO | WO 2005/047290 A2 | 5/2005 |
| WO | WO-2005077981 A2 | 8/2005 |
| WO | WO 2006/053121 A2 | 5/2006 |
| WO | WO 2006/065946 A1 | 6/2006 |
| WO | WO-2006084015 A2 | 8/2006 |
| WO | WO 2006/099075 A2 | 9/2006 |
| WO | WO-2006121168 A1 | 11/2006 |
| WO | WO-2006133396 A2 | 12/2006 |
| WO | WO-2007005874 A2 | 1/2007 |
| WO | WO 2007/026720 A1 | 3/2007 |
| WO | WO 2007/026950 A1 | 3/2007 |
| WO | WO 2007/027594 A1 | 3/2007 |
| WO | WO 2007/027729 A1 | 3/2007 |
| WO | WO-2007067444 A1 | 6/2007 |
| WO | WO 2007/087068 A2 | 8/2007 |
| WO | WO 2007/136790 A2 | 11/2007 |
| WO | WO-2007136572 A2 | 11/2007 |
| WO | WO 2008/033834 A1 | 3/2008 |
| WO | WO 2008/033854 A1 | 3/2008 |
| WO | WO 2008/033857 A2 | 3/2008 |
| WO | WO 2008/039218 A2 | 4/2008 |
| WO | WO 2008/054827 A2 | 5/2008 |
| WO | WO 2008/144253 A1 | 11/2008 |
| WO | WO-2008145142 A1 | 12/2008 |
| WO | WO-2008156712 A1 | 12/2008 |
| WO | WO 2009/039397 A2 | 3/2009 |
| WO | WO 2009/051822 A1 | 4/2009 |
| WO | WO 2009/077334 A1 | 6/2009 |
| WO | WO 2009/098144 A1 | 8/2009 |
| WO | WO 2009/158571 A1 | 12/2009 |
| WO | WO 2010/000633 A1 | 1/2010 |
| WO | WO 2010/006947 A1 | 1/2010 |
| WO | WO 2010/006970 A1 | 1/2010 |
| WO | WO 2010/028236 A1 | 3/2010 |
| WO | WO 2010/051549 A1 | 5/2010 |
| WO | WO 2010/065898 A2 | 6/2010 |
| WO | WO 2010/068788 A1 | 6/2010 |
| WO | WO 2010/068806 A1 | 6/2010 |
| WO | WO 2010/068810 A2 | 6/2010 |
| WO | WO-2010077634 A1 | 7/2010 |
| WO | WO-2010089411 A2 | 8/2010 |
| WO | WO 2010/122038 A1 | 10/2010 |
| WO | WO 2011/006074 A1 | 1/2011 |
| WO | WO 2011/140488 A1 | 11/2011 |
| WO | WO 2011/153514 A2 | 12/2011 |
| WO | WO 2012/020008 A1 | 2/2012 |
| WO | WO-2012083370 A1 | 6/2012 |
| WO | WO 2012/135801 A1 | 10/2012 |
| WO | WO 2012/143522 A1 | 10/2012 |
| WO | WO-2012130831 A1 | 10/2012 |
| WO | WO-2012135408 A1 | 10/2012 |
| WO | WO-2012145493 A1 | 10/2012 |
| WO | WO 2012/156334 A1 | 11/2012 |
| WO | WO 2012/158795 A1 | 11/2012 |
| WO | WO-2012175692 A1 | 12/2012 |
| WO | WO-2013079174 A1 | 6/2013 |
| WO | WO-2013173223 A1 | 11/2013 |
| WO | WO-2013181634 A2 | 12/2013 |
| WO | WO-2014055897 A2 | 4/2014 |
| WO | WO-2014100079 A1 | 6/2014 |
| WO | WO 2014/173289 A1 | 10/2014 |
| WO | WO 2015/035606 | 3/2015 |
| WO | WO 2015/061752 A1 | 4/2015 |
| WO | WO-2015112900 A1 | 7/2015 |
| WO | WO-2016000619 A1 | 1/2016 |
| WO | WO-2016008411 A1 | 1/2016 |
| WO | WO 2016/025720 | 2/2016 |
| WO | WO-2016024228 A1 | 2/2016 |
| WO | WO-2016064649 A1 | 4/2016 |
| WO | WO 2016/087994 A1 | 6/2016 |
| WO | WO 2016/100914 A1 | 6/2016 |
| WO | WO 2016/105582 A1 | 6/2016 |
| WO | WO-2017025016 A1 | 2/2017 |
| WO | WO 2017/046746 A1 | 3/2017 |
| WO | WO 2017/059224 A2 | 4/2017 |
| WO | WO 2018/033135 | 2/2018 |
| WO | WO 2018/033853 | 2/2018 |
| WO | WO 2018/137681 | 8/2018 |
| WO | WO 2018/193105 A1 | 10/2018 |
| WO | WO-2019001417 A1 | 1/2019 |
| WO | WO 2019/034009 | 2/2019 |
| WO | WO 2019/108795 | 6/2019 |
| WO | WO-2019157353 A1 | 8/2019 |

OTHER PUBLICATIONS

International Search Report and Written Opinion for International Application No. PCT/CN2014/075943, dated Jul. 18, 2014, 10 pages.
Extended European Search Report for European Application No. 17841172.4, dated Mar. 5, 2020, 6 pages.
International Search Report and Written Opinion for International Application No. PCT/IB2017/054955, dated Sep. 10, 2018, 16 pages.
Extended European Search Report for European Application No. 17841107.0, dated Feb. 21, 2020, 12 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/100145, dated Nov. 14, 2018, 8 pages.

(56) References Cited

OTHER PUBLICATIONS

International Search Report and Written Opinion for International Application No. PCT/US2018/063068, dated Feb. 27, 2019, 8 pages.
Bradshaw, J. M., "The Src, Syk, and Tec family kinases: Distinct types of molecular switches," Cell. Signalling, 22:1175-1184 (2010).
Caira, E. D. et al., "Crystalline polymorphism of organic compounds," Topics in Current Chemistry, vol. 198, 1998, pp. 163-208.
Conley, M. E. et al., "Primary B Cell Immunodeficiencies: Comparisons and Contrasts," Annu. Rev. Immunol., 27:199-227 (2009).
Davis, R. E. et al., "Chronic active B-cell-receptor signalling in diffuse large B-cell lymphoma," Nature, 463:88-92 (2010).
Gurcan, H. M. et al., "A review of the current use of rituximab in autoimmune diseases," Int. Immunopharmacol., 9:10-25 (2009).
Hackam, D. G. et al., "Translation of research evidence from animals to humans," JAMA, 296(14):1731-1732 (2006).
Humphries, L. A. et al., "Tec Kinases Mediate Sustained Calcium Influx via Site-specific Tyrosine Phosphorylation of the Phospholipase Cγ Src Homology 2-Src Homology 3 Linker," J. Biol.Chem. 279(36):37651-37661 (2004).
Jenkins, S. M. et al., "Substituent variation in azabicyclic triazole- and tetrazole-based muscarinic receptor ligands," J. Med. Chem., 35(13):2392-2406 (1992).
Jordan, V. C., "Tamoxifen: A most unlikely pioneering medicine," Nature Reviews: Drug Discovery, 2:205-213 (2003).
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Luo, J. et al., "Modern Physical Pharmaceutics Theory and Practice," Shang Hai Science and Technology Literature Publishing House, Apr. 2005, pp. 293-295.
Mohamed, A. J. et al., "Bruton's tyrosine kinase (Btk): function, regulation, and transformation with special emphasis on the PH domain," Immunol. Rev., 228:58-73 (2009).
Pan, Z, "Bruton's tyrosine kinase as a drug discovery target," Drug News Perspect, 21(7):357-362 (2008).
Rokosz, L. L. et al., "Kinase inhibitors as drugs for chronic inflammatory and immunological diseases: progress and challenges," Expert Opin. Ther. Targets, 12(7):883-903 (2008).
Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Uckun, F. M. et al., "Bruton's tyrosine kinase as a new therapeutic target," Anti-Cancer Agents in Medicinal Chemistry, 7(6):624-632 (2007).
Vetrie, D. et al., "The gene involved in X-linked agammaglobulinaemia is a member of the src family of protein-tyrosine kinases," Nature, 361:226-233 (1993).
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).

Abdiche et al., "Assessing kinetic and epitopic diversity across orthogonal monoclonal antibody generation platforms." mAbs (Feb.-Mar. 2016); 8(2):264-277.
Ahmadzadeh, M. et al., "Tumor antigen-specific CD8 T cells infiltrating the tumor express high levels of PD-1 and are functionally impaired," Blood. Aug. 20, 2009;114(8):1537-1544. doi: 10.1182/blood-2008-12-195792. Epub May 7, 2009.
Araki, K. et al., "Programmed cell death 1-directed immunotherapy for enhancing T-cell function," Cold Spring Harbor Symposia on Quantitative Biology, vol. LXXVIII, 239-247 (2013).
Arlauckas, S.P. et al., "In vivo imaging reveals a tumor-associated macrophage-mediated resistance pathway in anti-PD-1 therapy," Sci. Transl. Med., 9, eaal3604 (May 2017).
Balar, A. et al., "Pembrolizumab (pembro) as first-line therapy for advanced/unresectable or metastatic urothelial cancer: Preliminary results from the phase 2 KEYNOTE-052 study," Annals of Oncology 27 (Supplement 6): vi552-vi587, 2016.
Balbach, S. et al., "Pharmaceutical evaluation of early development candidates 'the 100 mg-approach,'" International Journal of Pharmaceutics, 275 (2004), pp. 1-12.
Bellmunt, J. et al., "Keynote-045: open-label, phase II study of pembrolizumab versus investigator's choice of paclitaxel, docetaxel, or vinflunine for previously treated advanced urothelial cancer," Journal for ImmunoTherapy of Cancer, 2016, 4(Suppl. 2):91, Presented at 31st Society for Immunotherapy of Cancer Annual Meeting, Nov. 9-13, 2016, National Harbor, MD, 1 page.
Bellmunt, J. et al., "Pembrolizumab as Second-Line Therapy for Advanced Urothelial Carcinoma," N. Engl. J. Med., vol. 376, No. 11, Mar. 2017, pp. 1015-1026.
Bellmunt, J. et al., "Randomized Phase III Study Comparing Paclitaxel/Cisplatin/Gemcitabine and Gemcitabine/Cisplatin in Patients with Locally Advanced or Metastatic Urothelial Cancer Without Prior Systemic Therapy: EORTC Intergroup Study 30987," J Clin Oncol., Apr. 1, 2012;30(10):1107-1113.
Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).
Boyd et al., "Deep sequencing and human antibody repertoire analysis." Current Opinion in Immunology (Jun. 2016); 40: 103-109. Epub Apr. 8, 2016.
Brahmer, J. R. et al., "Safety and Activity of Anti-PD-L1 Antibody in Patients with Advanced Cancer," N Engl J Med. (Jun. 28, 2012), 366(26):2455-2465.
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Brand, F-X et al., "Prospect for anti-HER2 receptor therapy in breast cancer," Anticancer Research, 26:463-470 (2006).
Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.
Casset, F. et al., "A peptide mimetic of an anti-CD4 monoclonal antibody by rational design," Biochemical and Biophysical Research Communications, 307:198-205 (2003).
Yen, C-J et al., "Preliminary results of a phase 1A/1B study of BGB-A317, an anti-PD-1 monoclonal antibody (mAb), in patients with advanced hepatocellular carcinoma (HCC)," Abstract P-140, Annals of Oncology, vol. 28, Supplement 3, p. 54 (2017).
Clynes, R. A. et al., "Inhibitory Fc receptors modulate in vivo cytoxicity against tumor targets," Nat. Med. 6(4):443-446 (Apr. 2000).
Conroy, et al., "Antibodies: From novel repertoires to defining and refining the structure of biologically important targets," Methods (Mar. 2017); 116:12-22. Epub Jan. 11, 2017.
Dahan, R. et al., "FcRs Modulate the Anti-tumor Activity of Antibodies Targeting the PD-1/PD-L1 Axis," Cancer Cell (Sep. 2015), 28(3):285-95. doi: 10.1016/j.ccell.2015.08.004.
Damschroder et al., "Analysis of human and primate CD2 molecules by protein sequence and epitope mapping with anti-human CD2 antibodies," Mol Immunol. (Aug. 2004), 41(10):985-1000.

(56) References Cited

OTHER PUBLICATIONS

De Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).

De Toni, E. N. et al., "Tapering of Immunosuppression and Sustained Treatment With Nivolumab in a Liver Transplant Recipient," Gastroenterology, May 2017;152(6):1631-1633. doi: 10.1053/j.gastro.2017.01.063.

Desai, J. et al., "Updated safety, efficacy, and pharmacokinetics (PK) results from thephase I study of BGB-A317, an anti-programmed death-1 (PD-1) mAb in patients with advanced solid tumors," J. Immunother. Cancer, 2016; 4(Suppl 1):P154, 2 pages.

Dorfman, D. M. et al., "Programmed death-1 (PD-1) is a marker of germinal center-associated T Cells and angioimmunoblastic T-cell lymphoma," American Journal of Surgical Pathology, 30(7):802-810 (Jul. 2006).

El-Khoueiry, A. B. et al., "Nivolumab in patients with advanced hepatocellular carcinoma (CheckMate 040): an open-label, non-comparative, phase 1/2 dose escalation and expansion trial," Lancet, Jun. 24, 2017;389(10088):2492-2502. doi: 10.1016/S0140-6736(17)31046-2.

European Search Report for European Application No. 16167542.6, dated Nov. 14, 2016, 5 pages.

Extended European Search Report for European Application No. 15815646.3, dated Dec. 21, 2017, 10 pages.

Extended European Search Report for European Application No. 18823691.3, dated Feb. 22, 2021, 9 pages.

Ferrara et al., "Recombinant renewable polyclonal antibodies." mABs (2015); 7(1):32-41.

Fuller, M. J. et al., "Immunotherapy of chronic hepatitis C virus infection with antibodies against programmed cell death-1 (PD-1)," Proceedings of the National Academy of Sciences, 110(37):15001-15006 (Sep. 2013).

Galsky, M. D. et al., "Effectiveness of Adjuvant Chemotherapy for Locally Advanced Bladder Cancer," J Clin Oncol. Mar. 10, 2016;34(8):825-832.

Gelderman, K. A. et al., "Complement function in mAb-mediated cancer immunotherapy," Trends in Immunology, 25(3):158-164 (Mar. 2004).

Hamid, O. et al., "Safety and tumor responses with lambrolizumab (Anti-PD-1) in melanoma," New England Journal of Medicine, 369(2):134-144 (Jul. 2013).

Hirayama, Y., "Handbook for organic compound crystal—Principle and know-how," 2008, 28 pages.

"History of Changes for Study: NCT02690558. Phase 2 Study of Pembrolizumab in Combination With Gemcitabine and Cisplatin as Neoadjuvant Therapy," NCT02690558, Mar. 10, Mar. 2017, Retrieved from the Internet: URL:https://clinicaltrials.gov/ct2/history/NCT02690558?V_4=View#StudyPageTop, 5 pages.

International Search Report and Written Opinion for International Application No. PCT/CN2013/083467, dated Jun. 16, 2014, 9 pages.

International Search Report and Written Opinion for International Application No. PCT/CN2015/083066, dated Sep. 24, 2015, 8 pages.

International Search Report and Written Opinion for International Application No. PCT/CN2018/092827, dated Sep. 29, 2018, 14 pages.

International Search Report for International Application No. PCT/US2019/017313, dated Jun. 25, 2019, 16 pages.

InvivoGen Insight, "IgG-Fc Engineering for Therapeutic Use," Apr./May 2006, 4 pages.

James, L. K. et al., "Potential Mechanisms for IgG4 Inhibition of Immediate Hypersensitivity Reactions," Curr Allergy Asthma Rep. 2016; 16: 23. Published online Feb. 18, 2016. doi: 10.1007/s11882-016-0600-2.

Jiao, Y. et al., "Advances in the research of the anti-cancer agent—Raf kinase inhibitor," Strait Pharmaceutical Journal, vol. 19, No. 8, 2007, pp. 1-5 (with English Abstract).

Jie, L., "Deuterated Drugs Progress," Chemical Engineering Design Communication Medicine and Chemical Industry, 2016, vol. 42 (4), pp. 199.

Khan et al., "Cross-neutralizing anti-HIV-1 human single chain variable fragments (scFvs) against CD4 binding site and N332 glycan identified from a recombinant phage library." Scientific Reports (2017); Article No. 45163, 12 pages.

Konitzer et al., "Generation of a highly diverse panel of antagonistic chicken monoclonal antibodies against the GIP receptor," mABs (Apr. 2017); 9(3):536-549. Epub Jan. 5, 2017.

Kudo, M., Immune Checkpoint Blockade in Hepatocellular Carcinoma: 2017 Update, Liver Cancer, Nov. 2016; 6(1):1-12.

Kudo, M., "Immune Checkpoint Inhibition in Hepatocellular Carcinoma: Basics and Ongoing Clinical Trials," Oncology, 2017;92 Suppl 1:50-62. doi: 10.1159/000451016. Epub Feb. 2, 2017.

Lee et al., "Molecular-level analysis of the serum antibody repertoire in young adults before and after seasonal influenza vaccination." Nat Med. (Dec. 2016); 22(12):1456-1464. Epub Nov. 7, 2016.

Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.

Lund, J. et al., "Multiple interactions of IgG with its core oligosaccharide can modulate recognition by complement and human Fc gamma receptor I and influence the synthesis of its oligosaccharide chains," J Immunol., Dec. 1, 1996, 157(11):4963-4969.

MedChemExpress, "Zanubrutinib," Product Data Sheet, Retrieved from the Internet: www.medchemexpress.com, Retrieved Aug. 17, 2021, 2 pages.

Panka, D. J. et al., "Variable region framework differences result in decreased or increased affinity of variant anti-digoxin antibodies," May 1988, Proc. Natl. Acad. Sci. USA, 85:3080-3084.

Parola et al., "Integrating high-throughput screening and sequencing for monoclonal antibody discovery and engineering." Immunology (Jan. 2018); 153(1):31-41. Epub Oct. 30, 2017.

Paul, W. E. (Ed.), Chap. 9, Structure and Function of Immunoglobulins, In: Fundamental Immunology, Third Edition, pp. 292-295, 1993.

Plimack, E. R. et al., "Pembrolizumab (MK-3475) for advanced urothelial cancer: Updated results and biomarker analysis from KEYNOTE-012," J. Clin. Oncol., vol. 33, Issue 15 Suppl., May 2015, Abstract 4502, 2 pages.

Presta, L. G. et al., "Engineering therapeutic antibodies for improved function," Biochemical Society Transactions (2002) vol. 30, Part 4, pp. 487-490.

Rudikoff, S. et al., "Single amino acid substitution altering antigen-binding specificity," Proc. Natl. Acad. Sci. USA, 79:1979-1983 (Mar. 1982).

Samonakis, D. N. et al., "Systemic treatment for hepatocellular carcinoma: Still unmet expectations," World J Hepatol., Jan. 2017; 9(2):80-90.

Sequence Alignment, 2014, 1 page.

Sharma, P. et al., "Efficacy and safety of nivolumab monotherapy in metastatic urothelial cancer (mUC): Results from the phase I/II CheckMate 032 study," J. Clin. Oncol., vol. 34, No. 15 Suppl., May 2016, pp. 4501.

Sharma, P. et al., "Nivolumab monotherapy in recurrent metastatic urothelial carcinoma (CheckMate 032): a multicentre, open-label, two-stage, multi-arm, phase 1/2 trial," Lancet Oncol., Nov. 2016, vol. 17, No. 11, pp. 1590-1598.

Sheehan et al., "Phage and Yeast Display." Microbial. Spectr. (2015); 3(1):AID-0028-2014; 17 pages.

Shields, R. L. et al., "High Resolution Mapping of the Binding Site on Human IgG1 for FcRI, FcRII, FcRIII, and FcRn and Design of IgG1 Variants with Improved Binding to the FcR," The Journal of Biological Chemistry, 276(9):6591-6604 (2001).

Shioji, Y., "Production Technology of Solid Preparations," Tokyo, CMC Publication, Jan. 27, 2003, Popular Edition, pp. 9 and 12-13.

(56) References Cited

OTHER PUBLICATIONS

Singhal, D. et al., "Drug polymorphism and dosage form design: a practical perspective," Advanced Drug Delivery Reviews, 56 (2004) pp. 335-347.

Smith, K. G. et al., "FcRIIB in autoimmunity and infection: evolutionary and therapeutic implications," Nat Rev Immunol. May 2010;10(5):328-43.

Stave, J. W. et al., "Antibody and antigen contact residues define epitope and paratope size and structure," The Journal of Immunology, vol. 191, Jan. 2013, pp. 1428-1435.

Strome, S. E. et al., "A Mechanistic Perspective of Monoclonal Antibodies in Cancer Therapy Beyond Target-Related Effects," The Oncologist, 2007; 12:1084-1095.

Supplementary Partial European Search Report for European Application No. 13893636.4, dated Feb. 28, 2017, 13 pages.

Sznol, M. et al., "Antagonist antibodies to PD-1 and B7-H1 (PD-L1) in the treatment of advanced human cancer," Clinical Cancer Research, 19(5):1021-1034 (Mar. 2013).

Takada, N., "Bulk Drug Form Screening and Selection at Drug Discovery Phase," Pharm Stage, Jan. 15, 2007 vol. 6, No. 10, pp. 20-25.

Topalian, S. L., "Safety, Activity, and Immune Correlates of Anti-PD-1 Antibody in Cancer," N. Engl. J. Med., Jun. 2012; vol. 366, No. 26, pp. 2443-2454.

Van Regenmortel, M. H. V., "Development of a Preventive HIV Vaccine Requires Solving Inverse Problems Which Is Unattainable by Rational Vaccine Design." Front Immunol. (Jan. 2018); 8: 2009. eCollection 2017.

Wang, C. et al., "In Vitro Characterization of the Anti-PD-1 Antibody Nivolumab, BMS-936558, and In Vivo Toxicology in Non-Human Primates," Cancer Immunol Res; 2(9):846-856 (Sep. 2014).

Wherry, E. J., "T cell exhaustion," Nature Immunology 12(6):492-499 (2011). Published online May 18, 2011.

Wu, H. et al., "Humanization of a murine monoclonal antibody by simultaneous optimization of framework and CDR residues," Journal of Molecular Biology, 294(1):151-162 (Nov. 1999).

Xu, D. et al., "In vitro characterization of five humanized OKT3 effector function variant antibodies," Cell Immunol. Feb. 25, 2000;200(1):16-26.

Zhou et al., "Structural Repertoire of HIV-1-Neutralizing Antibodies Targeting the CD4 Supersite in 14 Donors." Cell (Jun. 2015); 161(6):1280-1292.

Extended European Search Report for European Application No. 18744173.8, dated Oct. 21, 2020, 12 pages.

Kersseboom, R. et al., "Constitutive activation of Bruton's tyrosine kinase induces the formation of autoreactive IgM plasma cells," Eur. J. Immunol. 40:2643-2654, 2010.

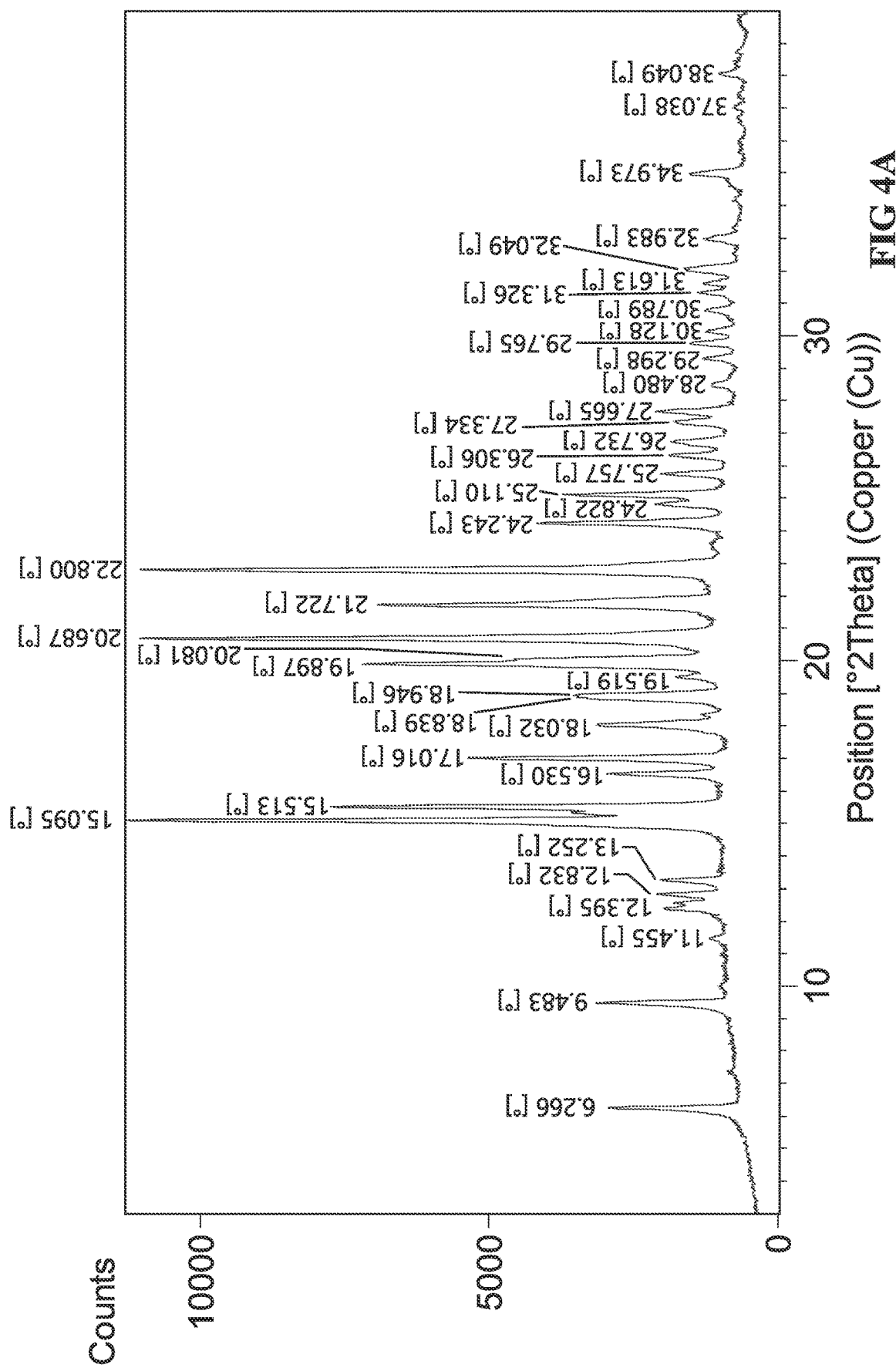

CRYSTALLINE FORMS OF (S)-7-(1-(BUT-2-YNOYL)PIPERIDIN-4-YL)-2-(4-PHENOXYPHENYL)-4,5,6,7-TETRAHYDROPYRAZOLO[1,5-A]PYRIMIDINE-3-CARBOXAMIDE, PREPARATION, AND USES THEREOF

CROSS-REFERENCE TO RELATED APPLICATIONS

This application is a U.S. National Stage Application under 35 U.S.C. § 371 of International Application No. PCT/CN2018/074108, filed Jan. 25, 2018, which claims the benefit of International Patent Application No. PCT/CN2017/072553 filed Jan. 25, 2017, the disclosures of which are hereby incorporated by reference in their entireties for all purposes.

FIELD OF THE INVENTION

Disclosed herein are crystalline forms of (S)-7-(1-(but-2-ynoyl)piperidin-4-yl)-2-(4-phenoxyphenyl)-4,5,6,7-tetrahydropyrazolo[1,5-a]pyrimidine-3-carboxamide (hereinafter Compound 1); methods for preparing crystalline forms of Compound 1; pharmaceutical compositions comprising crystalline forms of Compound 1 and a pharmaceutically acceptable carrier; and methods of using crystalline forms of Compound 1 as a Btk inhibitor for treating or preventing diseases.

BACKGROUND OF THE INVENTION

Bruton's tyrosine kinase (Btk) belongs to the Tec tyrosine kinase family (Vetrie et al., Nature 361: 226-233, 1993; Bradshaw, Cell Signal. 22: 1175-84, 2010). Btk is primarily expressed in most hematopoietic cells such as B cells, mast cells and macrophages (Smith et al., J. Immunol. 152: 557-565, 1994) and is localized in bone marrow, spleen and lymph node tissue. Btk plays important roles in B-cell receptor (BCR) and FcR signaling pathways, which involve in B-cell development, differentiation (Khan, Immunol. Res. 23: 147, 2001). Btk is activated by upstream Src-family kinases. Once activated, Btk in turn phosphorylates PLC gamma, leading to effects on B-cell function and survival (Humphries et al., J Biol. Chem. 279: 37651, 2004).

These signaling pathways must be precisely regulated. Mutations in the gene encoding Btk cause an inherited B-cell specific immunodeficiency disease in humans, known as X-linked a gamma-globulinemia (XLA) (Conley et al., Annu. Rev. Immunol. 27: 199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., Int. Immunopharmacol. 9: 10-25, 2009). Therefore, Btk inhibitors can be used to treat autoimmune and/or inflammatory diseases.

In addition, aberrant activation of Btk plays an important role in pathogenesis of B-cell lymphomas indicating that inhibition of Btk is useful in the treatment of hematological malignancies (Davis et al., Nature 463: 88-92, 2010). Preliminary clinical trial results showed that the Btk inhibitor PCI-32765 was effective in treatment of several types of B-cell lymphoma (for example, 54th American Society of Hematology (ASH) annual meeting abstract, December 2012: 686 The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multi-center, Open-Label, Phase! Study). Because Btk plays a central role as a mediator in multiple signal transduction pathways, inhibitors of Btk are of great interest as anti-inflammatory and/or anti-cancer agents (Mohamed et al., Immunol. Rev. 228: 58-73, 2009; Pan, Drug News perspect 21: 357-362, 2008; Rokosz et al., Expert Opin. Ther. Targets 12: 883-903, 2008; Uckun et al., Anti-cancer Agents Med. Chem. 7: 624-632, 2007; Lou et al, J. Med. Chem. 55(10): 4539-4550, 2012).

International application WO2014173289A disclosed a series of fused heterocyclic compounds as Btk inhibitors. In particular, WO2014173289A disclosed (S)-7-(1-(but-2-ynoyl)piperidin-4-yl)-2-(4-phenoxyphenyl)-4,5,6,7-tetrahydropyrazolo[1,5-a]pyrimidine-3-carboxamide

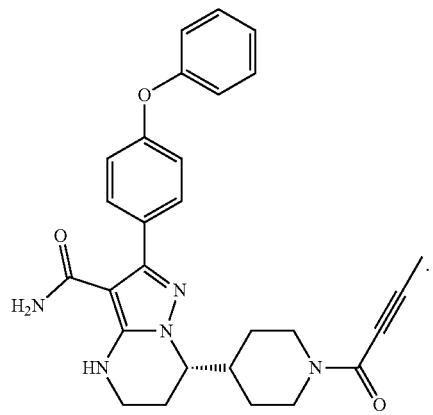

Compound 1

Compound 1 is a potent, specific and irreversible BTK kinase inhibitor. The data generated in preclinical studies using biochemical, cell based and animal studies have suggested that Compound 1 is of significant benefit in inhibiting tumor growth in B-cell malignancies. Compound 1 was shown to be more selective than ibrutinib for inhibition of BTK vs. EGFR, FGR, FRK, HER2, HER4, ITK, JAK3, LCK, and TEC, indicating that Compound 1 will have less side-effects than ibrutinib in clinic.

However, Compound 1 prepared in accordance with WO2014173289A was found to be in amorphous form, as confirmed by the X-Ray Powder Diffraction (hereinafter XRPD) pattern of FIG. 1A (the existence of a large bump distributed in a wide range) and the TGA/mDSC curves of FIG. 1B (no substantial glass transition signal). The amorphous form of Compound 1 presents some challenges for drug formulation due to its low stability and difficulties to handle. Therefore, there is a need to develop new forms of Compound 1, especially crystalline forms, which are stable and easy to handle and to process in the manufacture and preparation of drug formulations.

SUMMARY OF THE INVENTION

The inventors of the present invention have found solvated or non-solvated crystalline forms of Compound 1, which are stable and easy to handle and to process in the manufacture and preparation of drug formulations compared with the amorphous form of Compound 1. Particularly, the inventors found an anhydrous non-solvated crystalline form (i.e., Form B herein) is suitable for drug formulation due to its high melting point, non-hygroscopicity and good mechanical stability.

In a first aspect, disclosed herein is a crystalline form of Compound 1,

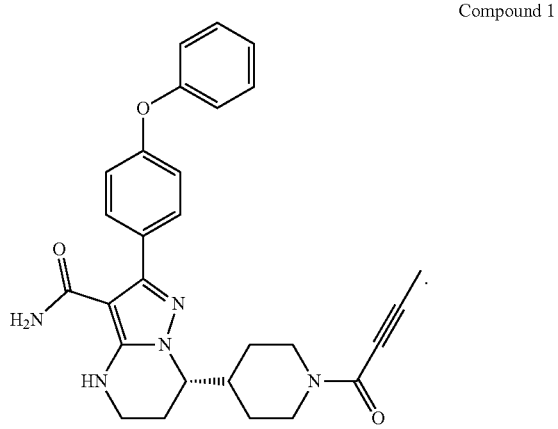 [SMILES: CC#CC(=O)N1CCC([C@@H]2CCNc3c(C(N)=O)c(-c4ccc(Oc5ccccc5)cc4)nn32)CC1]

Compound 1

In some embodiments, the crystalline form of Compound 1 is solvated (herein referred to as "Form A" or "Form A as a solvate" or "solvated crystalline form").

In some embodiments, the crystalline form of Compound 1 is anhydrous non-solvated (herein referred to as "Form B" or "non-solvated crystalline form").

In a second aspect, disclosed herein is a method of preparing Compound 1.

In a third aspect, disclosed herein is a method of preparing Form A disclosed herein.

In a forth aspect, disclosed herein is a method of preparing Form B disclosed herein.

In a fifth aspect, disclosed herein is a pharmaceutical composition comprising a therapeutically effective amount of Form A or B disclosed herein and a pharmaceutically acceptable carrier.

In a sixth aspect, disclosed herein is a method for treating a disease associated with undesirable Btk activity in a subject by administering to the subject Form A or B disclosed herein. Preferably, the disease is an allergic disease, an autoimmune disease, an inflammatory disease, or a cancer, or a combination of two or more thereof. More preferably, the disease is a B-cell proliferative disease, selected from chronic lymphocytic, non-Hodgkin's lymphoma, diffuse large B cell lymphoma, mantle cell lymphoma, follicular lymphoma, or chronic lymphocytic leukemia, or a combination of two or more thereof. In some embodiment, the inflammatory disease is selected from rheumatoid arthritis, systemic lupus erythematosus and multiple sclerosis.

In a seventh aspect, disclosed herein is a use of Form A or B disclosed herein in manufacturing a medicament for treatment of at least one disease associated with undesirable Btk activity. Preferably, the disease is an allergic disease, an autoimmune disease, an inflammatory disease, or a cancer, or a combination of two or more thereof. More preferably, the disease is a B-cell proliferative disease, selected from chronic lymphocytic, non-Hodgkin's lymphoma, diffuse large B cell lymphoma, mantle cell lymphoma, follicular lymphoma, or chronic lymphocytic leukemia, or a combination of two or more thereof. In some embodiment, the inflammatory disease is selected from rheumatoid arthritis, systemic lupus erythematosus and multiple sclerosis.

BRIEF DESCRIPTIONS OF THE DRAWINGS

FIG. 4A shows the XRPD pattern of Crystalline Form B.

DETAILED DESCRIPTION OF THE INVENTION

The inventors have found that Compound 1 can exist in crystalline forms, either solvated or non-solvated.

In some embodiments, Compound 1 is in solvated crystalline form (i.e., Form A). In a preferred embodiment, Form A is solvated with EtOAc (also referred to as "Form A as an EtOAc solvate"). In other embodiments, Form A is solvated with other solvent or anti-solvent or is to form a hetero-solvate.

In some embodiments, Compound 1 is in Form A characterized by an XRPD comprising diffraction peaks having 2θ angle values independently selected from: approximately 5.3±0.2°, 16.9±0.2°, 18.6±0.2°, 19.8±0.2° and 20.6±0.2°.

In some embodiments, Compound 1 is in Form A characterized by an XRPD comprising diffraction peaks having 2θ angle values independently selected from: approximately 5.3±0.2°, 16.9±0.2°, 18.6±0.2°, 19.8±0.2° and 20.6±0.2°.

In some embodiments, Compound 1 is in Form A characterized by an XRPD comprising diffraction peaks having 2θ angle values independently selected from: approximately 5.3±0.2°, 10.9±0.2°, 16.9±0.2°, 18.6±0.2°, 19.8±0.2°, 20.6±0.2°, 21.1±0.2°, 22.5±0.2° and 22.8±0.20.

In some embodiments, Compound 1 is in Form A characterized by an XRPD comprising diffraction peaks having 2θ angle values independently selected from: approximately 5.3±0.2°, 10.9±0.2°, 11.2±0.2°, 13.4±0.2°, 14.4±0.2°, 16.9±0.2°, 18.6±0.2°, 19.8±0.2°, 20.6±0.2°, 21.1±0.2°, 21.7±0.2°, 22.5±0.2°, 22.8±0.2°, 23.6±0.2° and 24.3±0.2°.

In some embodiments, Compound 1 is in Form A characterized by an XRPD comprising diffraction peaks having 2θ angle values independently selected from: approximately 5.3±0.2°, 10.9±0.2°, 11.2±0.2°, 12.0±0.2°, 13.4±0.2°, 14.1±0.2°, 14.4±0.2°, 16.9±0.2°, 18.1±0.2°, 18.6±0.2°, 19.8±0.2°, 20.6±0.2°, 21.1±0.2°, 21.7±0.2°, 22.5±0.2°, 22.8±0.2°, 23.6±0.2°, 24.0±0.2° and 24.3±0.2°.

In some embodiments, Compound 1 is in Form A characterized by an XRPD comprising diffraction peaks having 2θ angle values independently selected from: approximately 5.3±0.2°, 9.2±0.2°, 10.9±0.2°, 11.2±0.2°, 12.0±0.2°, 13.4±0.2°, 14.1±0.2°, 14.4±0.2°, 15.5±0.2°, 16.9±0.2°, 17.7±0.2°, 18.1±0.2°, 18.6±0.2°, 19.8±0.2°, 20.6±0.2°, 21.1±0.2°, 21.7±0.2°, 22.5±0.2°, 22.8±0.2°, 23.6±0.2°, 24.0±0.2°, 24.3±0.2° and 26.4±0.2°.

Figure 1A:
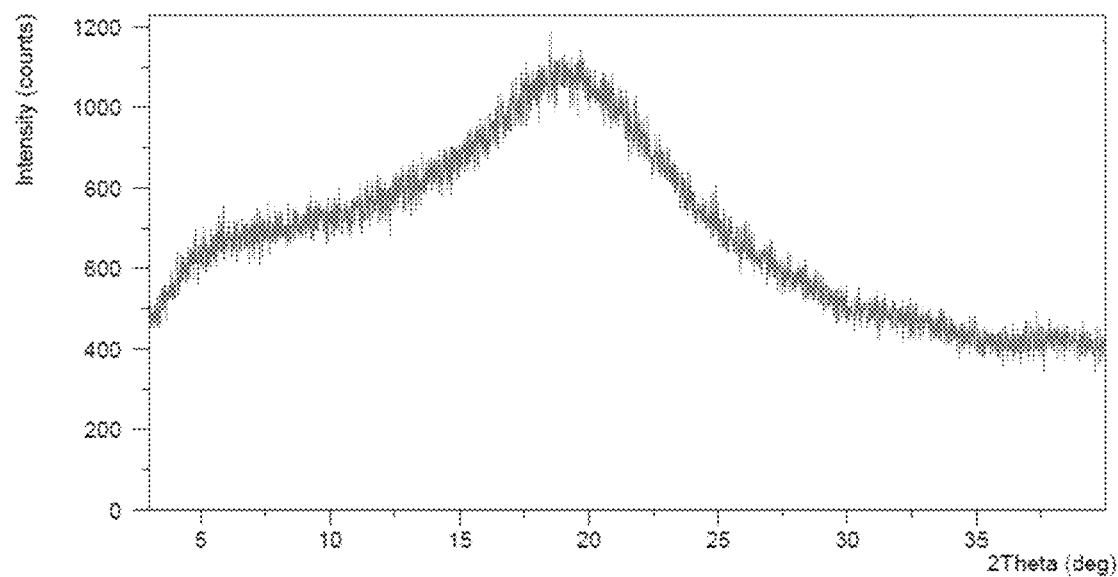
FIG. 1A shows the XRPD pattern of the amorphous form of Compound 1.
Figure 1B:
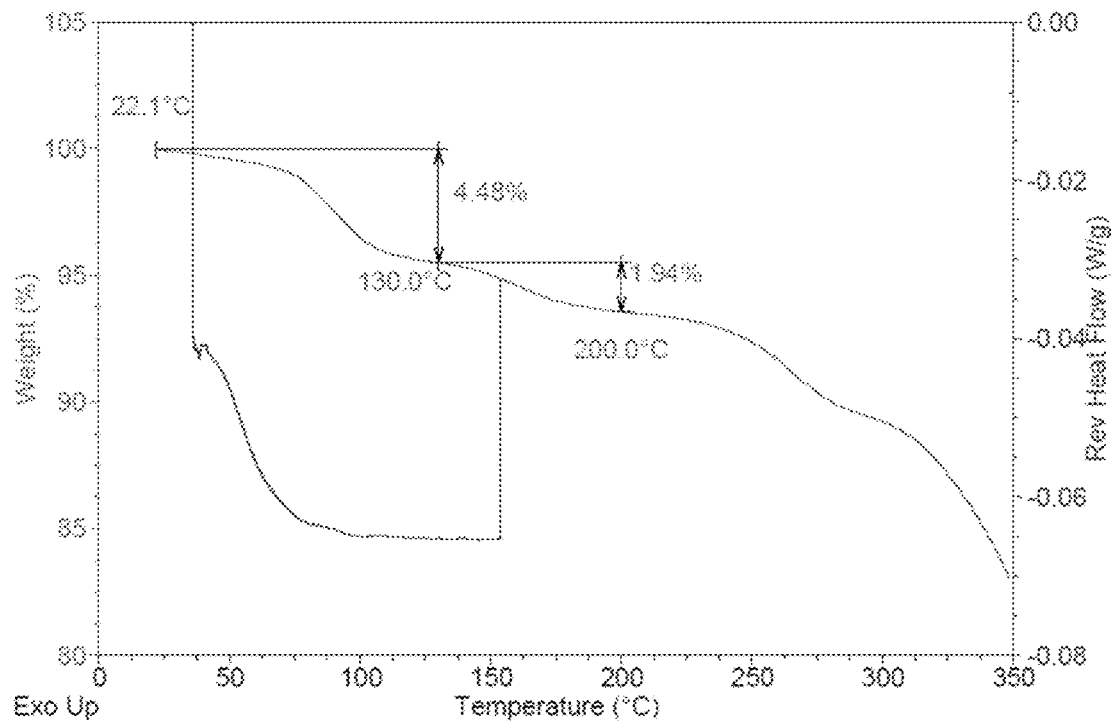
FIG. 1B shows the TGA/mDSC curves of amorphous form of Compound 1.
Figure 2A:
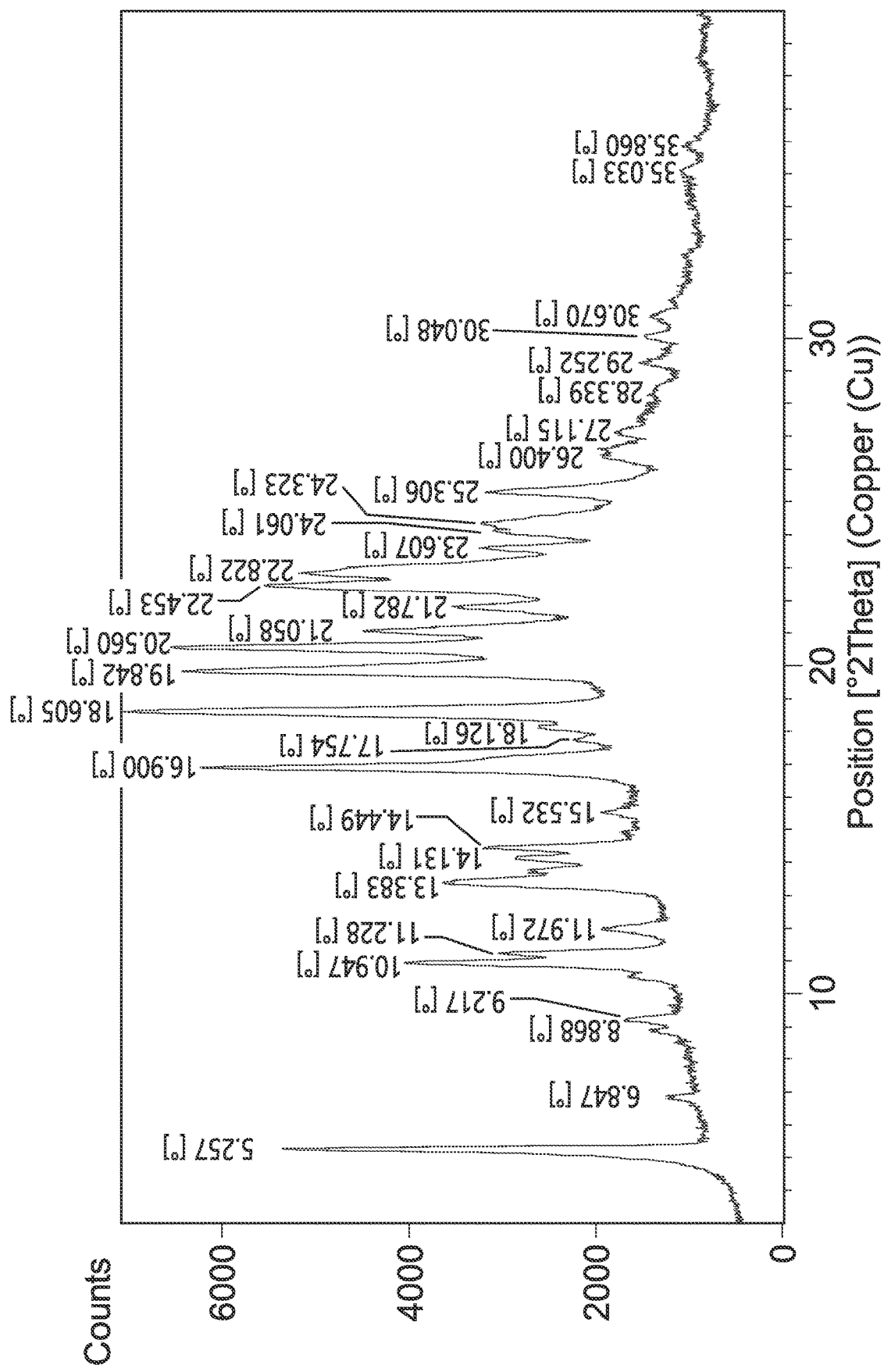
FIG. 2A shows the XRPD pattern of Form A (crystallization from EtOAc/n-heptane).

In some embodiments, Compound 1 is in Form A characterized by an XRPD substantially in accordance with FIG. 2A.

In some embodiments, Compound 1 is in Form A characterized by an XRPD summarized in Table 1.

TABLE 1

X-ray Diffraction Pattern of Form A of Compound 1

| Peak# | Diffraction angle (2 theta) | Spacing | Relative intensity |
|---|---|---|---|
| 1 | 5.257 | 16.80987 | 75.65 |
| 2 | 6.847 | 12.91043 | 9.90 |
| 3 | 8.868 | 9.97248 | 12.65 |
| 4 | 9.217 | 9.59468 | 16.83 |
| 5 | 10.947 | 8.08267 | 54.46 |
| 6 | 11.228 | 7.88084 | 38.01 |
| 7 | 11.972 | 7.39264 | 19.97 |
| 8 | 13.383 | 6.61638 | 46.72 |
| 9 | 14.131 | 6.26740 | 34.23 |
| 10 | 14.449 | 6.13029 | 39.26 |
| 11 | 15.532 | 5.70515 | 18.97 |
| 12 | 16.900 | 5.24643 | 87.03 |
| 13 | 17.754 | 4.99588 | 23.00 |
| 14 | 18.126 | 4.89410 | 29.17 |
| 15 | 18.605 | 4.76923 | 100.00 |
| 16 | 19.842 | 4.47464 | 88.29 |
| 17 | 20.560 | 4.31994 | 90.99 |
| 18 | 21.058 | 4.21899 | 57.80 |
| 19 | 21.782 | 4.08036 | 41.63 |
| 20 | 22.453 | 3.95982 | 74.39 |
| 21 | 22.822 | 3.89668 | 67.54 |
| 22 | 23.607 | 3.76878 | 37.10 |
| 23 | 24.061 | 3.69869 | 33.71 |

TABLE 1-continued

X-ray Diffraction Pattern of Form A of Compound 1

| Peak# | Diffraction angle (2 theta) | Spacing | Relative intensity |
|---|---|---|---|
| 24 | 24.323 | 3.65943 | 36.77 |
| 25 | 25.306 | 3.51949 | 35.61 |
| 26 | 26.400 | 3.37615 | 16.09 |
| 27 | 27.115 | 3.28872 | 13.51 |
| 28 | 28.339 | 3.14940 | 7.03 |
| 29 | 29.252 | 3.05308 | 8.39 |
| 30 | 30.048 | 2.97402 | 8.02 |
| 31 | 30.670 | 2.91511 | 6.82 |
| 32 | 35.033 | 2.56145 | 3.45 |
| 33 | 35.860 | 2.50421 | 3.48 |

Figure 2B:
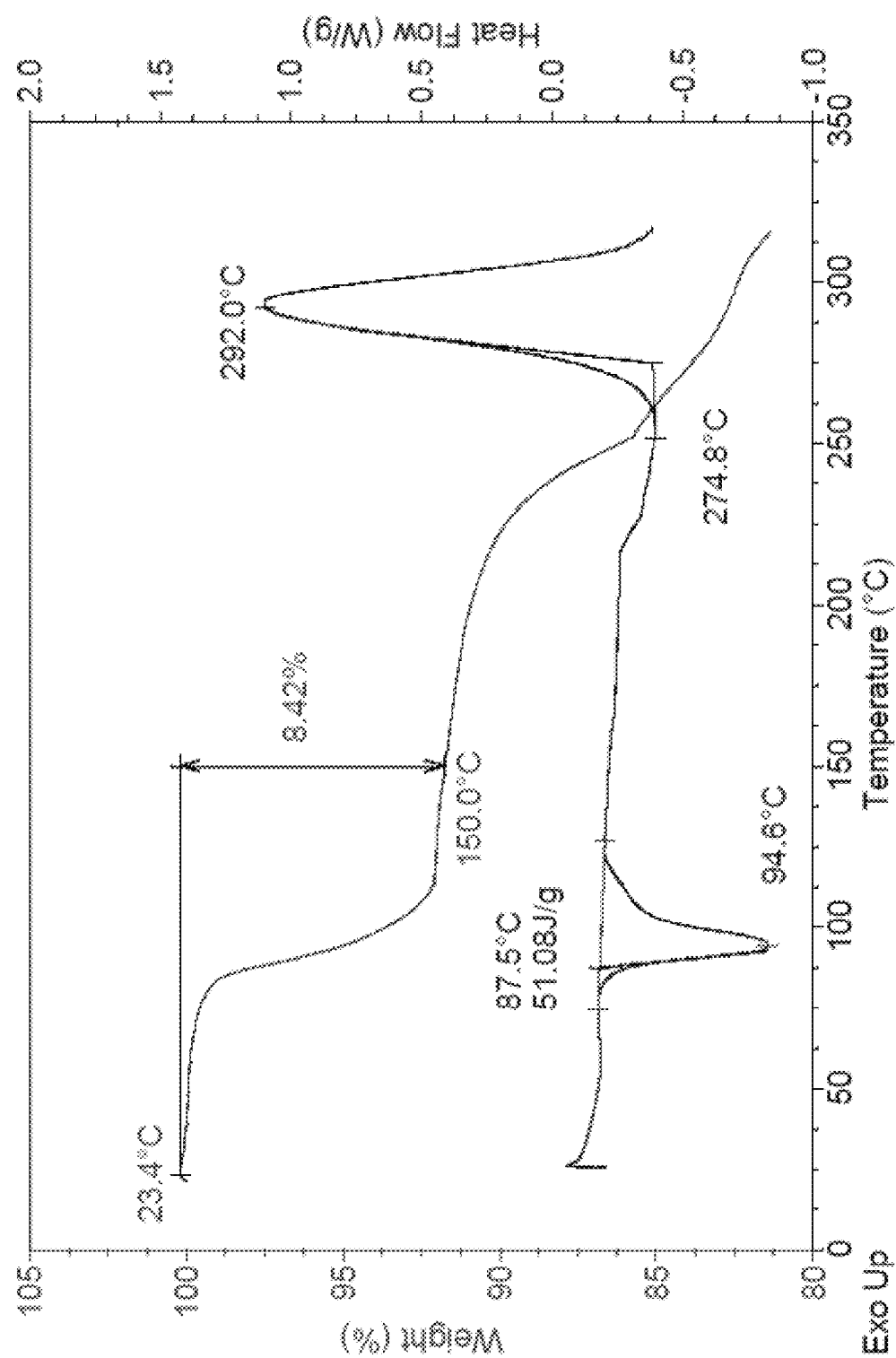
FIG. 2B shows the TGA/DSC curves of Form A (crystallization from EtOAc/n-heptane).

In some preferred embodiments, Compound 1 is in Form A as an EtOAc solvate characterized by a DSC substantially in accordance with FIG. 2B.

In some preferred embodiments, Compound 1 is in Form A as an EtOAc solvate characterized by a TGA substantially in accordance with FIG. 2B.

In some embodiments, Compound 1 is in Form B characterized by an XRPD comprising diffraction peaks having 2θ angle values independently selected from: approximately 15.1±0.2°, 20.7±0.2° and 22.8±0.2°.

In some embodiments, Compound 1 is in Form B characterized by an XRPD comprising diffraction peaks having 2θ angle values independently selected from: approximately 15.1±0.2°, 15.5±0.2°, 19.9±0.2°, 20.7±0.2°, 21.7±0.2° and 22.8±0.2°.

In some embodiments, Compound 1 is in Form B characterized by an XRPD comprising diffraction peaks having 2θ angle values independently selected from: approximately 15.1±0.2°, 15.5±0.2°, 17.0±0.2°, 19.9±0.2°, 20.0±0.2°, 20.7±0.2°, 21.7±0.2°, 22.8±0.2° and 24.2±0.20.

In some embodiments, Compound 1 is in Form B characterized by an XRPD comprising diffraction peaks having 2θ angle values independently selected from: approximately 6.3±0 0.2°, 9.5±0.2°, 15.1±0.2°, 15.5±0.2°, 16.5±0.2°, 17.0±0.2°, 19.9±0.2°, 20.0±0.2°, 20.7±0.2°, 21.7±0.2°, 22.8±0.2°, 24.2±0.2° and 25.1±0.2°.

In some embodiments, Compound 1 is in Form B characterized by an XRPD comprising diffraction peaks having 2θ angle values independently selected from: approximately 6.3±0 0.2°, 9.5±0.2°, 12.4±0.2°, 13.2±0.2°, 15.1±0.2°, 15.5±0.2°, 16.5±0.2°, 17.0±0.2°, 18.0±0.2°, 18.9±0.2°, 19.9±0.2°, 20.0±0.2°, 20.7±0.2°, 21.7±0.2°, 22.8±0.2°, 24.2±0.2°, 25.1±0.2°, 25.8±0.2°, 26.7±0.2° and 27.6±0.2°.

In some embodiments, Compound 1 is in Form B characterized by an XRPD substantially in accordance with FIG. 4A.

I In some embodiments, Compound 1 is in Form B characterized by an XRPD summarized in Table 2.

TABLE 2

X-ray Diffraction Pattern of Compound 1 Crystalline Form B

| Peak# | Diffraction angle (2 theta) | Spacing | Relative intensity |
|---|---|---|---|
| 1 | 6.266 | 14.10502 | 21.70 |
| 2 | 9.483 | 9.32619 | 22.34 |
| 3 | 11.455 | 7.72521 | 3.92 |
| 4 | 12.395 | 7.14115 | 11.38 |
| 5 | 12.832 | 6.89900 | 12.73 |
| 6 | 13.252 | 6.68146 | 12.21 |
| 7 | 15.095 | 5.86950 | 100.00 |
| 8 | 15.513 | 5.71236 | 66.31 |
| 9 | 16.530 | 5.36287 | 21.11 |

TABLE 2-continued

X-ray Diffraction Pattern of Compound 1 Crystalline Form B

| Peak# | Diffraction angle (2 theta) | Spacing | Relative intensity |
|---|---|---|---|
| 10 | 17.016 | 5.21086 | 44.01 |
| 11 | 18.032 | 4.91940 | 22.41 |
| 12 | 18.839 | 4.71056 | 22.97 |
| 13 | 18.946 | 4.68427 | 26.61 |
| 14 | 19.519 | 4.54788 | 9.92 |
| 15 | 19.897 | 4.46247 | 61.31 |
| 16 | 20.081 | 4.42199 | 31.97 |
| 17 | 20.687 | 4.29383 | 97.71 |
| 18 | 21.722 | 4.09137 | 58.94 |
| 19 | 22.800 | 3.90041 | 97.94 |
| 20 | 24.243 | 3.67138 | 32.46 |
| 21 | 24.822 | 3.58706 | 13.83 |
| 22 | 25.110 | 3.54655 | 27.64 |
| 23 | 25.757 | 3.45886 | 12.94 |
| 24 | 26.306 | 3.38790 | 11.20 |
| 25 | 26.732 | 3.33487 | 10.85 |
| 26 | 27.334 | 3.26277 | 10.51 |
| 27 | 27.665 | 3.22453 | 13.80 |
| 28 | 28.480 | 3.13406 | 4.80 |
| 29 | 29.298 | 3.04844 | 5.98 |
| 30 | 29.765 | 3.00164 | 8.35 |
| 31 | 30.128 | 2.96635 | 5.63 |
| 32 | 30.789 | 2.90412 | 5.73 |
| 33 | 31.326 | 2.85555 | 6.85 |
| 34 | 31.613 | 2.83028 | 6.13 |
| 35 | 32.049 | 2.79277 | 8.88 |
| 36 | 32.983 | 2.71581 | 5.91 |
| 37 | 34.973 | 2.56565 | 8.57 |
| 38 | 37.038 | 2.42722 | 1.32 |
| 39 | 38.049 | 2.36504 | 3.63 |

In some preferred embodiments, Compound 1 is in Form B characterized by a melting point of about 153.9±2.0° C. (onset temperature).

Figure 4B:
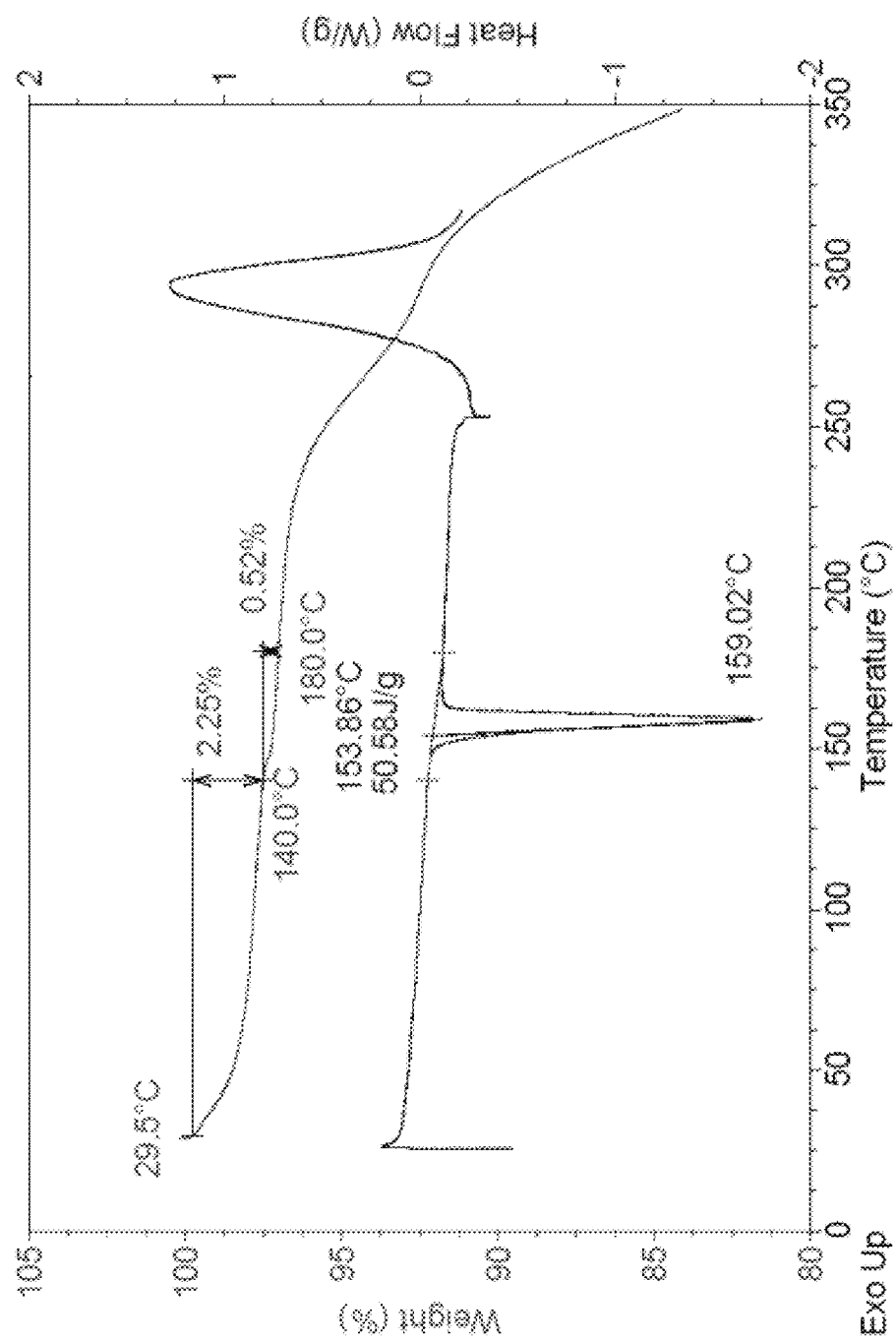
FIG. 4B shows the TGA/DSC curves of Form B.

In some preferred embodiments, Compound 1 is in Form B characterized by a DSC substantially in accordance with FIG. 4B.

In some preferred embodiments, Compound 1 is in Form B characterized by a TGA substantially in accordance with FIG. 4B.

Also disclosed herein is a method for preparing Compound 1, such as the procedures depicted in Scheme 1. The new synthetic methods and the crystallization/recrystallization procedures of Compound A via Form A or B disclosed herein overcome many issues associated with the processes reported previously, such as preparation of the key chiral intermediate with >98% optical purity, improve the purity of Compound 1 to reach the acceptance criteria in the specification, control the impurities in Compound 1 and provide many advantages over the existing processes. Notably, the methods disclosed herein are especially suitable for reproducible, commercial-scale manufacture of Compound 1 in high quality and good yields. In an alternative process, BG-9 or its analogs in Scheme 1 could be asymmetrically reduced with low to excellent enantioselectivities (5% ee. to 95% ee). The process of other steps are similar to those listed in Scheme 1. And the absolute configurations of Compound 1 was deduced to be S from the single crystal X-ray structural analysis of intermediate BG-13.

Scheme 1: Preparation of Compound 1

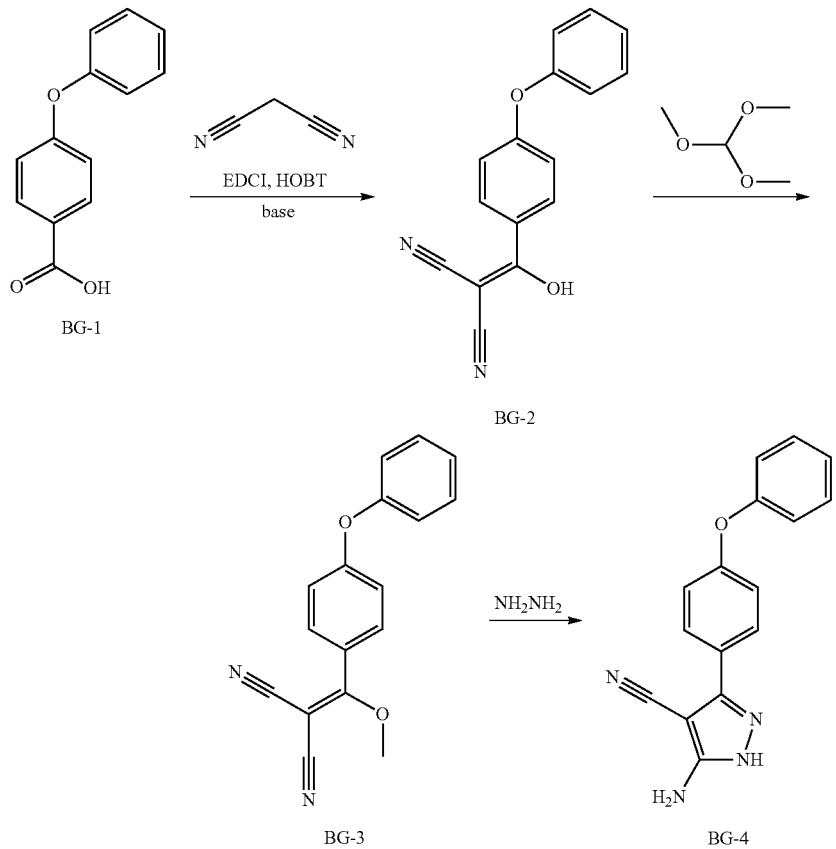

-continued
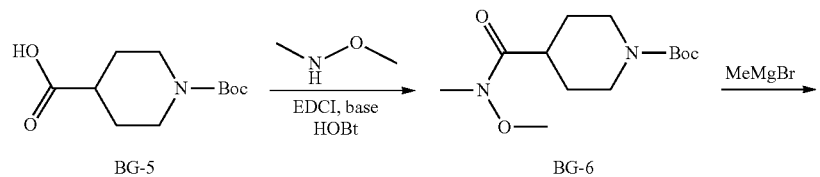
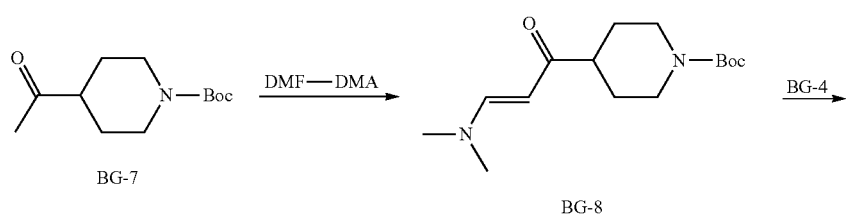
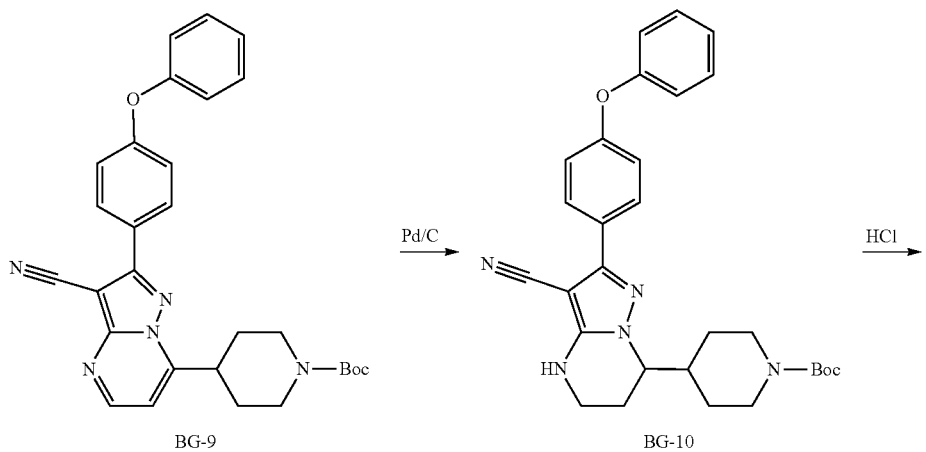
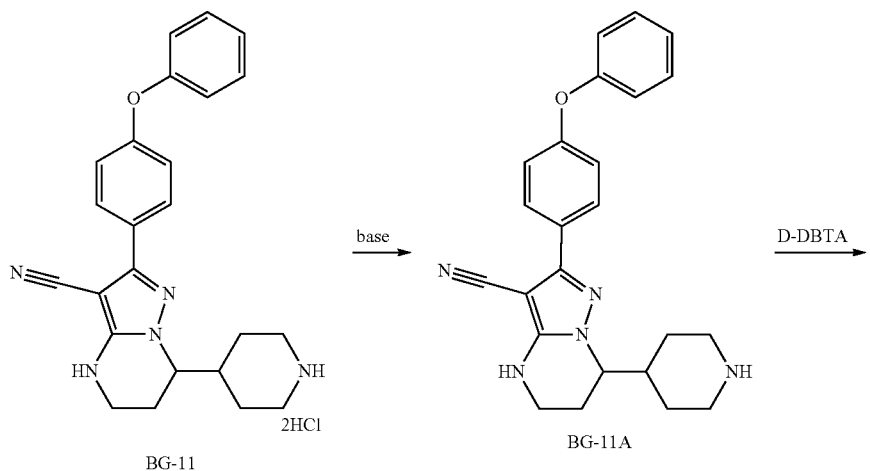

-continued
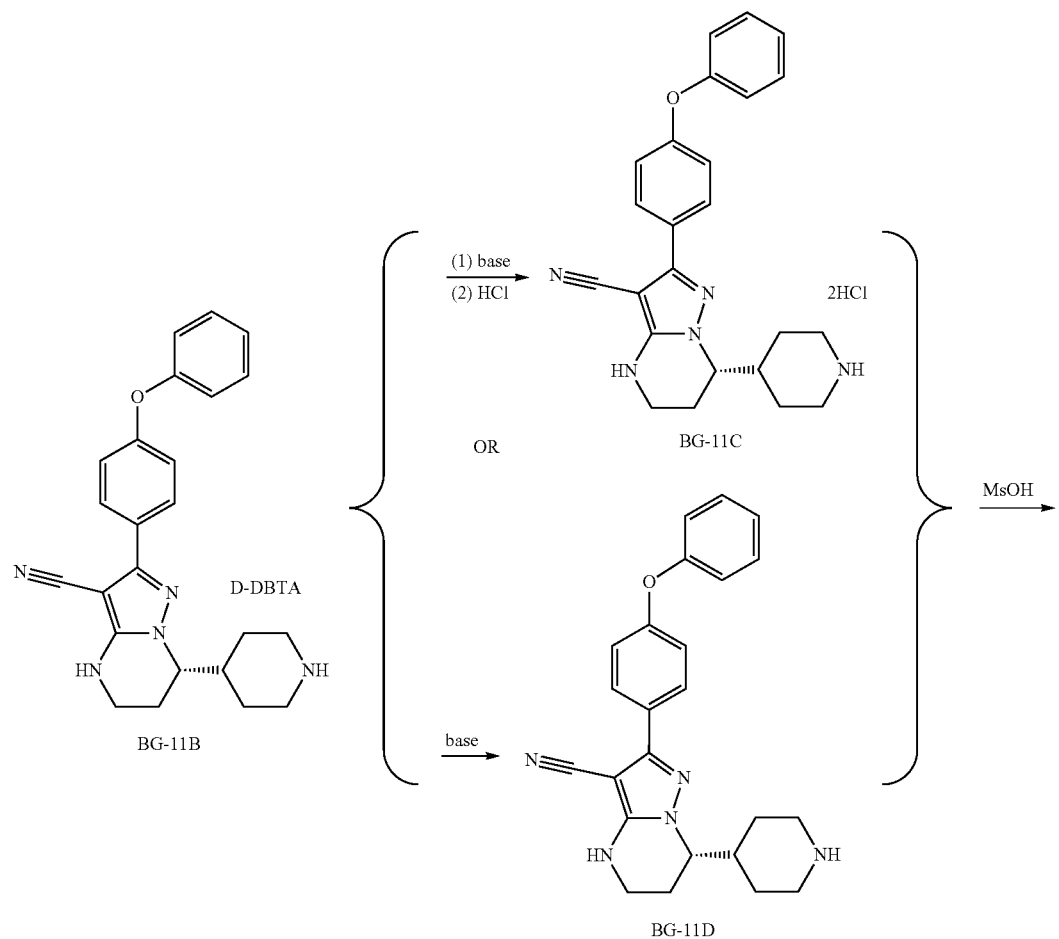
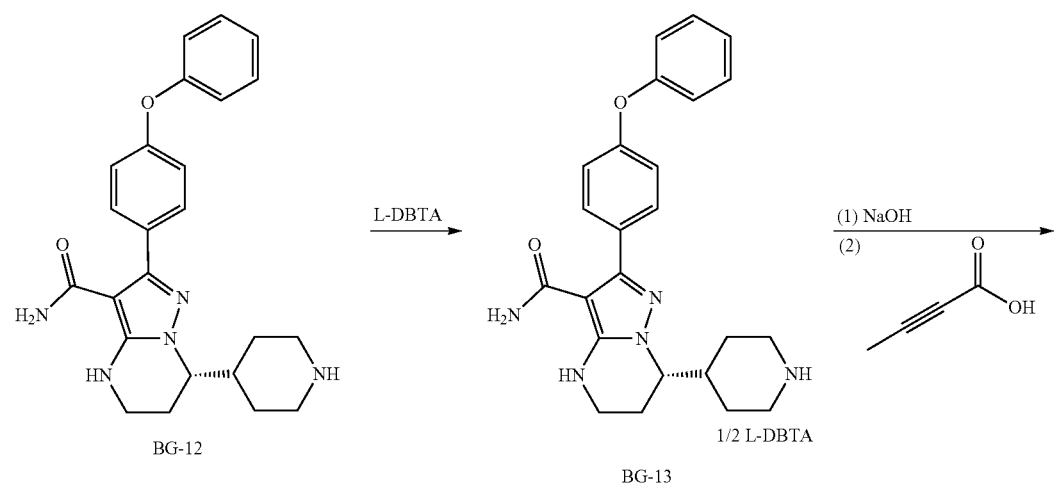

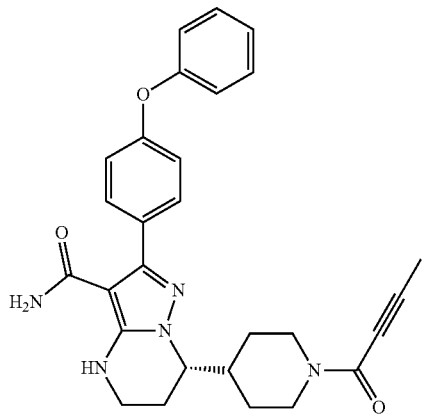

Compound 1

Also disclosed herein are methods of preparing Form A or Form B.

Disclosed herein is a method of preparing Form A of Compound 1, comprising:
(a) Dissolving Compound 1 in amorphous form in a solvent;
(b) Adding an anti-solvent into the solution of step (a) to induce precipitation;
(c) Keeping the mixture of step (b) at a temperature of or below 25° C. to precipitate Form A.

In some embodiments, the solvent used in step (a) is $C_{1-4}$alkyl alcohol (e.g., MeOH, EtOH, isopropyl alcohol), acetone, 4-Methyl-2-pentanone, EtOAc, isopropyl acetate, tetrahydrofuran, 2-methyltetrahydrofuran, 1,4-dioxane, acetonitrile, $CHCl_3$, dichloromethane, toluene, N,N-dimethylacetamide, dimethylsulfoxide, 1-methyl-2-pyrrolidone, or acetic acid or mixtures thereof. Preferably, the solvent used in step (a) is EtOH, acetone or EtOAc.

In some embodiments, the anti-solvent used in step (b) is an aliphatic hydrocarbon, which preferably is a hexane such as n-hexane, a heptane such as n-heptane, a cyclohexane and/or petroleum ether; and an aliphatic ether, which preferably is MTBE; or $H_2O$ or mixtures thereof. Preferably, the anti-solvent used in step (b) is n-hexane, n-heptane, MTBE, or $H_2O$. More preferably, the anti-solvent used in step (b) is n-hexane or n-heptane.

The ratio of the solvent used in step (a) and the anti-solvent used in step (b) can be easily determined by a skilled person in the art once the solvent and the anti-solvent have been selected. In practice, more anti-solvent may be added to induce precipitation of the desired crystalline form. In some embodiments, the volumetric ratio of the solvent/anti-solvent ratio is from 2:1 to 1:7 or higher. Specifically, the volumetric ratio of the solvent:anti-solvent ratio is 2:1, 1:1, 1:2, 1:3, 1:4, 1:5, 1:6, 1:7, or higher, depending on whether the desired amount of crystalline form has been recovered.

The temperature at which step (a) is conducted is usually room temperature, although a higher temperature may be used to aid dissolution.

In some embodiments, the temperature at which step (c) is conducted is 25° C. In other embodiments, the temperature at which step (c) is conducted is below 25° C., such as RT, 10° C. or 5° C.

The time duration for which step (c) is conducted may be adjusted by the amount of the solids which have precipitated. The time duration may be 1 hours, 2 hours, 12 hours, 24 hours, 48 hours, 72 hours or longer.

In some embodiments, the mixture of step (b) is optionally seeded with Form A to facilitate crystallization before step (c).

In some embodiment, step (c) is conducted with stirring or agitation.

In some embodiments, Form A is solvated. In some embodiment, the solvent used in step (a) is EtOAc, and Form A is Form A as an EtOAc solvate.

In some embodiments, the resultant solvated Form A may be further converted into a different solvate by a method comprising
(a') Dissolving the resultant Form A in a second solvent;
(b') Adding a second anti-solvent into the solution of step (a') to induce precipitation;
(c') Keeping the mixture of step (b') at a temperature of or below 25° C. to precipitate Form A as a different solvate.

In some embodiment, the second solvent is different from the one to dissolve Compound 1 in amorphous form, such as EtOH or acetone. In a further embodiment, the second solvent is EtOH, the anti-solvent used in step (b) is n-heptane, and Form A is Form A as a hetero-solvate of EtOH and n-heptane.

Alternatively, a method of preparing Form A of Compound 1 comprises suspending or slurrying Compound 1 in amorphous form in a liquid system at a temperature of or below 25° C. to precipitate Form A.

In some embodiments, the liquid system is at least a solvent, or at least an anti-solvent, or a mixture of at least a solvent and at least an anti-solvent. The solvent is $C_{1-4}$alkyl alcohol (e.g., MeOH, EtOH, isopropyl alcohol), acetone, 4-Methyl-2-pentanone, EtOAc, isopropyl acetate, tetrahydrofuran, 2-methyltetrahydrofuran, 1,4-dioxane, acetonitrile, $CHCl_3$, dichloromethane, toluene, N,N-dimethylacetamide, dimethylsulfoxide, 1-methyl-2-pyrrolidone, or acetic acid or mixtures thereof. Preferably, the solvent is EtOH, acetone or EtOAc. The anti-solvent is an aliphatic hydrocarbon, which preferably is a hexane such as n-hexane, a heptane such as n-heptane, a cyclohexane and/or petroleum ether; and an aliphatic ether, which preferably is MTBE; or $H_2O$ or mixtures thereof. Preferably, the anti-solvent is n-hexane, n-heptane, MTBE, or $H_2O$. More preferably, the anti-solvent is n-hexane or n-heptane.

Preferably, the liquid system is a mixture of at least a solvent and at least an anti-solvent. The ratio of the solvent and the anti-solvent can be easily determined by a skilled person in the art once the solvent and the anti-solvent have been selected. In some embodiments, the volumetric ratio of the solvent/anti-solvent ratio is from 2:1 to 1:7 or higher. Specifically, the volumetric ratio of the solvent:anti-solvent ratio is 2:1, 1:1, 1:2, 1:3, 1:4, 1:5, 1:6, 1:7, or higher.

In some embodiments, the temperature is 25° C. In other embodiments, the temperature is conducted is below 25° C., such as RT, 10° C. or 5° C. In some embodiments, the temperature is 5° C. and the liquid system is isopropyl acetate, $H_2O$, MTBE, n-heptane, NMP/$H_2O$, THF/n-heptane, 1,4-Dioxane/n-heptane, EtOAc/n-heptane, or DCM/MTBE. In other embodiments, the temperature is RT, and the liquid system is isopropyl acetate, MTBE, THF/n-heptane, 1,4-dioxane/n-heptane, EtOAc/n-heptane, or $CHCl_3$/MTBE.

The time duration for the suspending or slurrying procedure may be adjusted by the amount of the solids which have precipitated. The time duration may be 1 hours, 2 hours, 12 hours, 24 hours, 48 hours, 72 hours or longer.

In some embodiments, the method comprises optionally adding Form A as seeds to facilitate crystallization.

In some embodiment, the suspending or slurrying procedure is conducted with stirring or agitation.

In some embodiments, the resultant solvated Form A may be further converted into a different solvate by suspending or slurrying the resultant solvated Form A in a different liquid system at a temperature of or below 25° C.

Also disclosed herein is a method of preparing Form B of Compound 1, comprising:
(a) Dissolving Compound 1 in Form A or in amorphous form in a solvent;
(b) Adding an anti-solvent into the solution of step (a) to induce precipitation;
(c) Keeping the mixture of step (b) at a temperature of between 40° C. and 60° C. to precipitate Form B.

In some embodiments, the solvent used in step (a) is acetone, 4-Methyl-2-pentanone, EtOAc, isopropyl acetate, tetrahydrofuran, 2-methyltetrahydrofuran, 1,4-dioxane, acetonitrile, $CHCl_3$, dichloromethane, toluene, N,N-dimethylacetamide, dimethylsulfoxide, 1-methyl-2-pyrrolidone, or acetic acid or mixtures thereof. Preferably, the solvent used in step (a) is THF, $CHCl_3$, acetone or EtOAc.

In some embodiments, the anti-solvent used in step (b) is an aliphatic hydrocarbon, which preferably is a hexane such as n-hexane, a heptane such as n-heptane, a cyclohexane and/or petroleum ether; and an aliphatic ether, which preferably is MTBE; or $H_2O$ or mixtures thereof. Preferably, the anti-solvent used in step (b) is n-hexane, n-heptane, MTBE, or $H_2O$. More preferably, the anti-solvent used in step (b) is n-hexane or n-heptane or MTBE.

The ratio of the solvent used in step (a) and the anti-solvent used in step (b) can be easily determined by a skilled person in the art once the solvent and the anti-solvent have been selected. In practice, more anti-solvent may be added to induce precipitation of the desired crystalline form. In some embodiments, the volumetric ratio of the solvent/anti-solvent ratio is from 2:1 to 1:7 or higher. Specifically, the volumetric ratio of the solvent:anti-solvent ratio is 2:1, 1:1, 1:2, 1:3, 1:4, 1:5, 1:6, 1:7, or higher, depending on whether the desired amount of crystalline form has been recovered.

The temperature at which step (a) is conducted is usually room temperature, although a higher temperature may be used to aid dissolution.

In some embodiments, the temperature at which step (c) is conducted is between 50° C. to 60° C. In other embodiments, the temperature at which step (c) is conducted is 50° C. or 55° C.

The time duration for which step (c) is conducted may be adjusted by the amount of the solids which have precipitated. The time duration may be 1 hours, 2 hours, 12 hours, 24 hours, 48 hours, 72 hours or longer.

In some embodiments, the mixture of step (b) is optionally seeded with Form B to facilitate crystallization before step (c).

In some embodiments, the resultant Form B is anhydrous non-solvated.

Alternatively, a method of preparing Form B of Compound 1 comprises suspending or slurrying Compound 1 in amorphous form or in Form A in a liquid system at a temperature of between 40° C. and 60° C. to precipitate Form B.

In some embodiments, the liquid system is at least a solvent, or at least an anti-solvent, or a mixture of at least a solvent and at least an anti-solvent. The solvent is acetone, 4-Methyl-2-pentanone, EtOAc, isopropyl acetate, tetrahydrofuran, 2-methyltetrahydrofuran, 1,4-dioxane, acetonitrile, $CHCl_3$, dichloromethane, toluene, N,N-dimethylacetamide, dimethylsulfoxide, 1-methyl-2-pyrrolidone, or acetic acid or mixtures thereof. Preferably, the solvent is EtOH, acetone or EtOAc. The anti-solvent is an aliphatic hydrocarbon, which preferably is a hexane such as n-hexane, a heptane such as n-heptane, a cyclohexane and/or petroleum ether; and an aliphatic ether, which preferably is MTBE; or mixtures thereof. Preferably, the anti-solvent is n-hexane, n-heptane, MTBE. More preferably, the anti-solvent is n-hexane or n-heptane.

Preferably, the liquid system is a mixture of at least a solvent and at least an anti-solvent, preferably EtOAc/n-hexane, EtOAc/n-hexane, Acetone/n-heptane, THF/n-heptane, $CHCl_3$/n-heptane, $CHCl_3$/MTBE, or Acetone/MTBE.

The ratio of the solvent and the anti-solvent can be easily determined by a skilled person in the art once the solvent and the anti-solvent have been selected. In some embodiments, the volumetric ratio of the solvent/anti-solvent ratio is from 2:1 to 1:7 or higher. Specifically, the volumetric ratio of the solvent:anti-solvent ratio is 2:1, 1:1, 1:2, 1:3, 1:4, 1:5, 1:6, 1:7, or higher. Preferably, the liquid is EtOAc/n-hexane (1:1), EtOAc/n-hexane (1:3), Acetone/n-heptane (1:3), THF/n-heptane (1:3), $CHCl_3$/n-heptane (1:3), $CHCl_3$/MTBE (1:5). or Acetone/MTBE (1:5).

In some embodiments, the temperature for slurrying or suspending is between 50° C. to 60° C. In other embodiments, the temperature for slurrying or suspending is conducted is 50° C. or 55° C.

The time duration for the suspending or slurrying procedure may be adjusted by the amount of the solids which have precipitated. The time duration may be 1 hours, 2 hours, 12 hours, 24 hours, 48 hours, 72 hours or longer.

In some embodiments, the method comprises optionally adding Form B as seeds to facilitate crystallization.

In some embodiment, the suspending or slurrying procedure is conducted with stirring or agitation.

Also disclosed herein is a pharmaceutical composition comprises a therapeutically effective amount of Form A or B, and a pharmaceutically acceptable excipient. In some embodiments, the pharmaceutical composition is used in an oral administration. In some preferred embodiments, the pharmaceutical composition comprises 1 wt % to 99 wt % of Form A or B. In some more preferred embodiments, the pharmaceutical composition comprises 1 wt % to 70 wt % of Form A or B. In some most embodiments, the pharmaceutical composition comprises 10 wt % to 30 wt % of Form A or B.

Disclosed herein is a method of treating or preventing a disease associated with undesirable Btk activity in a subject by administering to a subject Form A or B.

Disclosed herein is a method of treating or preventing a disease selected from an allergic disease, an autoimmune disease, an inflammatory disease, a cancer, or a combination of two or more thereof in a subject by administering to the subject Form A or B.

Disclosed herein is a method of treating or preventing a B-cell proliferative disease, selected from chronic lymphocytic, non-Hodgkin's lymphoma, diffuse large B cell lymphoma, mantle cell lymphoma, follicular lymphoma, chronic lymphocytic leukemia, or a combination of two or more thereof in a subject by administering to the subject Form A or B.

Form A or B disclosed herein can be used in manufacturing a medicament for treatment of at least one disease associated with undesirable Btk activity, in a subject.

Form A or B disclosed herein can be used in manufacturing a medicament for the treatment of a disease selected from an allergic disease, an autoimmune disease, an inflammatory disease, a cancer, or a combination of two or more thereof, in a subject.

Form A or B disclosed herein can be used in manufacturing a medicament for the treatment of a B-cell proliferative disease selected from chronic lymphocytic, non-Hodgkin's lymphoma, diffuse large B cell lymphoma, mantle cell lymphoma, follicular lymphoma, chronic lymphocytic leukemia, or a combination of two or more thereof, in a subject.

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise. Thus, for example, reference to "a crystalline form" includes one or more of such different crystalline forms and reference to "the method" includes reference to equivalent steps and methods know to those of ordinary skill in the art that could be modified or substituted for the methods described herein.

As disclosed herein, the crystalline form is an approximately pure crystalline. The term "approximately pure" as herein used refers to at least 85 wt %, preferably at least 95 wt %, more preferably at least 99 wt % of Form A or B disclosed herein.

For crystalline forms disclosed herein, only the main peaks (i.e., the most characteristic, significant, unique and/or reproducible peaks) are summarized; additional peaks may be obtained from the diffraction spectra by conventional methods. The main peaks described above can be reproduced within the margin of error (±2 at the last given decimal place, or ±0.2 at the stated value).

As disclosed herein, "an XRPD substantially in accordance with FIG. 2A" refers to the XRPD that show major peaks as in FIG. 2A, wherein major peaks refer to those with the relative intensity greater than 10%, preferably greater than 20%, relative to the highest peak (with its relative intensity designated to be 100%) in FIG. 2A.

The term "solvent" used herein refers to a liquid in which Compound 1 or Form A or Form B is dissolved or partially dissolved at RT with the solubility greater than 2 mg/mL at RT, preferably greater than 10 mg/mL at RT. Examples of the solvent in which Compound 1 in either amorphous form or Form A or Form B is dissolvable or partially dissolvable include, but no limited to, $C_{1-4}$alkyl alcohol (e.g., MeOH, EtOH, isopropyl alcohol), acetone, 4-Methyl-2-pentanone, EtOAc, isopropyl acetate, tetrahydrofuran, 2-methyltetrahydrofuran, 1,4-dioxane, acetonitrile, $CHCl_3$, dichloromethane, toluene, N,N-dimethylacetamide, dimethylsulfoxide, 1-methyl-2-pyrrolidone, acetic acid and so on.

The term "anti-solvent" used herein refers to a liquid which can induce precipitation for crystallization of Form A or Form B and in which the solubility of Form A or Form B is less than 2 mg/mL at RT. Examples of the anti-solvent which induces precipitation for crystallization of Form A or Form B include, but not limited to, an aliphatic hydrocarbon, which preferably is a hexane such as n-hexane, a heptane such as n-heptane, a cyclohexane and/or petroleum ether; and an aliphatic ether, which preferably is MTBE; $H_2O$ and mixtures thereof. Preferably, the anti-solvent for Form A or Form B is n-hexane, n-heptane, MTBE, or $H_2O$.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Abbreviations:
AcOH Acetic acid
Con. Concentrated
D-DBTA (2S, 3S)-Dibenzoyl tartaric acid
DCM Dichloromethane
DIEA N,N-diisopropylethylamine
DMF N,N-dimethylformamide
DMF-DMA N,N-dimethylformamide dimethyl acetal
DSC Differential Scanning Calorimetry
DVS Dynamic Vapor Sorption
EtOAc Ethyl Acetate
EDCI 1-Ethyl-3-(3-dimethylaminopropyl)carbodiimide
GC Gas Chromatograph
GCMS Gas Chromatography-Mass Spectrometry
HATU 1-[Bis(dimethylamino)methylene]-1H-1,2,3-triazolo[4,5-b]pyridinium 3-oxide, hexafluorophosphate
HOAc Acetic Acid
HOBt Hydroxybenzotriazole
HPLC High Performance Liquid Chromatography
L-DBTA (2R, 3R)-Dibenzoyl tartaric acid
ACN Acetonitrile
MeOH Methanol
MeMgBr Methyl Magnesium Bromide
MsOH Methanesulfonic Acid
MTBE Methyl tertiary butyl ether
NLT not less than
NMP 1-Methyl-2-pyrrolidone
NMR Nuclear Magnetic Resonance
NMT not more than
Pd Palladium
RH Relative Humidity
RT or rt Room Temperature (20±2° C.)
TEA Triethylamine
TGA Thermo-gravimetric Analysis
THF Tetrahydrofuran
XRPD X-ray Powder Diffraction

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade.

The proton nuclear magnetic resonance ($^1$H-NMR) or carbon nuclear magnetic resonance ($^{13}$C-NMR) spectra was collected on a Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

The crystalline form is characterized by X-ray powder diffraction (XRPD) pattern method, which is conducted on a PANalytical Empyrean X-ray powder diffractometer with the XRPD parameters as follows:

| | Parameters for Reflection Mode |
|---|---|
| X-Ray wavelength | Cu, kα, Kα1 (Å): 1.540598, Kα2 (Å): 1.544426 |
| | Kα2/Kα1 intensity ratio: 0.50 |
| X-Ray tube setting | 45 kV, 40 mA |
| Divergence slit | Automatic |
| Scan mode | Continuous |
| Scan range (° 2TH) | 3°-40° |
| Step size (° 2TH) | 0.0130 |
| Scan speed (°/min) | About 10 |

The thermo-gravimetric analysis (TGA) curves are generated on a TA Q500/Q5000 TGA from TA Instruments. DSC and mDSC curves are generated on a TA Q2000 DSC from TA Instruments. Detailed parameters are listed below:

| Parameters | TGA | DSC | mDSC |
|---|---|---|---|
| Temperature range | RT-350° C. | RT-320° C. | 35-150 ° C. |
| Ramp rate | 10° C./min | 10° C./min | 3° C./min |
| Purge gas | $N_2$ | $N_2$ | $N_2$ |
| Pan Form | Aluminum, open | Aluminum, crimped | Aluminum, crimped |

The dynamic vapor sorption (DVS) plots are collected via a SMS (Surface Measurement Systems) DVS Intrinsic. The relative humidity at 25° C. is calibrated against deliquescence point of LiCl, $Mg(NO_3)_2$ and KCl. Detailed parameters are listed below:

| Parameters | DVS |
|---|---|
| Temperature | 25° C. |
| Sample size | 10~20 mg |
| Gas and flow rate | N2, 200 mL/min |
| dm/dt | 0.002%/min |
| Min dm/dt stability duration | 10 min |
| Max. equilibrium time | 180 min |
| RH range | 0% RH to 95% RH |
| RH step size | 10% RH from 0% RH to 90% RH |
| | 5% RH from 90% RH to 95% RH |

Example 1: Preparation of (S)-7-(1-(but-2-ynoyl) piperidin-4-yl)-2-(4-phenoxy phenyl)-4,5,6,7-tetra-hydropyrazolo[1,5-a]pyrimidine-3-carboxamide (Compound 1)

Step 1: Synthesis of BG-2

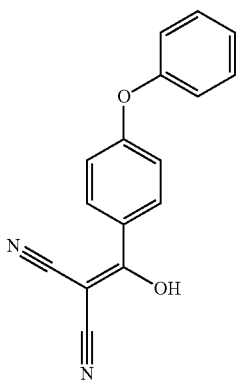

BG-2

Under nitrogen atmosphere, TEA (2.4 eq.) was added at 10° C. to a solution of EtOAc (5 v), HOBT (1.2 eq.), EDCI (1.2 eq.), 4-phenoxybenzoic acid (BG-1, 80 Kg, 1.0 eq.) and malononitrile (1.2 eq.). The mixture was then stirred at RT until the reaction was completed. The mixture was then centrifuged and the cake was washed with EtOAc. The filtrate was washed with aqueous $NaHCO_3$ twice and $NH_4Cl$. The organic phase was washed with 1.5 N $H_2SO_4$ twice and stirred. The mixture was concentrated, and precipitated from methanol and purified water. The solid was collected by centrifugation and then dried under vacuum to give 79.9 Kg of BG-2. $^1$H NMR (DMSO-$d_6$) δ 7.62 (d, J=8.6 Hz, 2H), 7.46-7.38 (m, 2H), 7.18 (t, J=7.4 Hz, 1H), 7.06 (d, J=8.0 Hz, 2H), 6.94 (d, J=8.6 Hz, 2H).

Step 2: Synthesis of BG-3

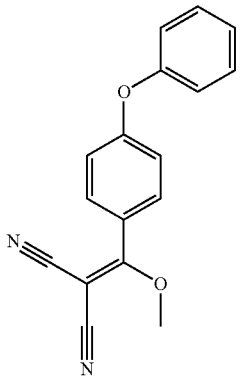

BG-3

Under nitrogen atmosphere, a solution of BG-2 (79.9 kg, 1.0 eq.) in ACN (5.0 v) was added into trimethoxymethane (12.0 v) at 85° C. The resultant mixture was stirred until the reaction was completed. The mixture was sampled for HPLC analysis, and concentrated under vacuum. The residue was precipitated from i-PrOH and hexane. The mixture was centrifuged, and the cake was washed with hexane and dried under vacuum. This gave 71.7 Kg of BG-3. $^1$H NMR (400 MHz, DMSO-$d_6$) δ 7.70 (d, J=8.4 Hz, 2H), 7.52-7.45 (m, 2H), 7.28 (t, J=7.6 Hz, 1H), 7.22-7.06 (m, 4H), 3.93 (s, 3H).

Step 3: Synthesis of BG-4

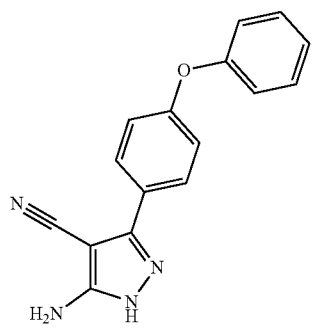

BG-4

Under nitrogen atmosphere, hydrazinium hydroxide (1.0 eq.) in ethanol (0.6 v) was charged dropwise to a solution of BG-3 (71.6 kg, 1.0 eq.) in ethanol (2.5 v) in the reactor below 15° C. The solution was heated to RT and stirred until the reaction was completed. Water (4.0 v) was added to the reactor. The solution was then cooled to 5° C., centrifuged and the cake was washed with water (1.0 v). The cake was dried under vacuum. This gave 66.9 Kg of BG-4. $^1$H NMR (DMSO-$d_6$) δ 12.11 (br s, 1H), 7.80 (d, J=8.8 Hz, 2H), 7.46-7.39 (m, 2H), 7.18 (t, J=7.6 Hz, 1H), 7.12-7.04 (m, 4H), 6.43 (br s, 2H).

Steps 4 to 6: Synthesis of BG-8

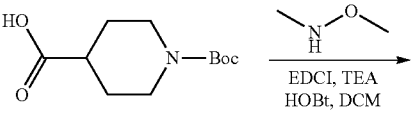

BG-5

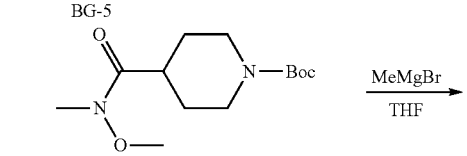

BG-6

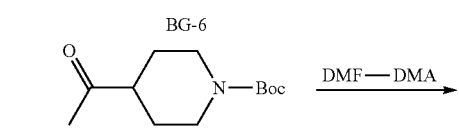

BG-7

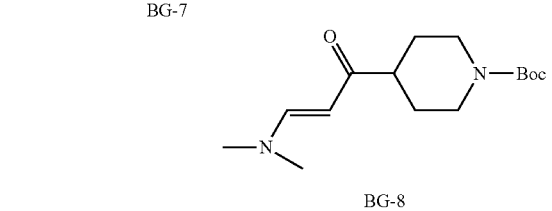

BG-8

To a mixture of DCM (8.0 v), BG-5 (80.0 Kg, 1.0 eq.), N,O-dimethylhydroxylamine hydrochloride (1.2 eq.), HOBt (1.2 eq.) and EDCI (1.2 eq.), TEA (2.6 eq.) was charged dropwise below 15° C. the mixture was stirred at RT until the reaction was completed, centrifuged and the cake was washed with DCM (1.0 v) twice. The filtrate was washed with 20% aqueous NH$_4$Cl (3*4.0 v). The filtrate was concentrated under vacuum to give the crude product BG-6, which was used in the next step without further purification. The residue was dissolved in toluene (5.0 v) and THF (1.0 v), cooled to 10° C., charged dropwise MeMgBr (1.4 eq.) at 10° C. and then stirred at RT until the reaction was completed. The solution was cooled below 10° C. Saturated aqueous NH$_4$Cl was charged dropwise below 10° C. The mixture was centrifuged, separated, filtrated, and the organic phase was washed with aqueous NaCl twice. The organic phase was concentrated to give the crude product, which was used in the next step without further purification. The residue in DMF (2.5 v) and DMF-DMA (2.5 v) was stirred at 110° C. until the reaction was completed. The reaction mixture was cooled, concentrated and then DCM was added. The final mixture was washed with saturated aqueous NH$_4$Cl. The organic layer was concentrated and precipitated by charging hexane. The mixture was centrifuged and the cake was collected. The cake was dried under vacuum. This gave 82.2 Kg of the desired product. $^1$H NMR (DMSO-d$_6$) δ 7.49 (d, J=12.6 Hz, 1H), 5.01 (d, J=12.6 Hz, 1H), 3.99-3.82 (m, 2H), 3.14-2.94 (m, 2H), 2.89-2.61 (m, 6H), 2.49-2.37 (m, 1H), 1.66-1.56 (m, 2H), 1.39 (s, 9H), 1.39-1.20 (m, 2H).

Step 7: Synthesis of BG-9

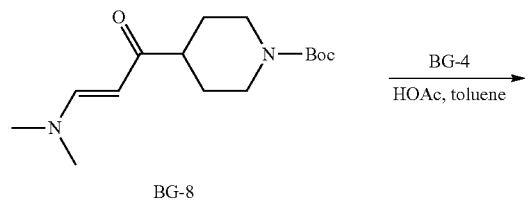

BG-8

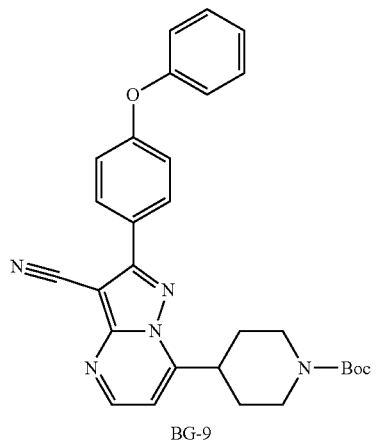

BG-9

Under nitrogen atmosphere, a mixture of toluene (8.0 v), AcOH (0.5 v), BG-8 (1.2 eq.) and BG-4 (66.9 Kg 1.0 eq.) was heated to 95° C. and stirred until the reaction was completed. The mixture was cooled, concentrated and precipitated from methanol. The mixture was centrifuged and the cake was washed with methanol. The cake was dried under vacuum. This gave 107.8 Kg of BG-9. $^1$H NMR (DMSO-d$_6$) δ 8.78 (d, J=4.6 Hz, 1H), 8.15-8.07 (m, 2H), 7.51-7.41 (m, 2H), 7.34 (d, J=4.6 Hz, 1H), 7.27-7.19 (m, 3H), 7.17-7.10 (m, 2H), 4.24-4.02 (m, 2H), 3.81-3.69 (m, 1H), 3.12-3.82 (m, 2H), 2.15-2.04 (m, 2H), 1.76-1.60 (m, 2H), 1.43 (s, 9H).

Step 8: Synthesis of BG-10

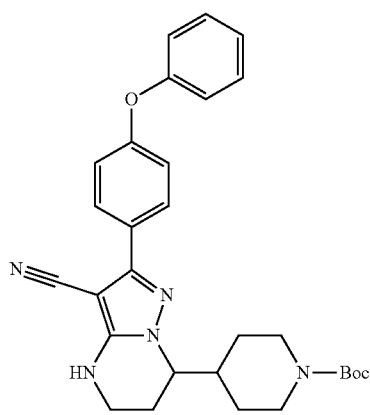

BG-10

To a mixture of THF (10.0 v), BG-9 (13.0 Kg, 1.0 eq.) and D-DBTA (1.0 eq.) under N$_2$ was charged Pd/C (10% w/w), hydrogen gas was introduced into the reactor and the hydrogen pressure was maintained to 1.8 MPa. The reactor was heated to 40° C. slowly and stirred until the reaction was completed. The mixture was then cooled, filtered, and the cake was washed with THF. The filtrate was collected, and concentrated under vacuum. DCM was added. The residue was washed with aq. NaHCO$_3$, concentrated and precipitated from MTBE and hexane, then centrifuged. The cake was collected and dried under vacuum to give the desired compound (yield: 94.8% and purity: 98.5%). $^1$H-NMR (DMSO-d$_6$) δ 7.82-7.76 (m, 2H), 7.56-7.51 (m, 1H), 7.45-7.37 (m, 2H), 7.21-7.14 (m, 1H), 7.12-7.03 (m, 4H), 4.09-3.91 (m, 3H), 3.30-3.22 (m, 2H), 2.82-2.55 (m, 2H), 2.18-1.99 (m, 2H), 1.98-1.86 (m, 1H), 1.69-1.58 (m, 1H), 1.56-1.45 (m, 1H), 1.38 (s, 9H), 1.32-1.13 (m, 2H).

Step 9: Synthesis of BG-11

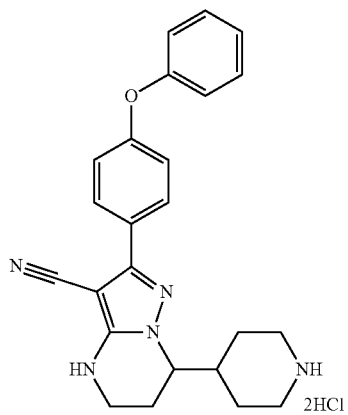

BG-11

To a solution of BG-10 (100.0 Kg 1.0 eq.) in DCM (6.0 v) was added dropwise HCl in EtOH (20.9% w/w, 2.0 v) under nitrogen atmosphere. The mixture is stirred until the reaction was completed. MTBE (4.0 v) was added to the solution, cooled. The cakes was collected by centrifugation and washed with hexane (2.0 V), then the cake was slurried in hexane (5 v), and centrifuged again. The cake was washed with hexane (2.0 V) and dried under vacuum. This gave 85.2 Kg of BG-11. $^1$H-NMR (DMSO-$d_6$) δ 9.25-8.85 (m, 2H), 7.84-7.70 (m, 2H), 7.47-7.37 (m, 2H), 7.18 (t, J=7.4 Hz, 1H), 7.12-7.03 (m, 4H), 5.73 (br s, 2H), 4.12-4.03 (m, 1H), 3.25-3.19 (m, 4H), 2.90-2.73 (m, 2H), 2.28-2.12 (m, 1H), 2.10-2.00 (m, 1H), 1.99-1.86 (m, 1H), 1.84-1.52 (m, 4H).

Step 10: Synthesis of BG-11A

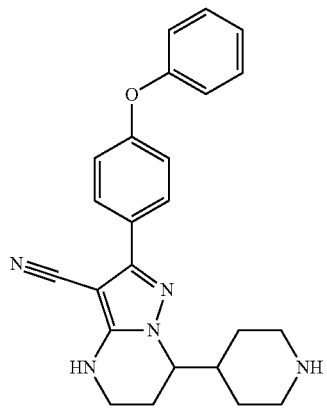

BG-11A

A mixture of BG-11 (85.0 Kg, 1.0 eq.) in water (6.0 v) and NaOH (3.0 eq.) was stirred until the reaction was completed at RT. The cake was collected and slurried in MTBE (6.0 v). The mixture was then centrifuged to collect the cake. The cake was dried under vacuum. This gave 71.3 Kg of BG-11A. $^1$H-NMR (DMSO-$d_6$) δ 7.82-7.74 (m, 2H), 7.54-7.49 (m, 1H), 7.45-7.38 (m, 2H), 7.21-7.14 (m, 1H), 7.12-7.04 (m, 4H), 4.03-3.95 (m, 1H), 3.29-3.21 (m, 2H), 3.00-2.87 (m, 2H), 2.46-2.31 (m, 2H), 2.11-1.83 (m, 3H), 1.58-1.12 (m, 4H).

Step 11: Synthesis of BG-11B

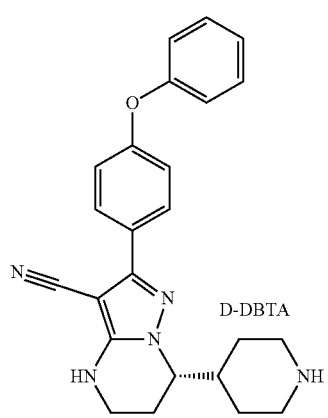

BG-11B

D-DBTA

A mixture of ethanol/water/acetic acid (7:3:1, 46 v) and BG-11A (30 kg, 1.0 eq.) in a reactor was heated to 70±5° C. under nitrogen atmosphere, then a solution of D-DBTA (1.20 eq.) in ethanol/water/acetic acid (7:3:1, 4 v) was added dropwise with the temperature not less than 65° C. The resulting solution was stirred for 16 hrs at 60-65° C., then cooled to RT. The solid was collected by centrifugation and washed with ethanol (2.0 v). The cake was slurried in the mixed solvent of ethanol/water/AcOH (7:3:1, 20 v) for 16 hrs at 55° C. and cooled to RT. The solid was collected by centrifugation, washed with ethanol (2.0 v). The cake was dried under vacuum (Yield: 37.9%) to give the desired product. $^1$H-NMR (DMSO-$d_6$) δ 8.76 (br s, 2H), 7.99-7.89 (m, 4H), 7.83-7.75 (m, 2H), 7.66-7.57 (m, 3H), 7.52-7.45 (m, 4H), 7.45-7.39 (m, 2H), 7.21-7.14 (m, 1H), 7.13-7.03 (m, 4H), 5.64 (s, 2H), 4.08-4.00 (m, 1H), 3.29-3.19 (m, 4H), 2.85-2.72 (m, 2H), 2.21-1.40 (m, 7H).

Step 12: Synthesis of BG-11C

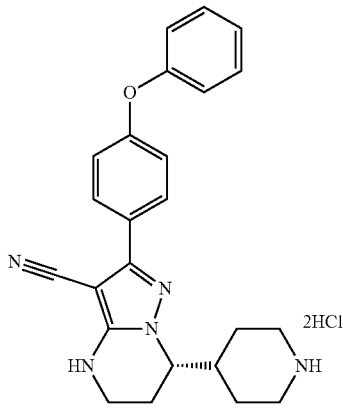

BG-11C

To a mixture of dichloromethane (15.0 v) and 20.0% aqueous KOH (3.0 v) was added batchwise BG-11B (48.0 kg, 1.0 eq.) under nitrogen atmosphere at RT. After the reaction was completed, the organic layer was collected and the water layer was extracted with dichloromethane (5.0 v). The organic layers were combined. Con. HCl (0.36 v) was added to the above organic layers at RT. The resulting mixture was stirred until the reaction was completed. The solid was collected by centrifugation and washed with dichloromethane (1.0 v). The collected solid was slurried with MTBE (6.0 v). The solid was collected by centrifugation and washed with MTBE (1.0 v), then was dried under vacuum. This gave 31.5 Kg product (Yield: 100%).

Step 12: Synthesis of BG-11D (Alternative Intermediate)

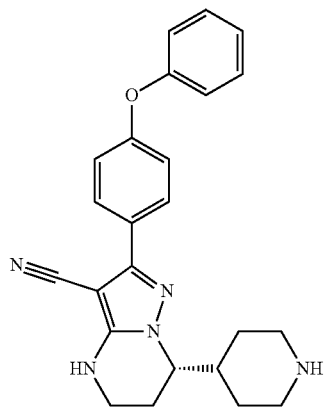
BG-11D

ACN (5.0 v), soft water (10.0 v), KOH (5.0 eq.) was charged to a reactor and stirred for at least 15 min. BG-11B (1.0 eq.) was charge to the reactor in portion-wise. The mixture was stirred until the reaction was completed. The cake was collected by centrifugation, slurried in ACN (1.0 v) and soft water (5.0 v), and dried under vacuum to give the product.

Step 13: Synthesis of BG-12

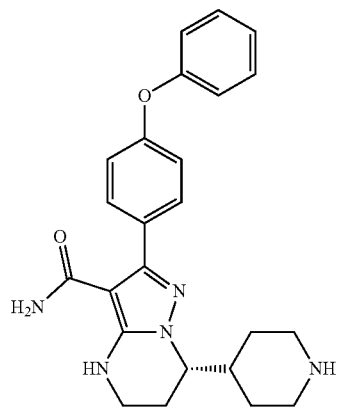
BG-12

A solution of BG-11C (15.0 Kg 1.0 eq.) in MsOH (2.5 v) was stirred at 85° C. under nitrogen atmosphere until the reaction was completed. After cooling to 5° C. purified water (4.0 v) was added dropwise to the system and kept the temperature not more than 35° C. (temperature increased obviously). The resulting solution was stirred for 16 hrs at 30° C., and then washed with DCM (2*3.0 v). The aqueous phase was collected. DCM (6.0 v) was added to the aqueous phase, the mixture was cooled to 5° C. The pH value was adjusted to 11-12 with 20% aqueous NaOH (temperature increased obviously) with stirring with the temperature not more than 30° C. The organic phase was separated and collected. The aqueous phase was extracted with DCM (3.0 v). The organic layers were combined and concentrated. MTBE (4.0 v) was added to the residue. The mixture was then concentrated and precipitated from n-heptane. The solid was collected by centrifugation and dried in a vacuum oven. This gave 12.55 Kg of BG-12 (Yield: 94.9%).
$^1$H-NMR (DMSO-$d_6$) δ 7.52-7.46 (m, 2H), 7.45-7.38 (m, 2H), 7.21-7.13 (m, 1H), 7.12-7.03 (m, 4H), 6.64 (s, 1H), 3.99-3.90 (m, 1H), 3.29-3.22 (m, 2H), 3.03-2.90 (m, 2H), 2.48-2.36 (m, 2H), 2.03 (dd, J=13.9, 5.6 Hz, 2H), 2.14-1.99 (m, 1H), 1.97-1.85 (m, 1H), 1.65-1.15 (m, 3H).

Step 14: Synthesis of BG-13

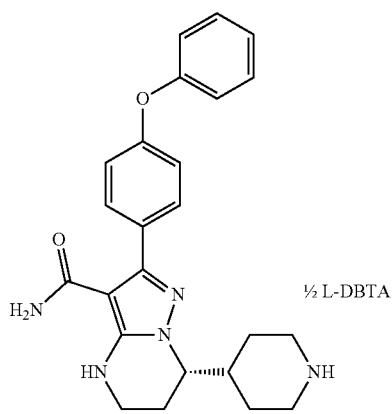
BG-13

A mixture of MeOH (13.5 v), purified water (4.5 v) and BG-12 (8.5 Kg, 1.0 eq.) in a reactor was heated to 50° C. under N$_2$ atmosphere. To the mixture was charged dropwise a solution of L-DBTA (0.7 eq.) in MeOH/purified water (1.5 v/0.5 v) while keeping the temperature at 50° C. After addition, the mixture was stirred for at least 2 hrs at 50° C., and then cooled to RT and stirred for at least 16 hrs at RT. The cake was collected by centrifugation and was washed with MeOH (2.0 v). The cake was dried in a vacuum oven. This gave 9.08 Kg of BG-13 (Yield: 74.8%).

Step 15: Synthesis of (S)-7-(1-(but-2-ynoyl)piperidin-4-yl)-2-(4-phenoxyphenyl)-4,5,6,7-tetrahydropyrazolo[1,5-a]pyrimidine-3-carboxamide (Compound 1)

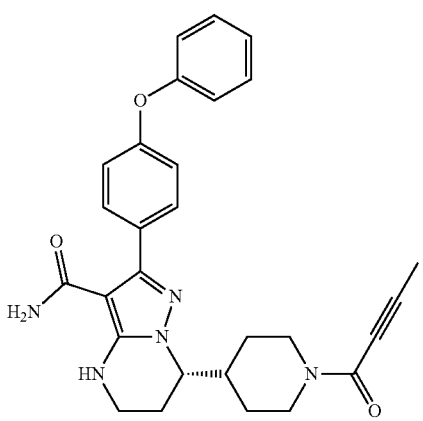
Compound 1

Under N$_2$ atmosphere, BG-13 (6.0 Kg; 1.0 eq) was stirred in charged DCM (30 L; 5.0 v) with the presence of 5% w/w aq. NaOH (0.48 Kg; 1.2 eq.) at around 30° C. until the reaction was completed. Separated and collected organic layer. The aqueous layer was further extracted with DCM. All organic layers were combined and washed with 15% brine for twice.

The organic layer was collected and concentrated under vacuum. To the residue was added but-2-ynoic acid (0.89 Kg; 1.05 eq.), HATU (4.21 Kg; 1.1 eq.) under N$_2$ atmosphere. The mixture was heated to 35~40° C. To the mixture was added dropwise TEA (3.05 Kg; 3.0 eq.; dissolved with DCM (12.0 L; 2.0 v)). The reaction was stirred until the reaction was completed.

The reaction system was concentrated under vacuum and swapped to DMF solution. Water (506.8 L; 40.0 v) was added dropwise to precipitate the solid. Centrifuged, collected the cake. The cake was dissolved in DCM and washed with 8% NaHCO$_3$ and 15% brine to remove DMF residue. The organic layer was concentrated and purified by silica gel (100-200 mesh column, eluted with heptane, followed by 1.2% w/w % methanol in DCM). The solution of Compound 1 was collected, concentrated and precipitate from DMF and water. The residual was centrifuged, and collected to give the crude product of Compound 1, which was confirmed to be amorphous.

Example 2: Preparation of Form A of Compound 1

The crude product of Compound 1 prepared in the above Example 1 was dissolved in 5.0 volumes of DCM. The resultant solution was washed with water (3.0 volumes*2). The organic phase was concentrated and swapped to EtOAc (no more than 2 volumes). The solution was further charged with EtOAc to 4.5 volumes. 27.5% w/w n-heptane in EtOAc (12.0 v) (the volume/volume ratio of EtOAc:n-heptane is about 2:1) was added dropwise to the system while the temperature was kept at RT. The system was then stirred for at least 24 hours at RT, centrifuged and collected the cake to obtain the resultant product in solid form.

Figure 2C:
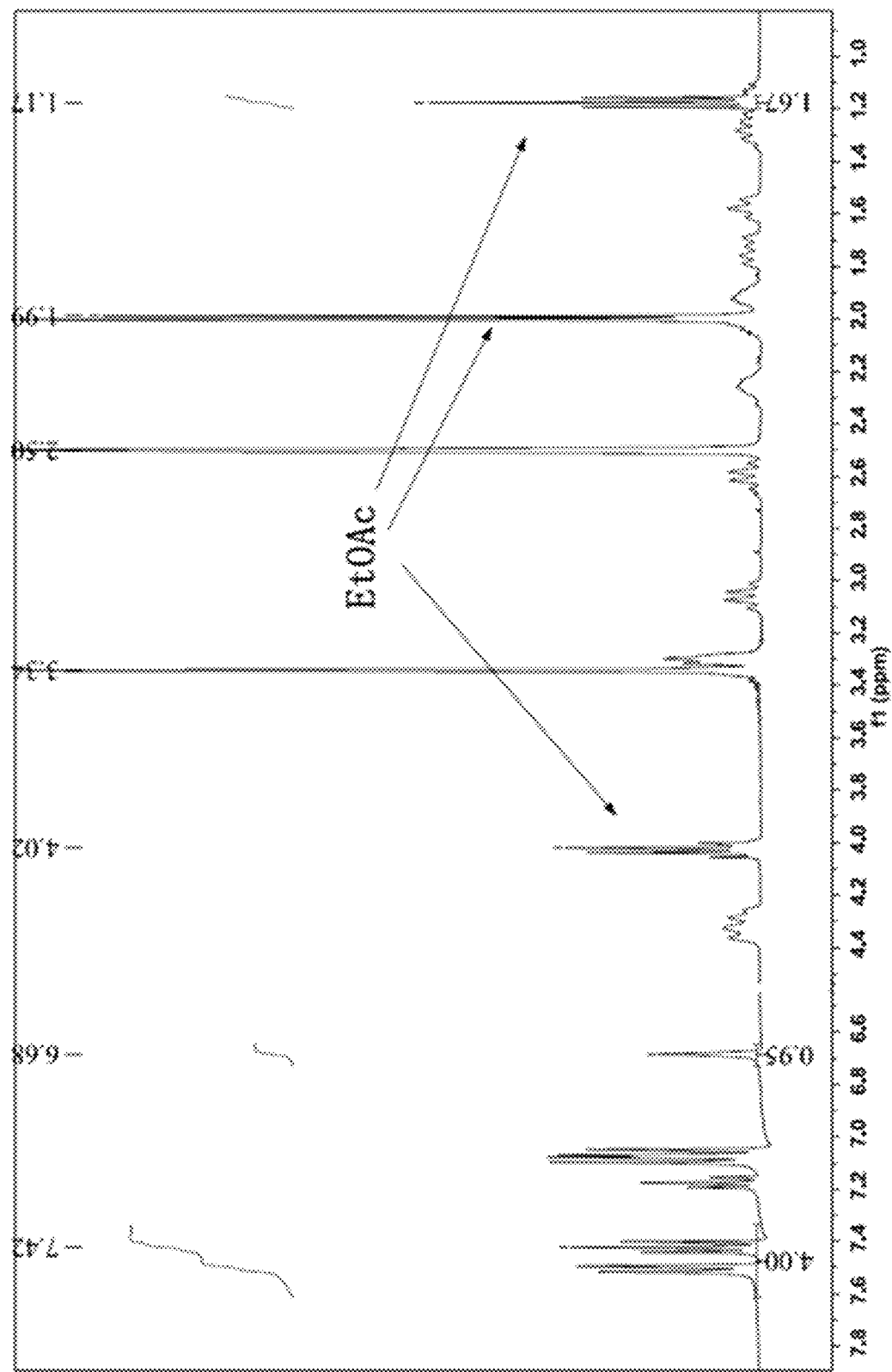
FIG. 2C shows the $^1$H-NMR of Form A (crystallization from EtOAc/n-heptane).

The solid was then subject to various characterizations including XRPD (FIG. 2A), TGA/DSC (FIG. 2B) and $^1$H NMR (FIG. 2C). $^1$H-NMR (DMSO-d$_6$) δ 7.56-7.47 (m, 2H), 7.46-7.37 (m, 2H), 7.22-7.13 (m, 1H), 7.13-7.02 (m, 4H), 6.67 (s, 1H), 4.45-4.20 (m, 2H), 4.09-3.95 (m, 1H), 3.33-3.26 (m, 2H), 3.17-2.95 (m, 1H), 2.70-2.52 (m, 1H), 2.36-2.18 (m, 1H), 2.00 (s, 3H), 2.12-1.85 (m, 2H), 1.83-1.66 (m, 1H), 1.65-1.51 (m, 1H), 1.37-1.06 (m, 2H).

Figure 2D:
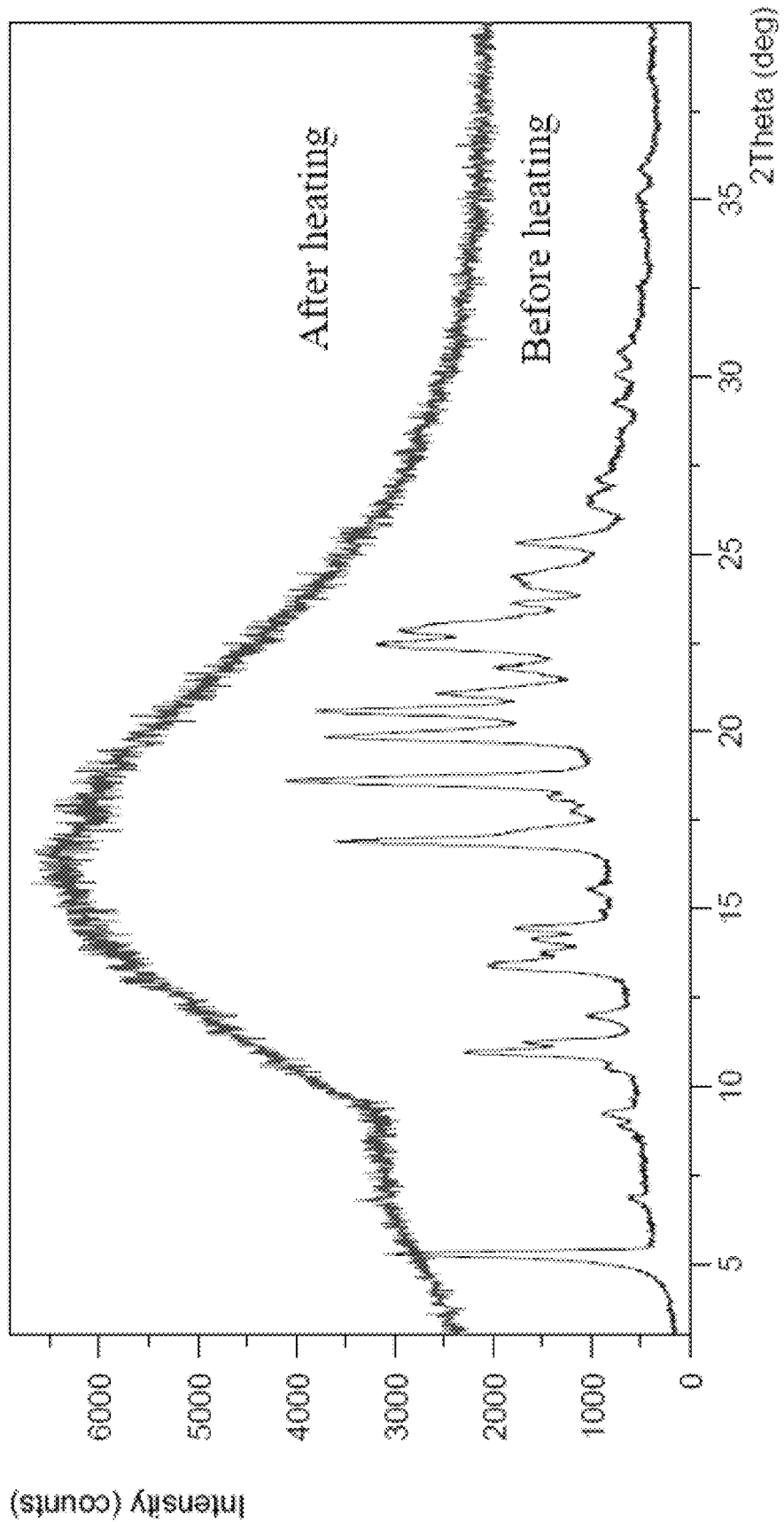
FIG. 2D shows XRPD overlay of Form A (crystallization from EtOAc/n-heptane) before and after heating.

The XRPD results found the resultant solid as a crystalline form (designated as Form A). The DSC result showed an endotherm at 87.5° C. before decomposition at 274.8° C. The TGA result showed a weight loss of 8.42% up to 150° C. After desolvation via heating in TGA, amorphous was produced (FIG. 2D). The $^1$H NMR result showed an EtOAc content of around 9.1%, consistent with TGA weight loss. The above $^1$H-NMR and TGA heating confirmed Form A as an EtOAc solvated crystalline form (sometimes referred to as Form A as an EtOAc solvate) wherein the molar ratio of Compound 1 and EtOAc is about 2:1.

Example 3: Preparation of Other Form A of Compound 1

About 15 mg of Form A as an EtOAc solvate as prepared in Example 2 was dissolved in the respective solvent (0.40 mL EtOH or 0.15 mL acetone) to obtain a saturated solution at room temperature. The resultant solution was magnetically stirred, then followed by addition of n-heptane as the anti-solvent (2.4 mL n-heptane for EtOH and 0.4 mL n-heptane for acetone, respectively) to induce precipitation. The respective precipitate was isolated for XRPD analysis.

Figure 3A:
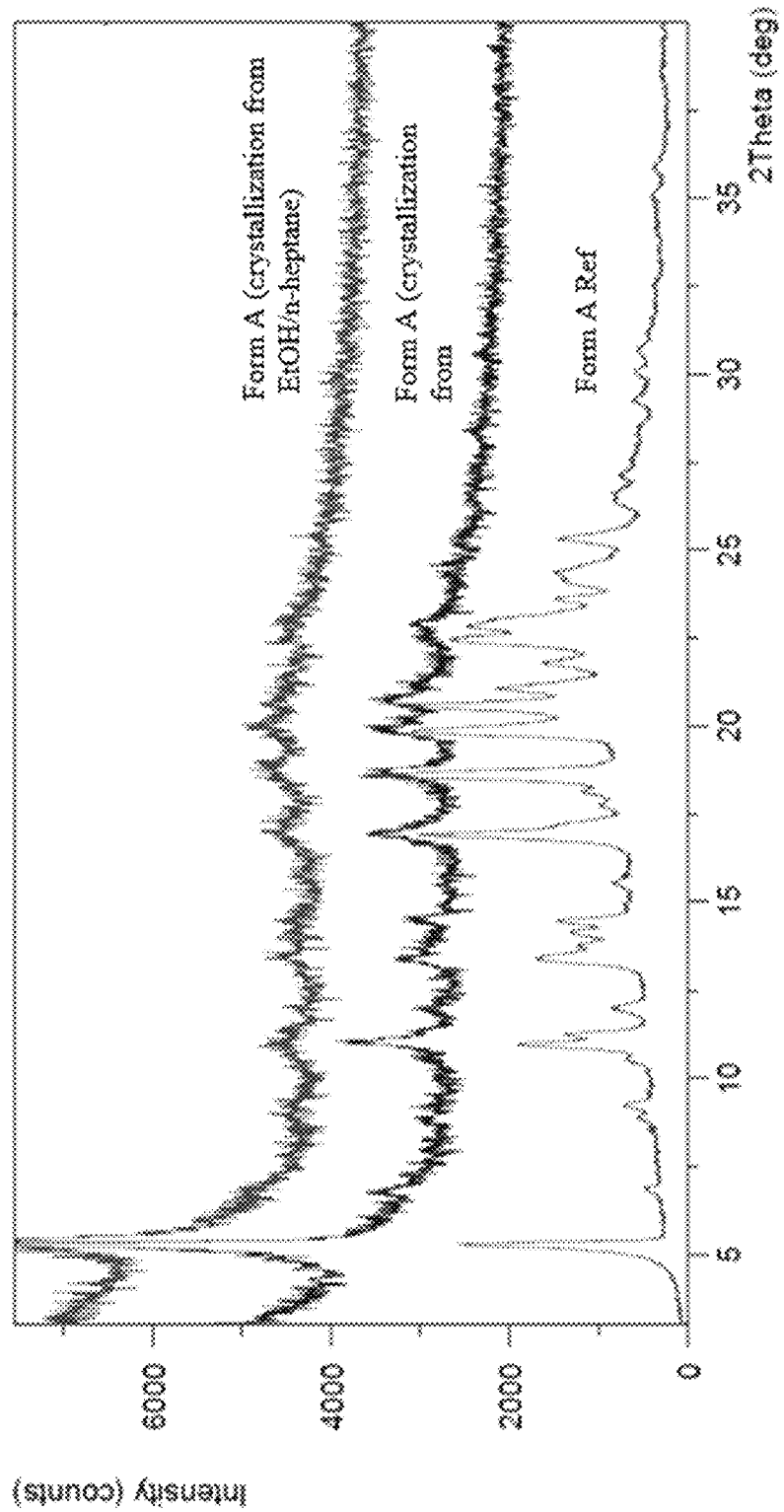
FIG. 3A shows the XRPD pattern of Form A (crystallization from EtOH/n-heptane) and Form A (crystallization from acetone/n-heptane).

The XRPD analysis found the product obtained from crystallization from EtOH/n-heptane and the product obtained from crystallization from acetone/n-heptane are crystalline; see FIG. 3A.

It is interesting to note that FIG. 3A shows that the XRPD patterns of Form A obtained from 2:1 EtOAc/n-heptane (v/v) in Example 2, Form A obtained from EtOH/n-heptane and Form A obtained from acetone/n-heptane comprise the diffraction peaks of substantially the same positions, although their relative intensities vary.

Figure 3B:
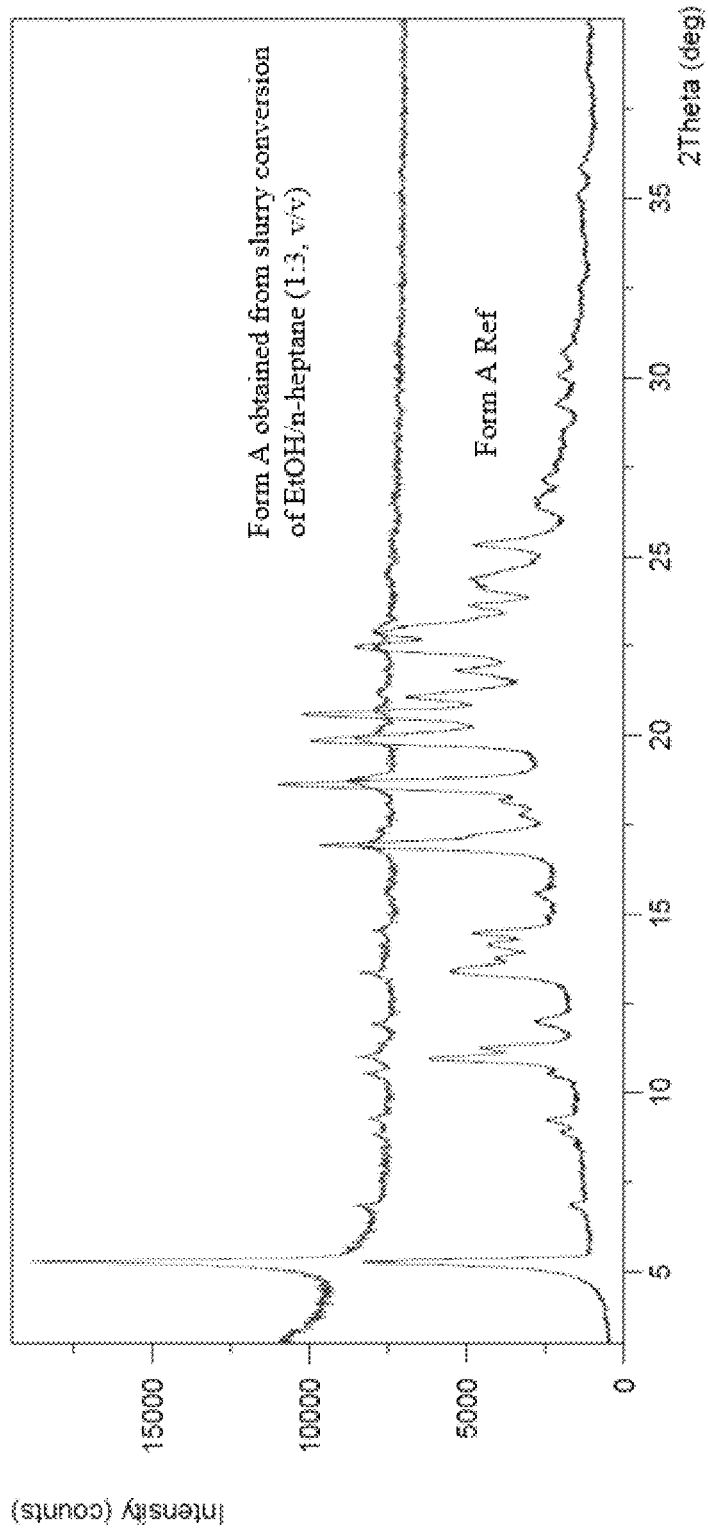
FIG. 3B shows the XRPD pattern of Form A obtained from slurry conversion of EtOH/n-heptane.
Figure 3C:
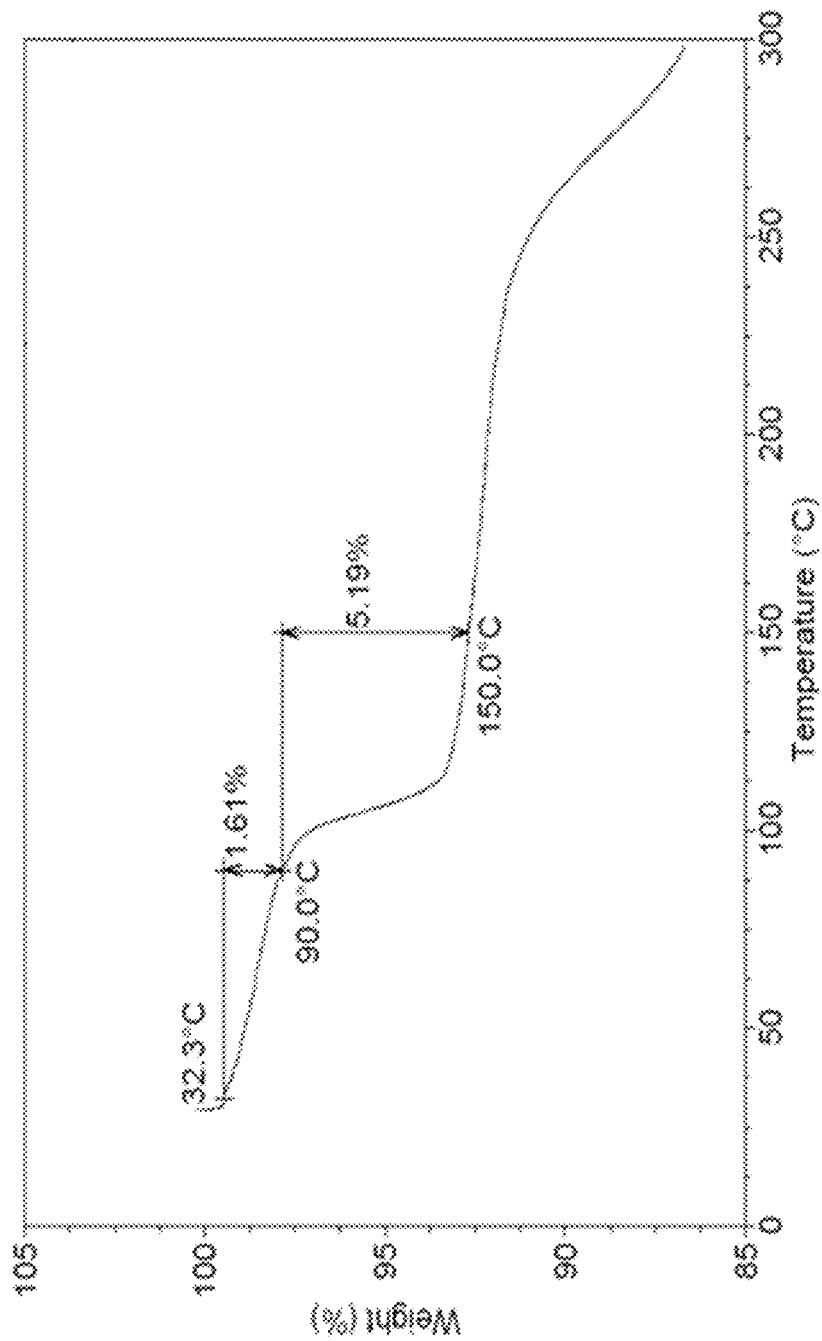
FIG. 3C shows the TGA curve of Form A obtained from slurry conversion of EtOH/n-heptane.
Figure 3D:
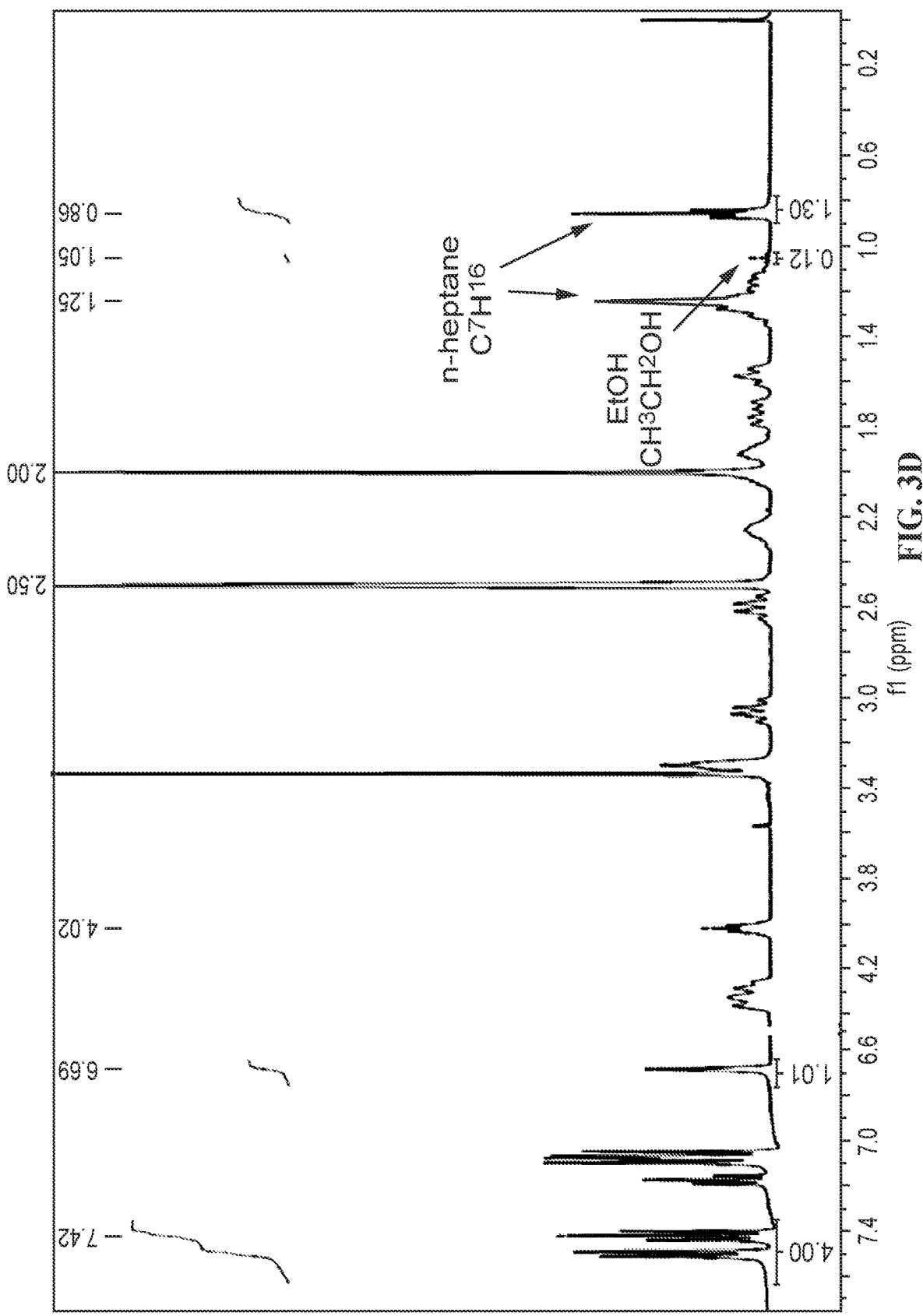
FIG. 3D shows the $^1$H-NMR of Form A obtained from slurry conversion of EtOH/n-heptane.
Figure 3E:
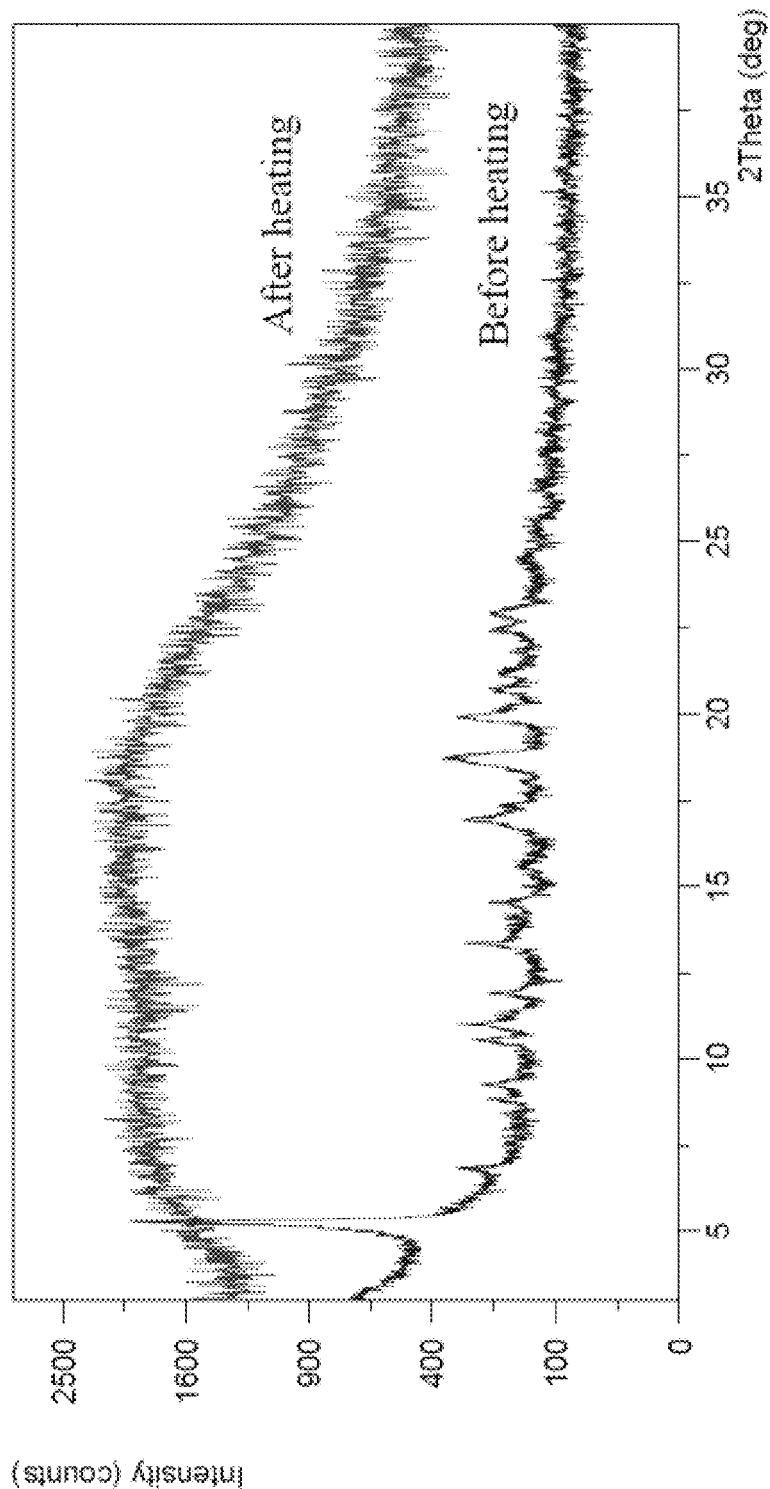
FIG. 3E shows the XRPD overlay of Form A obtained from slurry conversion of EtOH/n-heptane before and after heating.

Alternatively, Form A with increased crystallinity was prepared by slurry of amorphous in EtOH/n-heptane (1:3, v/v) at RT, as shown in FIG. 3B (also confirmed the crystalline structure of Form A, referred to as Form A obtained from slurry conversion of EtOH/n-heptane). The TGA curve of Form A obtained from slurry conversion of EtOH/n-heptane in FIG. 3C showed a two-step loss of 6.8% up to 150° C. The $^1$H-NMR result of Form A obtained from slurry conversion of EtOH/n-heptane in FIG. 3D showed an EtOH content of 0.4% and n-heptane content of 4.4% without EtOAc residual. After desolvation via TGA heating, amorphous was also produced as shown in FIG. 3E.

The $^1$H-NMR and TGA heating for Form A obtained from slurry conversion from EtOH/n-heptane also confirmed the resultant Form A as a solvated crystalline form, in particular, Form A as a hetero-solvate of EtOH and n-heptane.

Example 4: Preparation Crystalline Form B of Compound 1

To the reactor was charged Form A of Compound 1 (1.0 eq.) prepared in the above Example 2, EtOAc (7.5 v) and n-heptane (7.5 v). The mixture was heated to 55-60° C. and stirred at least 72 h. The mixture was then cooled to 10-15° C. and stirred for at least 15 min. The cake was collected after centrifugation and washed with n-heptane to give a solid (yield 52.2%).

Figure 4C:
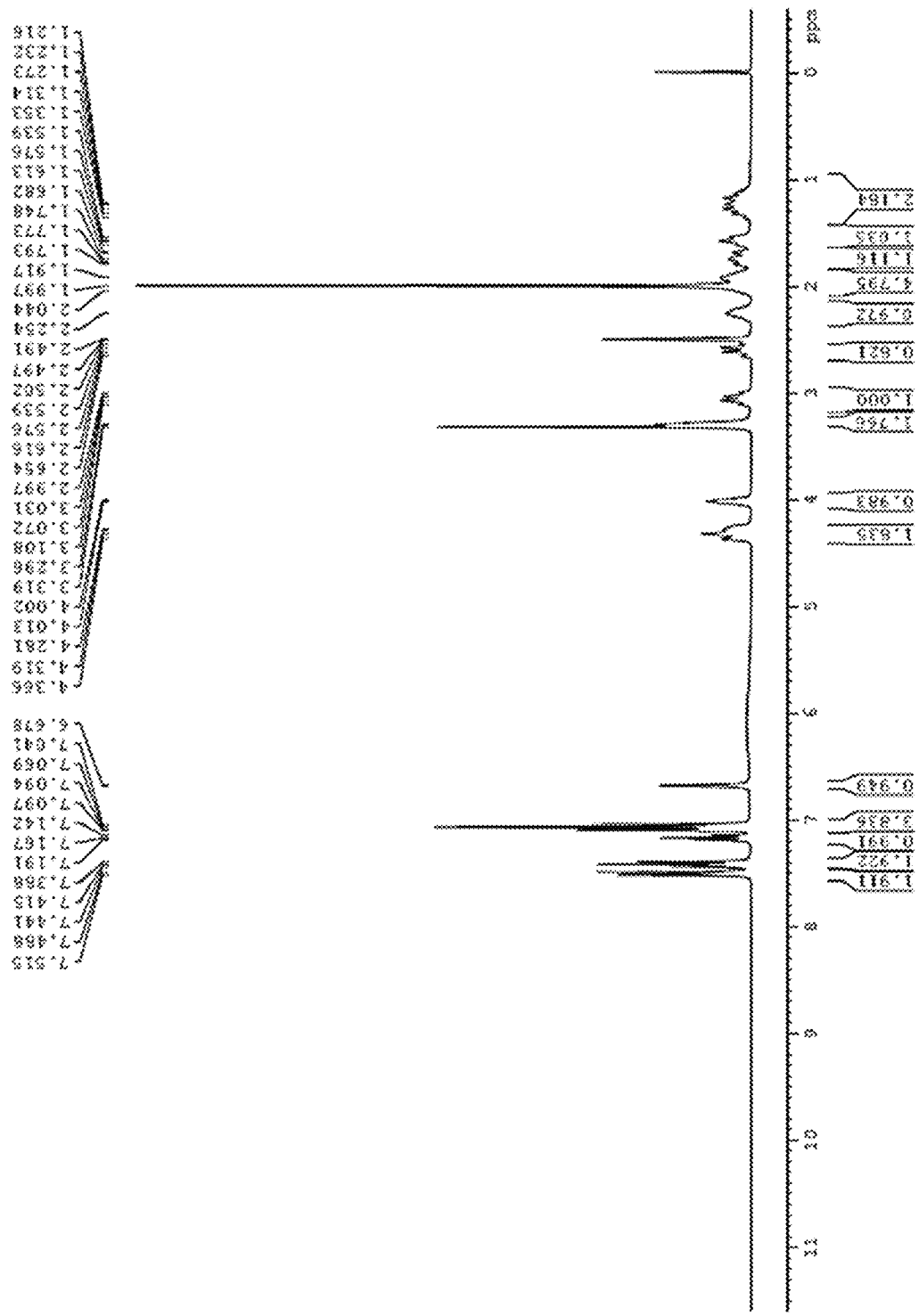
FIG. 4C shows the $^1$H-NMR of Crystalline Form B.
Figure 4D:
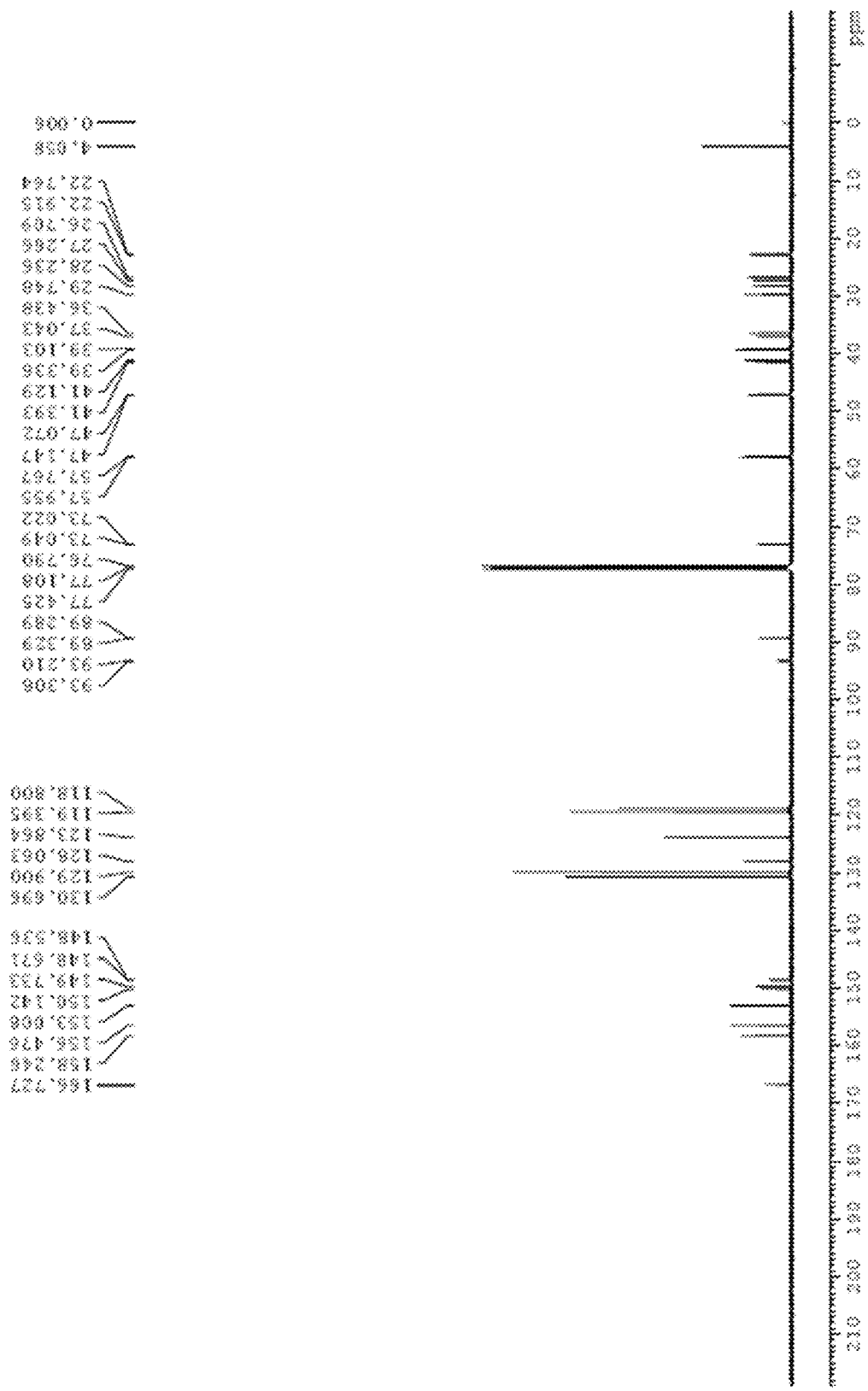
FIG. 4D shows the $^{13}$C-NMR of Crystalline Form B.

The resultant solid was then subject to various characterizations including XRPD (FIG. 4A), TGA/DSC (FIG. 4B), $^1$H NMR (FIG. 4C) and $^{13}$C-NMR (DMSO-d$_6$) (FIG. 4D). $^1$H-NMR (DMSO-d$_6$) δ 7.56-7.47 (m, 2H), 7.46-7.37 (m, 2H), 7.22-7.13 (m, 1H), 7.13-7.02 (m, 4H), 6.67 (s, 1H), 4.45-4.20 (m, 2H), 4.09-3.95 (m, 1H), 3.33-3.26 (m, 2H), 3.17-2.95 (m, 1H), 2.70-2.52 (m, 1H), 2.36-2.18 (m, 1H), 2.00 (s, 3H), 2.12-1.85 (m, 2H), 1.83-1.66 (m, 1H), 1.65-1.51 (m, 1H), 1.37-1.06 (m, 2H).

The XRPD result found the resultant solid as a crystalline form different from the above Form A (designated as Form B). The DSC result showed a neat melting endotherm at 153.9° C. (onset temperature). The TGA result showed a two-step weight loss of 2.3% up to 140° C., indicating Form B is anhydrous non-solvated. The $^1$H-NMR showed no solvent residual EtOAc that appeared in Form A, which is consistent with the TGA result.

Example 5: Preparation of Crystalline Form B of Compound 1

Example 5A: Preparation from Form A of Compound 1

250 mg of Form A of Compound 1 prepared in the above Example 2 was charged into a 20-mL glass vial. 2.0 mL of THF was added into the vial and stirred at RT until all solids were dissolved. 2.0 mL of n-heptane was added to induce precipitate and the mixture was equilibrated at RT for 1 hr. About 4 mg of Form B prepared in the above Example 4 was added as seed and the mixture was stirred at RT for 1.5 hrs. Additional 4.0 mL of n-heptane was added to induce more solids and transfer to 50° C. agitation for 1 hr. About 4 mg of Form B prepared in the above Example 4 was added again as seed and the mixture was stirred at 50° C. for 22 hrs. The cake was then collected by vacuum filter and was dried at 50° C. for 16 hrs to obtain the solid (169.5 mg, yield of ~74%).

Example 5B: Preparation from Compound 1 in Amorphous Form 250 mg of Compound 1 in amorphous form prepared in Example 1 was added into a 20-mL glass vial. 1.0 mL of THF was added into the vial and stirred at RT until all solids were dissolved. 1.0 mL of n-heptane was added to induce precipitate. The mixture was equilibrated at RT for 1 hr. About 4 mg of Form B of Compound 1 prepared in the above Example 4 was added as seed and the mixture was stirred at RT for 1.5 hrs. Additional 2.0 mL of n-heptane was added to induce more solids. About 4 mg of Form B of Compound 1 prepared in the above Example 4 was added again as seed and the mixture was stirred at 50° C. for 22 hrs. The cake was collected by vacuum filter and dried at 50° C. for 16 hrs to obtain the solid (168.2 mg, yield of ~72%).

The XRPD analysis of the resultant solids of Examples 5A and 5B confirmed that the solids of Example 5A and 5B are Form B as their XRPD patterns (FIG. 4G) are consistent with that of Example 4 (FIG. 4A).

Example 6: Slurry Conversion from Compound 1 of Form A or Amorphous Form at Different Temperatures Slurry conversion experiments were conducted in different solvent systems at different temperature with Compound 1 in Form A or Compound 1 in amorphous form as the starting material.

Example 6A: Slurry Conversion from Form A at 5° C.

Slurry conversion experiments were conducted in different solvent systems at 5° C. by suspending about 15 mg of Form A prepared in the above Example 2 with 0.3 mL of solvent in a 1.5-mL glass vial. After stirring for about 6 days, the suspensions were isolated by centrifuge, and the solids were analyzed by XRPD. Results summarized in Table 3 showed Form A was obtained from some solvent systems at 5° C., as the XRPD patterns of the resultant crystalline forms are consistent with Form A as an EtOAc solvate in Example 2.

TABLE 3

Summary of slurry conversion experiments at 5° C.

| No. | Solvent (v/v) | Solid Form |
|---|---|---|
| A01 | Isopropyl acetate | Form A |
| A02 | Isopropyl alcohol | N/A |
| A03 | $H_2O$ | Form A |
| A04 | MTBE | Form A |
| A05 | n-heptane | Form A |

TABLE 3-continued

Summary of slurry conversion experiments at 5° C.

| No. | Solvent (v/v) | Solid Form |
|---|---|---|
| A06 | MeOH/$H_2O$ (1:5) | amorphous |
| A07 | ACN/$H_2O$ (1:5) | N/A |
| A08 | Acetone/$H_2O$ (1:5) | amorphous |
| A09 | Acetic acid/$H_2O$ (1:5) | N/A |
| A10 | NMP/$H_2O$ (1:5) | Form A |
| A11 | THF/n-heptane(1:5) | Form A |
| A12 | 1,4-Dioxane/n-heptane(1:5) | Form A |
| A13 | EtOAc/n-heptane(1:5) | Form A |
| A14 | DCM/MTBE(1:5) | Form A |

N/A: no solid was obtained.

Example 6B: Slurry Conversion from Form A at RT

Slurry conversion experiments were conducted in different solvent systems at RT by suspending about 15 mg of Form A with 0.5 mL of solvent in a 1.5-mL glass vial. After stirring for about 6 days, the suspensions were isolated by centrifuge, and the solids were analyzed by XRPD. Results summarized in Table 4 showed Form A was obtained from some solvent systems at RT, as the XRPD patterns of the resultant crystalline forms are consistent with Form A as an EtOAc solvate in Example 2.

TABLE 4

Summary of slurry conversion experiments at RT

| No. | Solvent (v/v) | Solid Form |
|---|---|---|
| B01 | Isopropyl acetate | Form A |
| B02 | Isopropyl alcohol | N/A |
| B03 | $H_2O$ | amorphous |
| B04 | MTBE | Form A |
| B05 | MeOH/$H_2O$(1:5) | amorphous |
| B06 | ACN/$H_2O$ (1:5) | N/A |
| B07 | Acetone/$H_2O$ (1:5) | N/A |
| B08 | Acetic acid/$H_2O$ (1:5) | N/A |
| B09 | NMP/$H_2O$ (1:5) | amorphous |
| B10 | THF/n-heptane(1:5) | Form A |
| B11 | 1,4-dioxane/n-heptane(1:5) | Form A |
| B12 | EtOAc/n-heptane(1:5) | Form A |
| B13 | $CHCl_3$/MTBE(1:5) | Form A |

N/A: no solid was obtained.

Example 6C: Slurry Conversion from Compound 1 in Amorphous Form

Slurry conversion experiments were conducted in varying solvent systems at RT and 50° C. using Compound 1 in amorphous form as the staring material. A certain amount (10-25 mg) of Compound 1 in amorphous form was added into the corresponding solvent. The resultant mixture was stirred at the desired temperature for 2 hrs. About 2 mg of Form B was added as seed. The mixture was stirred for another 60 hrs at the same desired temperature. The resultant solid was collected for XRPD analysis.

TABLE 5

Summary of slurry conversion experiments starting from Compound 1 in amorphous form

| No. | Solvent (v/v) | Condition | Solid Form |
|---|---|---|---|
| C01 | EtOAc/n-hexane (1:1) | RT, | Form A + B |
| C02 | EtOAc/n-hexane (1:3) | Form B seeded | Form B |

TABLE 5-continued

Summary of slurry conversion experiments starting
from Compound 1 in amorphous form

| No. | Solvent (v/v) | Condition | Solid Form |
|---|---|---|---|
| C03 | EtOH/n-heptane (1:3) | | Form A |
| C04 | Acetone/n-heptane (1:3) | | Form A + B |
| C05 | THF/n-heptane (1:3) | | Form A + B |
| C06 | CHCl$_3$/n-heptane (1:3) | | Gel |
| C07 | EtOAc/n-hexane (1:1) | 50° C., | Form B |
| C08 | EtOAc/n-hexane (1:3) | Form B seeded | Form B |
| C09 | EtOH/n-heptane (1:3) | | Form A |
| C10 | Acetone/n-heptane (1:3) | | Form B |
| C11 | THF/n-heptane (1:3) | | Form B |
| C12 | CHCl$_3$/n-heptane (1:3) | | Form B |
| C13 | EtOH/H$_2$O (1:5) | | Gel |
| C14 | THF/H$_2$O (1:5) | | Gel |
| C15 | CHCl$_3$/MTBE (1:5) | | Form B |
| C16 | Acetone/MTBE (1:5) | | Form B |

Figure 5A:
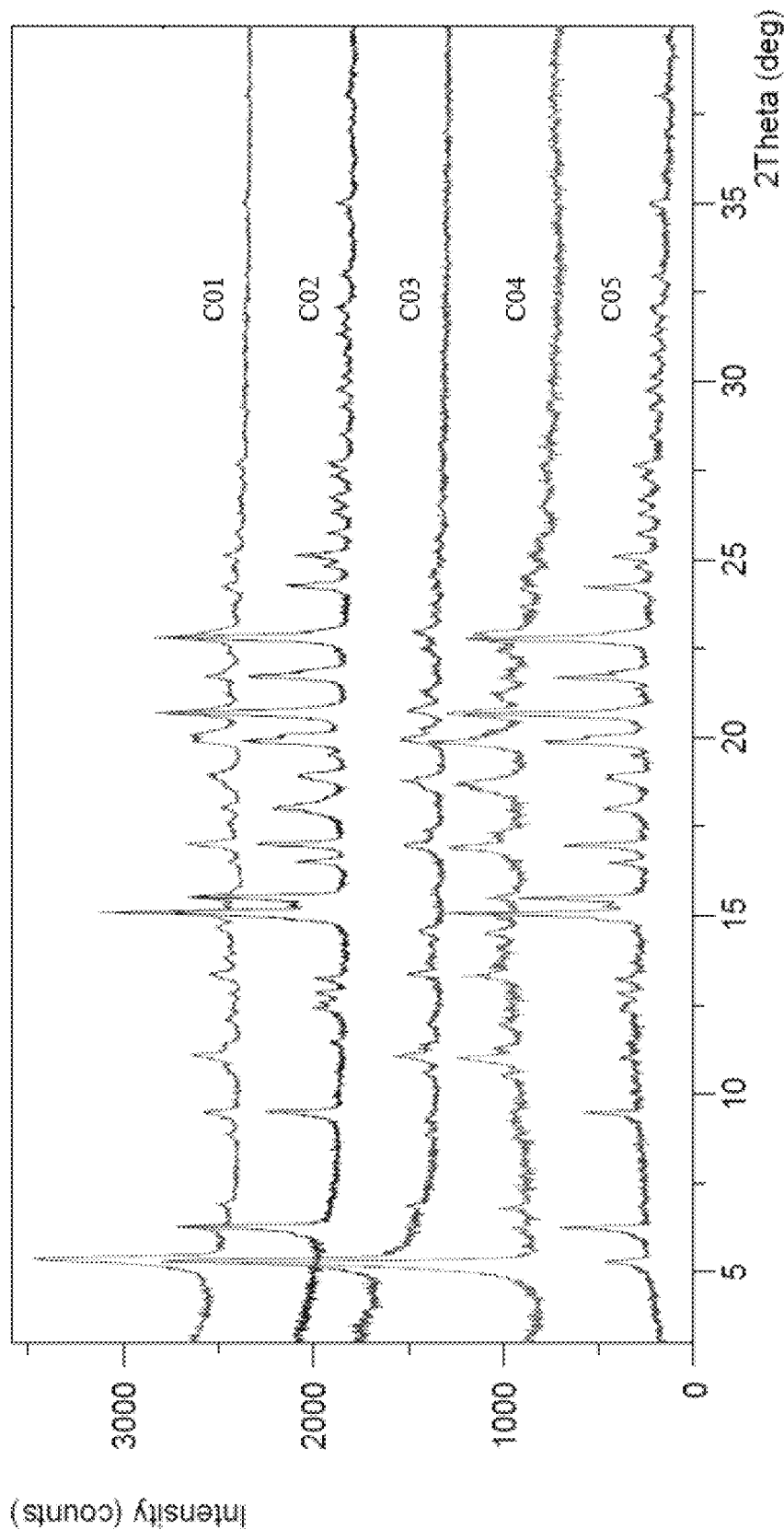
FIG. 5A shows XRPD overlay for slurry at RT starting from amorphous Compound 1.
Figure 5B:
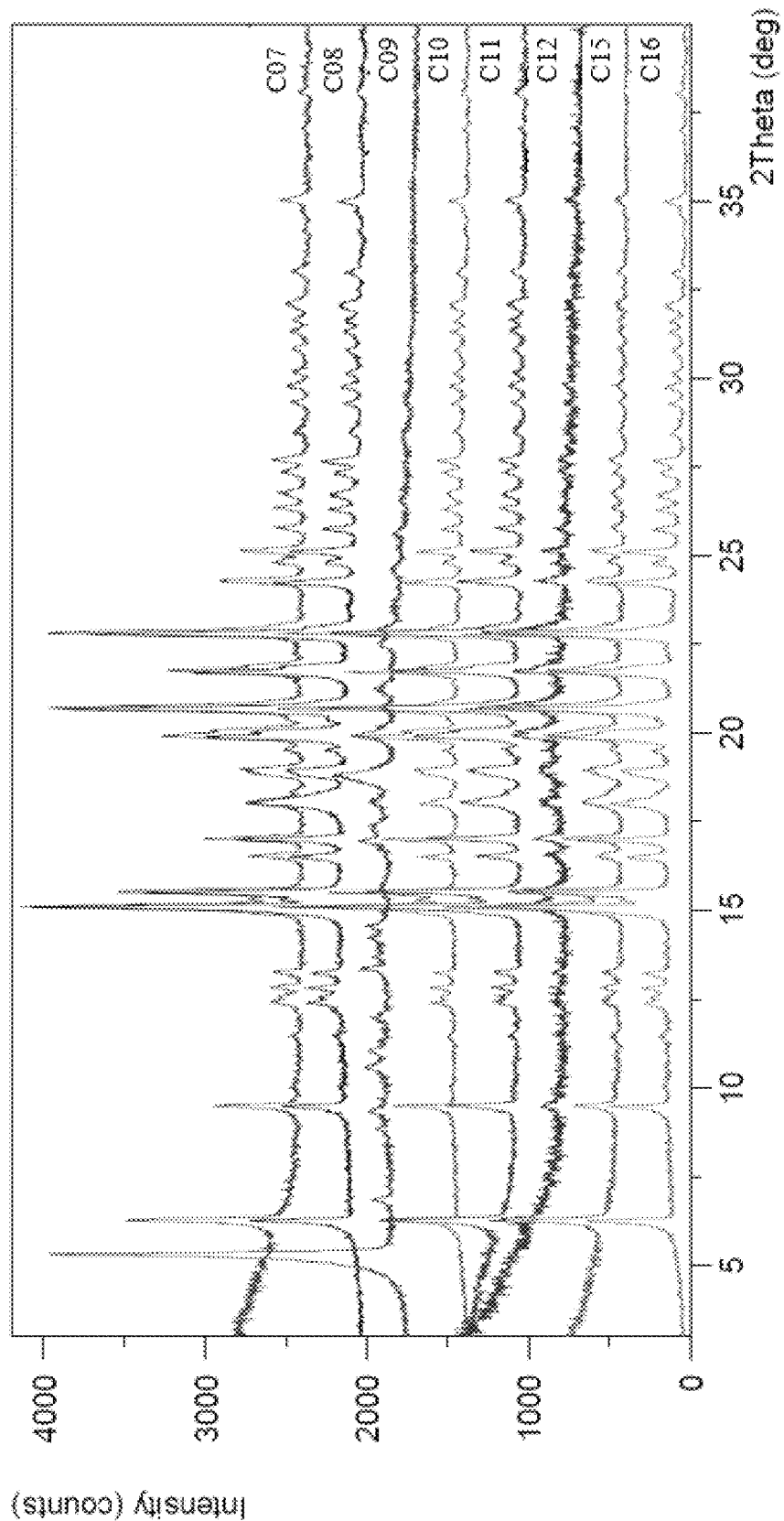
FIG. 5B shows XRPD overlay for slurry at 50° C. starting from amorphous Compound 1.

The above table showed that Compound 1 in amorphous form can be converted into Form A, Form B or mixture thereof in slurry conversion conducted in varying solvent systems at room temperature (20±2° C.) and 50° C. followed by addition of Form B seeds. FIG. 5A and FIG. 5B confirmed the crystalline forms of the resultant solids obtained at different temperatures.

Example 6D: Thermodynamic Stability in Current Process Solvent Systems

About 500 mg, 300 mg, 100 mg and 70 mg of Compound 1 in amorphous form of Example 1 were weighted into each 3-mL glass vial. 1.0 mL of EtOAc/n-heptane (solvent ratio: 1/0*, 3/1, 1/1, 1/3) was added into each of the above vial sequentially. The mixtures were stirred at 50° C. for 2 hrs to get saturated solutions. Equally, about 10 mg of Compound 1 in Form A of Example 2 and Form B of Example 4 in an approximate mass ratio of 1:1 were added into each 1.5 mL glass vial. 0.3 mL of each of the above corresponding saturated solution (equilibrated at 50° C.) was added into each of the above 1.5 mL glass vial and stirred at desired temperature. Samples were collected after 3, 6 and 13 days for XRPD characterization until form conversion was observed. (*Clear solution in pure EtOAc was obtained due to not enough Compound 1 in amorphous form)

Figure 5C:
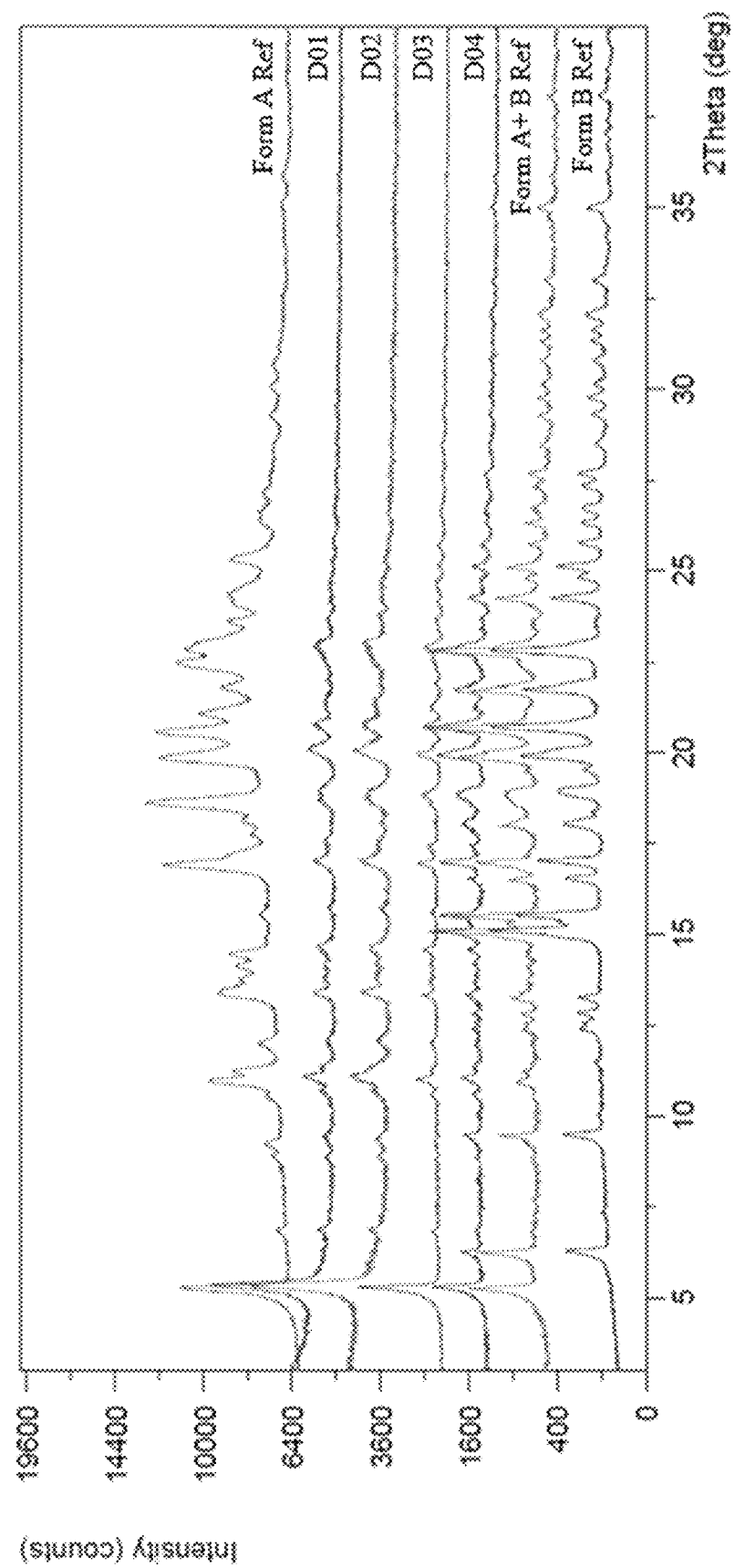
FIG. 5C shows XRPD overlay for competitive slurry of Form A and B at 10° C.
Figure 5D:
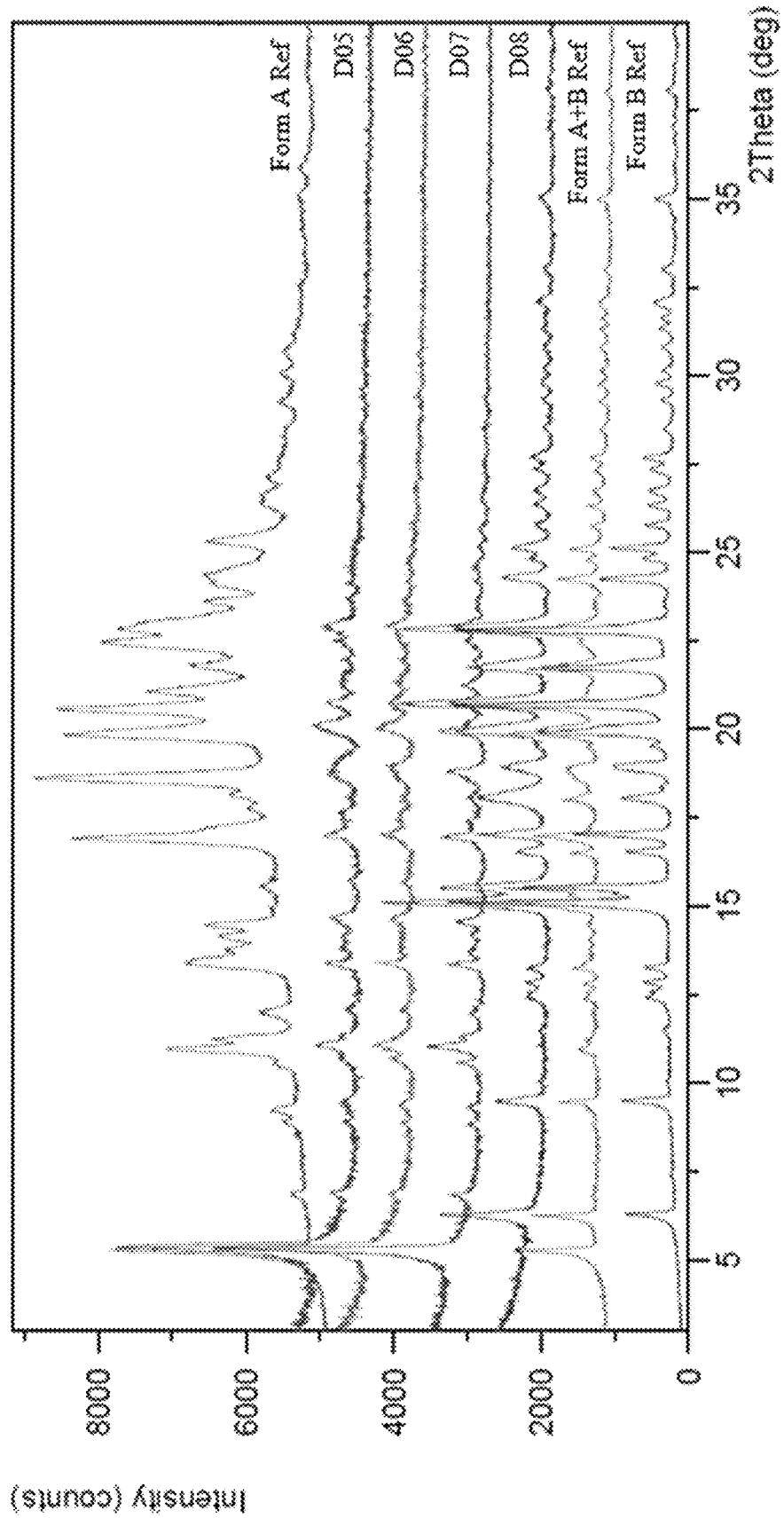
FIG. 5D shows XRPD overlay for competitive slurry of Form A and B at RT.
Figure 5E:
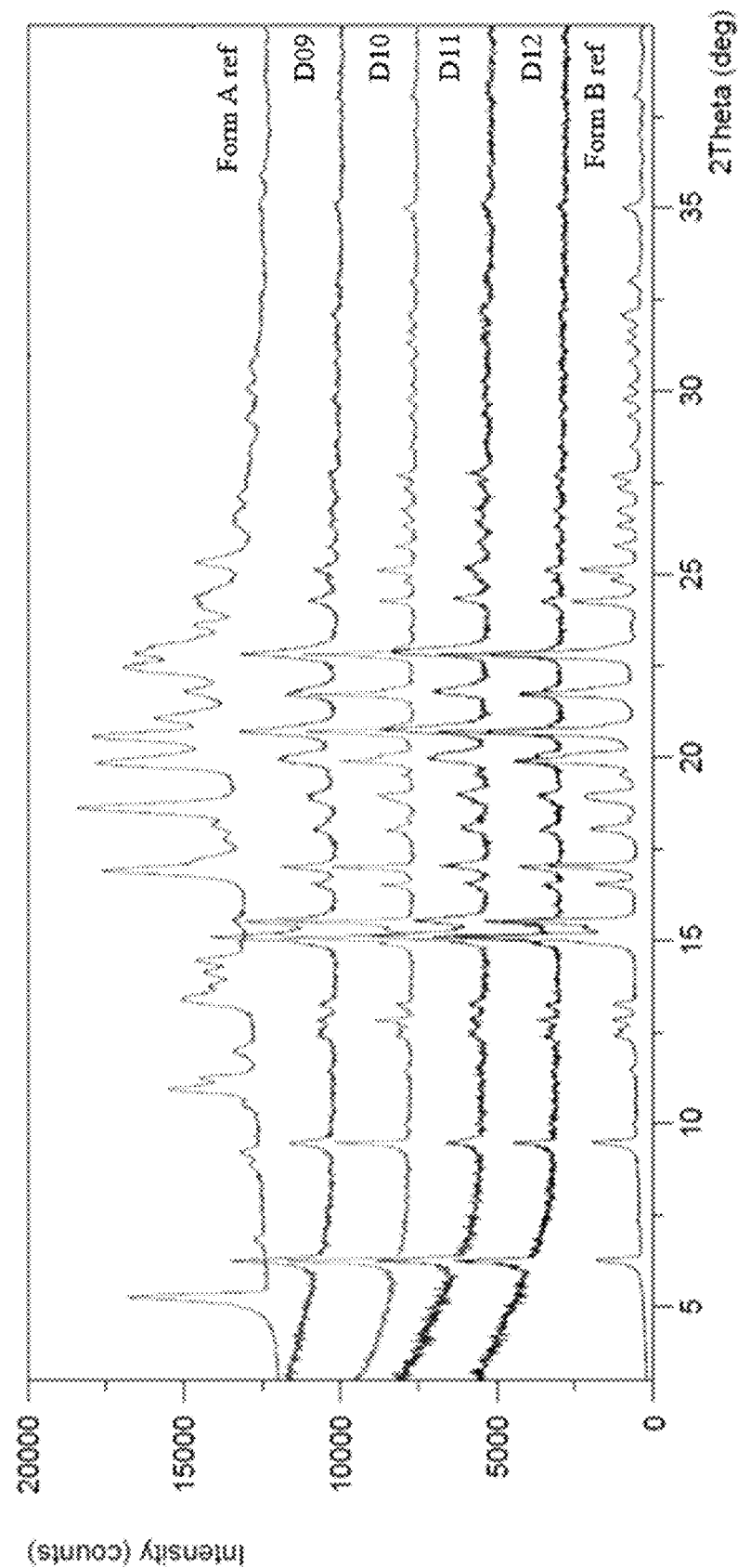
FIG. 5E shows XRPD overlay for competitive slurry of Form A and B at 50° C.

Results were summarized in Table 6, FIGS. 5C, 5D and 5E.

TABLE 6

Summary of thermodynamic stability
in current process solvent systems

| No. | Solvent (v/v) | Condition | Solid Form |
|---|---|---|---|
| D01 | EtOAc | 10° C. | Form A |
| D02 | EtOAc/n-heptane (3:1) | | Form A |
| D03 | EtOAc/n-heptane (1:1) | | Form A |
| D04 | EtOAc/n-heptane (1:3) | | Form A + B |
| D05 | EtOAc | RT | Form A |
| D06 | EtOAc/n-heptane (3:1) | | Form A |
| D07 | EtOAc/n-heptane (1:1) | | Form A |
| D08 | EtOAc/n-heptane (1:3) | | Form A* + B |
| D09 | EtOAc | 50° C. | Form B |
| D10 | EtOAc/n-heptane (3:1) | | Form B |
| D11 | EtOAc/n-heptane (1:1) | | Form B |
| D12 | EtOAc/n-heptane (1:3) | | Form B |

*Small part of Form A was observed, indicating Form B is thermodynamically more stable under this condition.

In the above competitive slurry turnover experiments, Form A and Form B were exposed under EtOAc/n-heptane system with a series of solvent ratios and temperatures (10° C., 20±2° C., and 50° C.), which indicated that Form B is thermodynamically more stable than Form A at 50° C., and at room temperature with a volume fraction of EtOAc decreased to 0.25. Concluded from Example 6, anhydrous non-solvated Form B tends to be the stable crystalline form under conditions with elevated temperature, decreased EtOAc content, seed loading and extended equilibration time.

Example 7: Hygroscopic Test

Figure 4E:
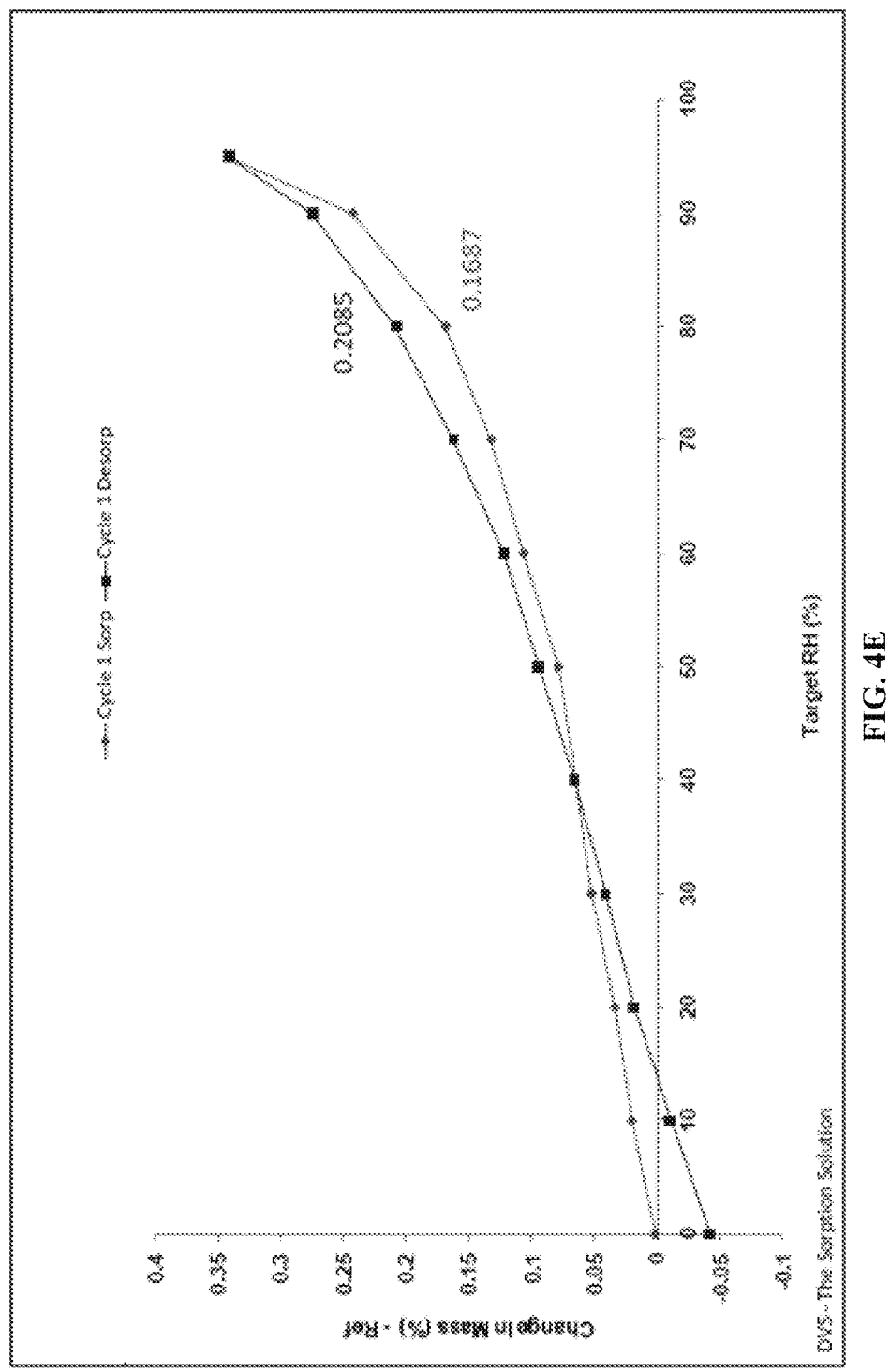
FIG. 4E shows DVS plot of Crystalline Form B.
Figure 4F:
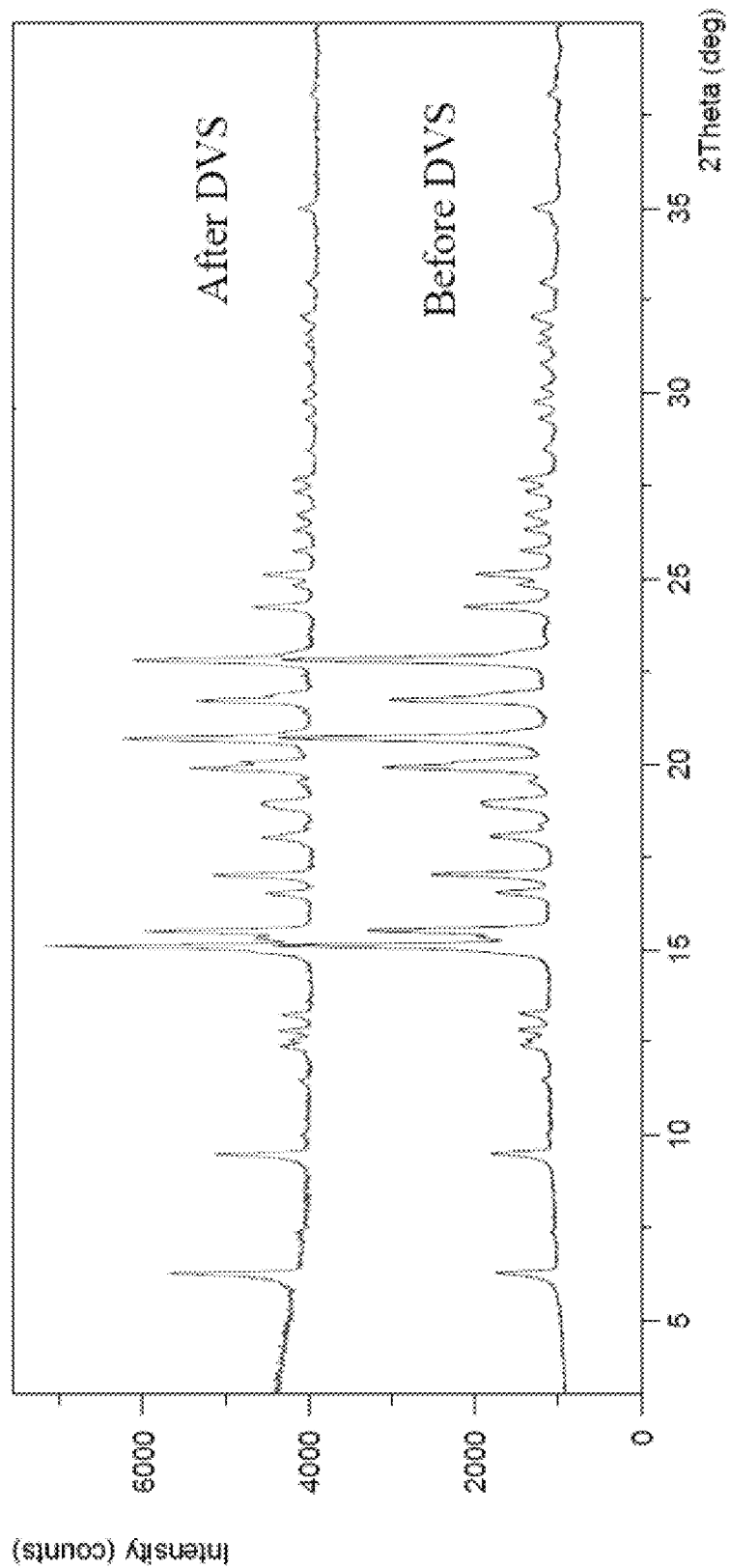
FIG. 4F shows XRPD patterns of Form B pre and post DVS.
Figure 4G:
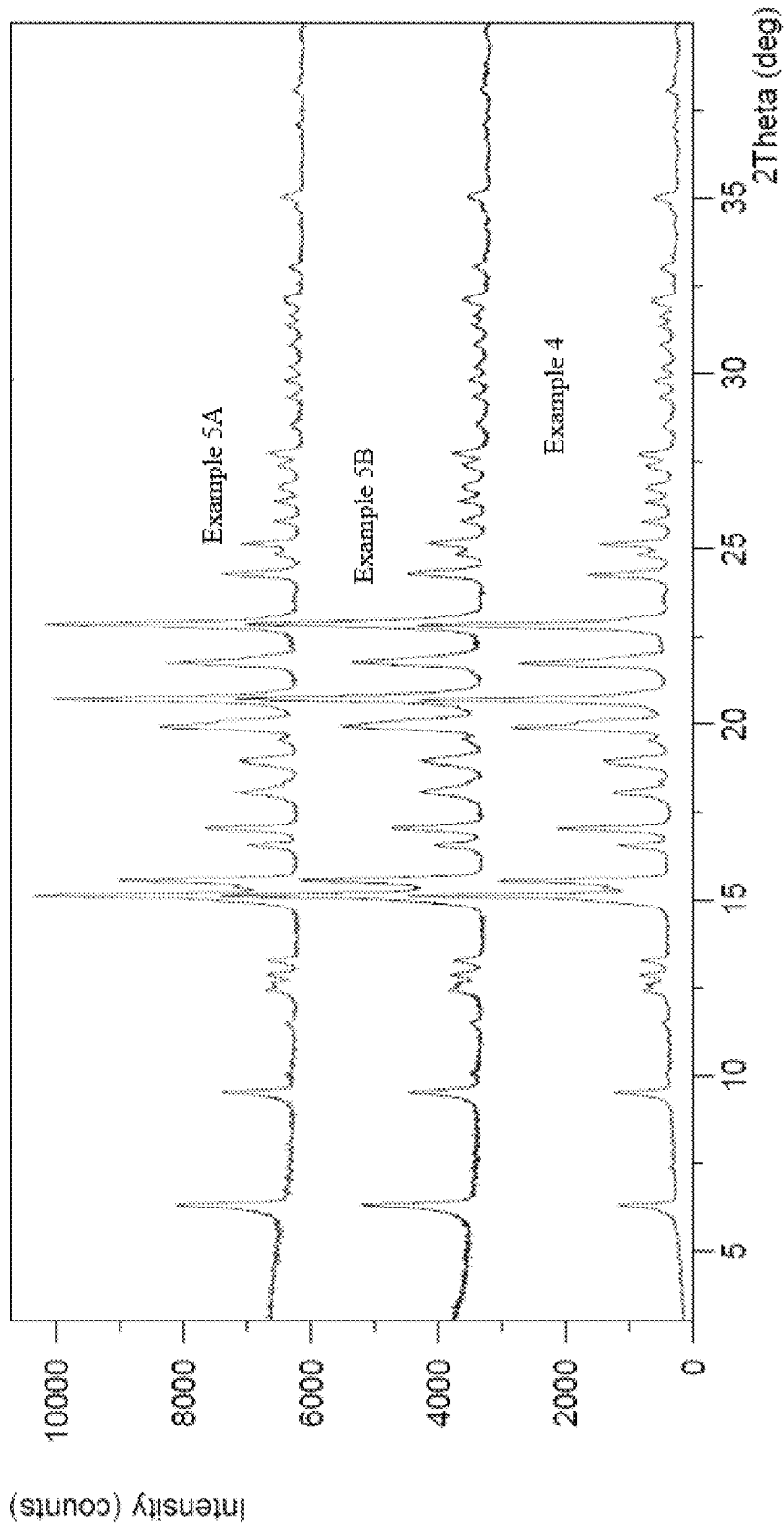
FIG. 4G shows XRPD overlay of Form B of Example 4, Example 5A and Example 5B.

Compound 1 in Form B prepared in Example 4 was subjected to hygroscopic test using dynamic vapor sorption (DVS). The DVS plots is shown in FIG. 4E suggesting Form B is non-hygroscopic. After the DVS test, no form change was observed by XRPD comparison as shown in FIG. 4F.

The long term stability studies of Compound 1 in Form B showed there was no significant chemical purity change occurred when stored at 25° C./60% RH for up to 12 months and at 40° C./75% RH condition for up to 6 months. In addition, no crystal form and optical purity changes were observed when stored at 25° C./60% RH for up to 12 months and at 40° C./75% RH condition for up to 6 months.

Example 8: Mechanical Test

Grinding experiments were conducted in two conditions with water and without any solvent. About 15 mg of Compound 1 in Form A prepared in Example 2 was added into the mortar and manually ground with/without solvents for 5 minutes before the solids were collected and analyzed. As summarized in Table 7, amorphous was obtained by XRPD characterization.

TABLE 7

Summary of grinding experiments

| No. | Solvent | Solid Form |
|---|---|---|
| 1 | N/A | amorphous |
| 2 | H$_2$O | amorphous |

N/A: no solvent was added.

Figure 4H:
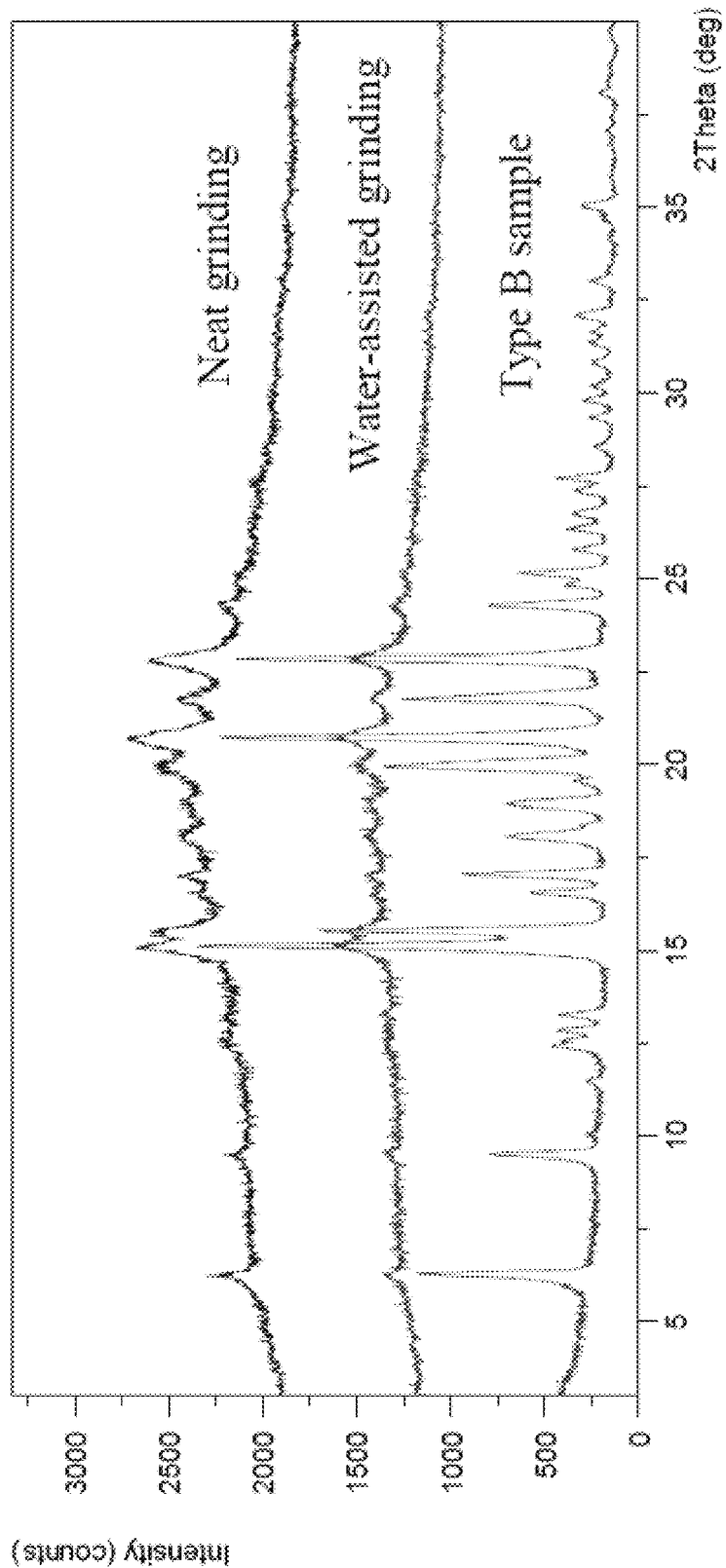
FIG. 4H shows XRPD overlay of Form B before and after grinding.

Grinding experiments were also conducted with respect to Form B of Example 4 to evaluate possible form change of Form B under mechanical force. Neat and water-assisted grinding experiments were performed with respect to Form B. About 15 mg of Compound 1 in Form B prepared in Example 4 was added into the mortar and manually ground with/without water for 5 minutes. Then solids were collected for XRPD characterization. FIG. 4H showed that mechanical strain did not change Form B to become amorphous or other forms, although crystallinity has been decreased after grinding. The result further confirmed Form B is more stable then Form A.

Example 9

Determination of Absolute Configuration of Compound 1
    Preparation of BG-13 Single Crystal
    Six single crystal growth experiments (see Table 8) were performed via slow cooling. Suitable single crystals of BG-13 were obtained by slow cooling in MeOH/H$_2$O (1:1, v/v).

TABLE 8

Single Crystal Growth Experiments

| Experiment ID | Weight (mg) | Solvent (1 mL, v/v) | Method | Temperature (° C.) | Dissolved (Y/N*) | Observation |
|---|---|---|---|---|---|---|
| 1 | 5.6 | IPA/H$_2$O (3/1) | cooling | 60 | N | Block-like crystal |
| 2 | 5.5 | IPA/H$_2$O (3/1) | cooling | 60 | N | Block -like crystal |
| 3 | 5.4 | IPA/H$_2$O (3/1) | cooling | 60 | N | Block -like crystal |
| 4 | 5.5 | IPA/H$_2$O (3/1) | cooling | 60 | N | Block -like crystal |
| 5 | 4.7 | MeOH/H$_2$O (2/1) | cooling | 60 | N | Crystal |
| 6 | 5.5 | MeOH/H$_2$O (1/1) | cooling | 60 | N | Crystal |

The single crystal data and structure refinement data were generated as shown in Table 9 on a Bruker APEX DUO single-crystal diffractometer with CCD detector (Cu Kα, λ=1.54178 Å, 173.15 K).

TABLE 9

Single Crystal Data and Structure Refinement of BG-13

| | | |
|---|---|---|
| Empirical formula | C$_{33}$H$_{34}$N$_5$O$_6$ | — |
| Formula weight | 596.65 | — |
| Temperature | 173.15 | — |
| Wavelength | 1.54178 Å | — |
| Crystal system, space group | monoclinic | C2 |
| Unit cell dimensions | a = 16.7939(4) Å | alpha = 99.00 deg.. |
| | b = 7.9871(2) Å | beta = 108.0460(10) deg. |
| | c = 23.5438(5) Å | gamma = 90.00 deg. |
| Volume | 3002.69(12) Å$^3$ | — |
| Z, Calculated density | 4 | 1.320 mg/mm$^3$ |
| Absorption coefficient | 0.756 mm$^{-1}$ | — |
| F(000) | 1260.0 | — |
| Crystal size | 0.3 × 0.21 × 0.08 mm$^3$ | — |
| Theta range for data collection | 1.97 to 64.96 deg. | — |
| Limiting indices | −19 <= h <= 1, | |
| | −7 <= k <= 9, | |
| | −27 <= l <= 24 | |
| Reflections collected/unique | 5073/3756 | — |
| | [R(int) = 0.1062] | |
| Completeness | 92.8% | — |
| Refinement method | Full matrix least squares on F$^2$ | — |
| Data/restraints/parameters | 3756/1/398 | — |
| Goodness-of-fit on F$^2$ | 1.192 | — |
| Final R indices [I > 2sigma(I)] | R$_1$ = 0.0819 | wR$_2$ = 8.2294 |
| Absolute structure Flack | 0.0(3) | — |
| Largest diff. peak and hole | 0.50 and −0.57 e · A$^{-3}$ | — |

Figure 6A:
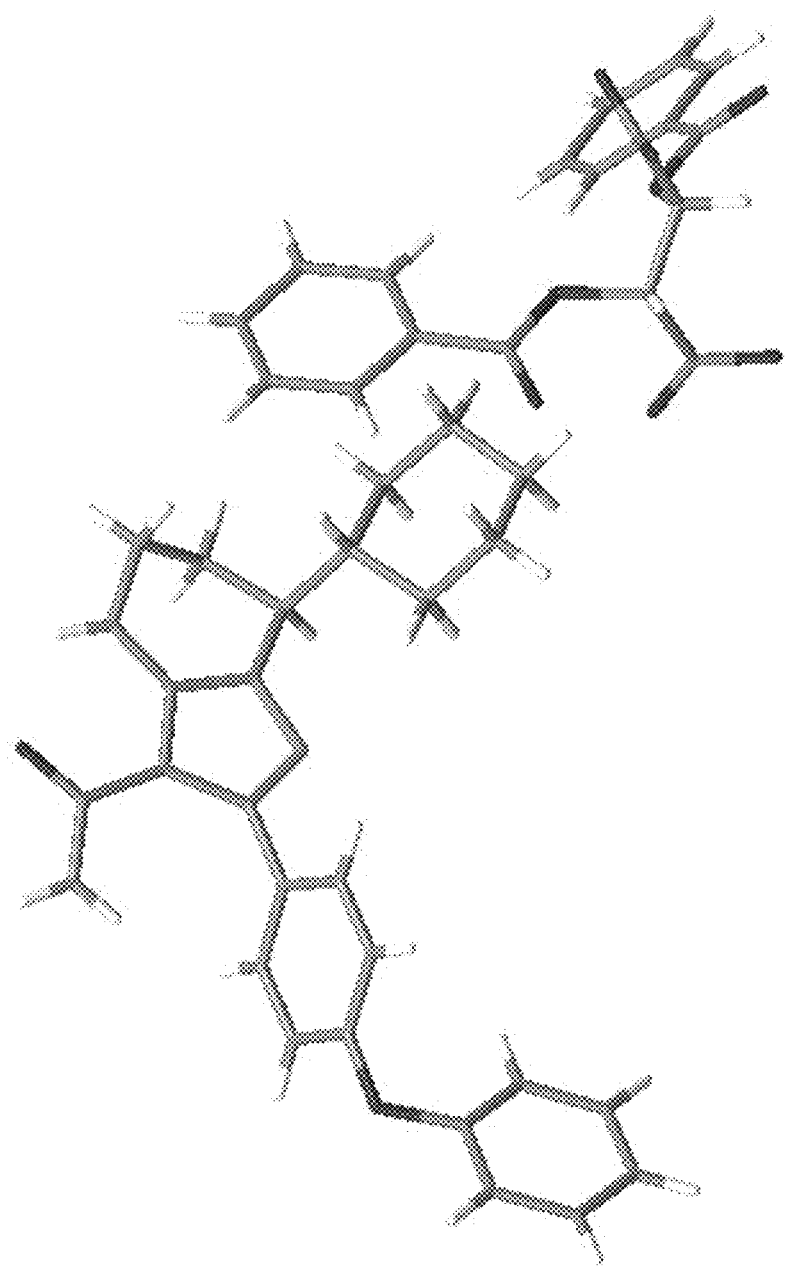
FIG. 6A shows the absolute structure of single crystal of BG-13.
Figure 6B:
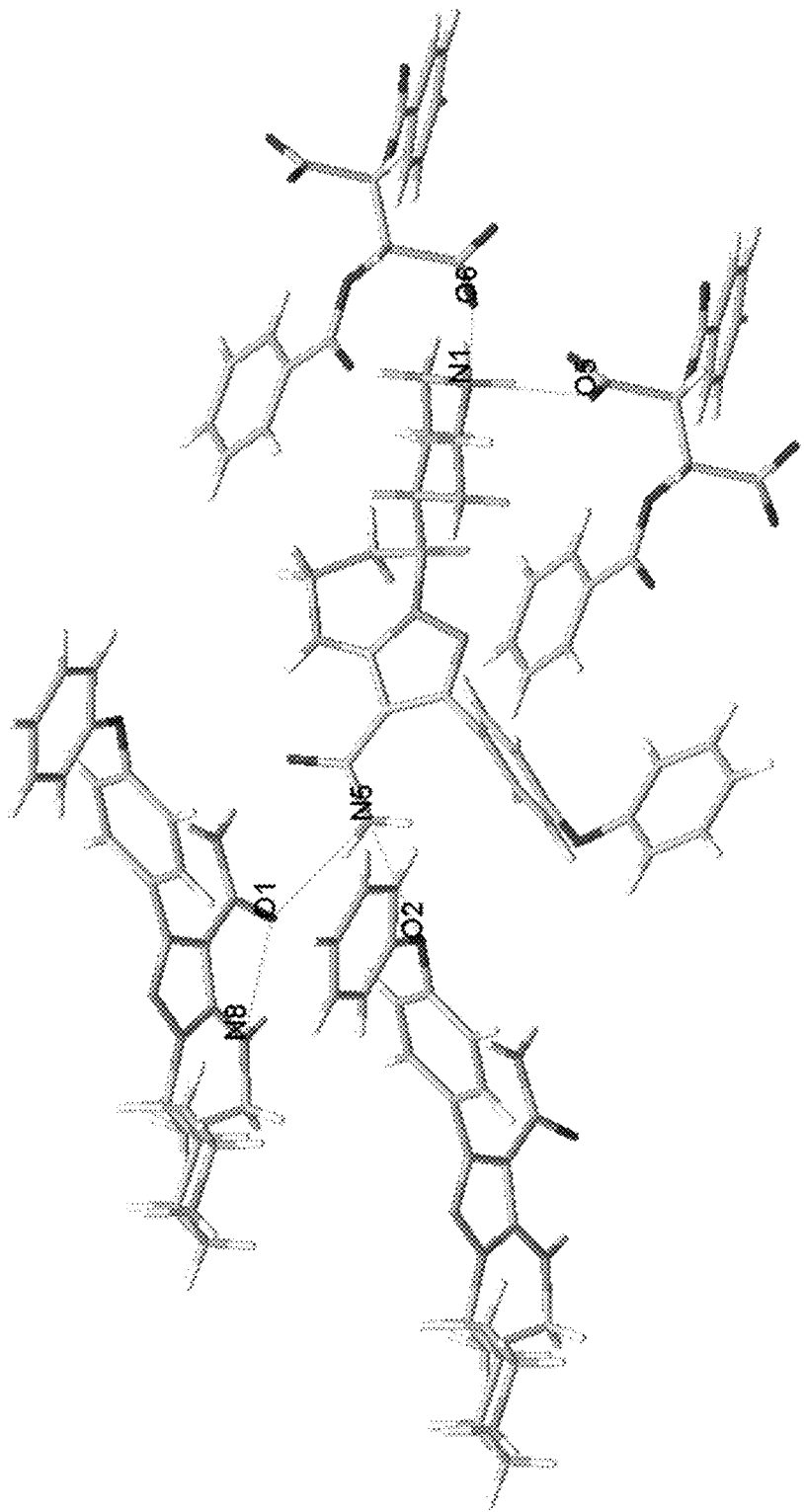
FIG. 6B illustrates hydrogen bonds of single crystal of BG-13.
Figure 6C:
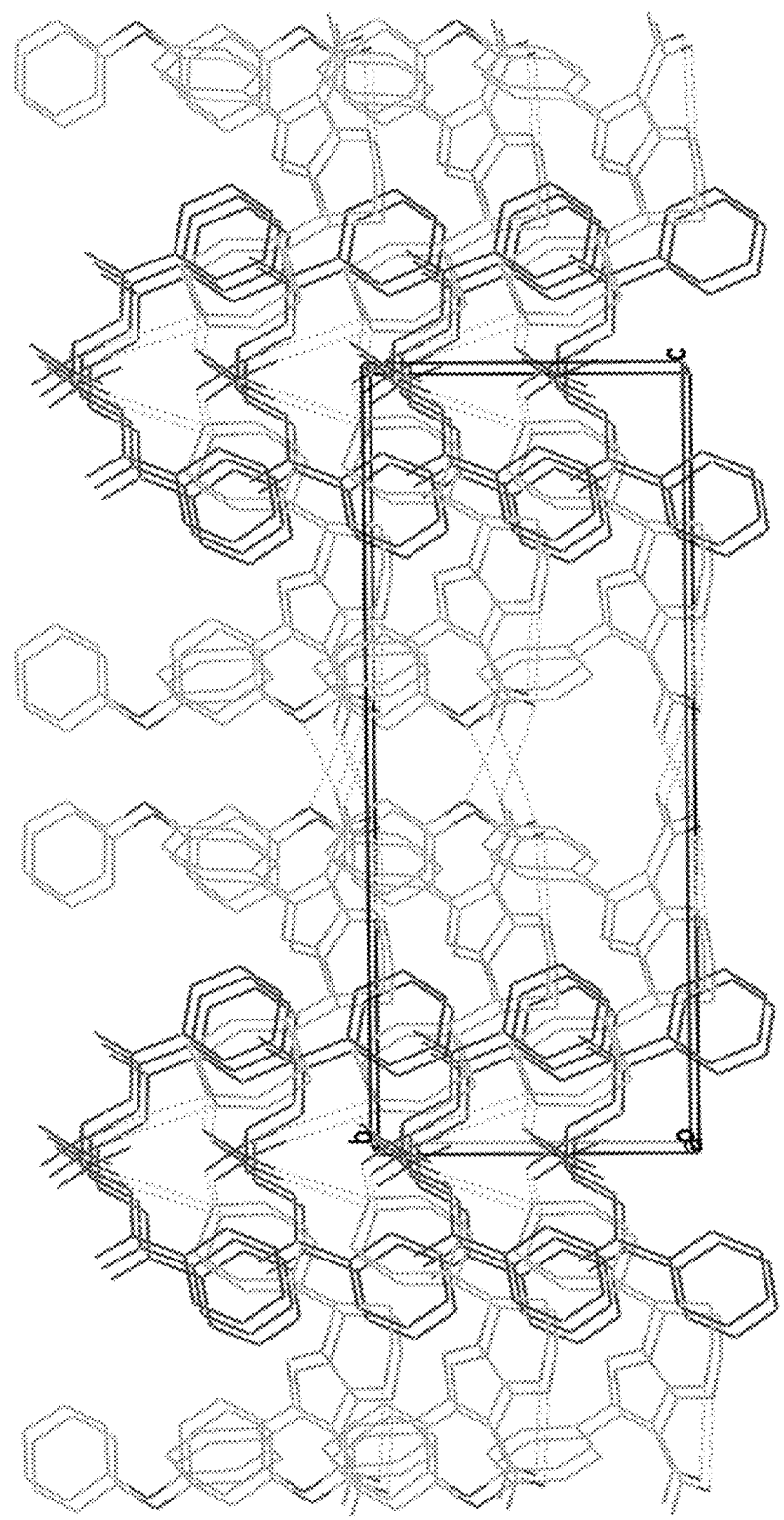
FIG. 6C shows a crystal packing of single crystal of BG-13.
Figure 6D:
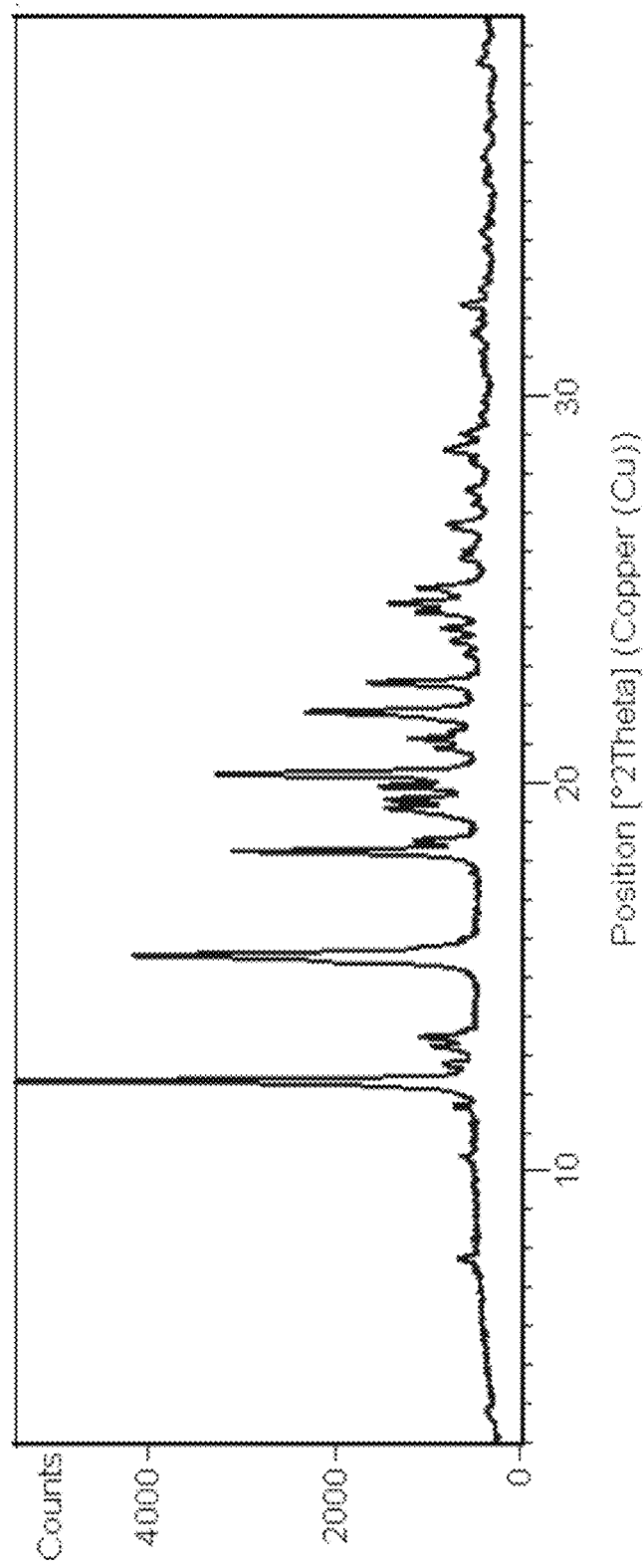
FIG. 6D shows the XRPD pattern of single crystal of BG-13.

BG-13 was confirmed to be a (2R, 3R)-dibenzoyl tartaric acid (L-DBTA) salt and the molar ratio of freebase to L-DBTA is 2:1. Configuration of both carbons (C32 and C32') in L-DBTA was confirmed to be R. Configuration of C6 in freebase was determined to be S, as shown in FIG. 6A to FIG. 6C. A powder X-ray diffraction pattern method was also used to characterize the structure of the single crystals, as shown in FIG. 6D.

Absolute Configuration of Compound 1

The absolute configurations of Compound 1 was deduced to be S from the single crystal X-ray structural analysis of intermediate BG-13.

EFFICACY TESTS (1) BTK Kinase Enzymatic Assay

Form B of Compound 1 was tested for inhibition of BTK kinase (aa2-659, Carna Biosciences) in assays based on the time-resolved fluorescence-resonance energy transfer (TR-FRET) methodology. The assays were carried out in 384-well low volume black plates in a reaction mixture containing BTK kinase, 5 µM ATP, 2 µM peptide substrate and 0-10 µM Form B of Compound 1 of Example 4 in buffer containing 50 mM Tris pH7.4, 10 mM MgCl2, 2 mM MnCl$_2$, 0.1 mM EDTA, 1 mM DTT, 0.005% Tween-20, 20 nM SEB and 0.01% BSA. The kinase was incubated with compound for 60 minutes at room temperature and the reaction was initiated by the addition of ATP and peptide substrate. After reaction at room temperature for 60 minutes, an equal volume of stop/detection solution was added according to the manufacture's instruction (CisBio Bioassays). The stop/detection solution contained Eu$^{3+}$ cryptate-conjugated mouse monoclonal antibody (PT66) anti-phosphotyrosine and XL665-conjugated streptavidin in buffer containing 50 mM HEPES pH 7.0, 800 mM KF, 20 mM EDTA, and 0.1% BSA. Plates were sealed and incubated at room temperature for 1 hour, and the TR-FRET signals (ratio of fluorescence emission at 665 nm over emission at 620 nm with excitation at 337 nm wavelength) were recorded on a PHERAstar FS plate reader (BMG Labtech). Phosphorylation of peptide substrate led to the binding of anti-phosphotyrosine antibody to the biotinylated peptide substrate, which places fluorescent donor (Eu$^{3+}$ crypate) in close proximity to the accepter (Streptavidin-XL665), thus resulting in a high degree of fluorescence resonance energy transfer from the donor fluorophore (at 620 nm) to the acceptor fluorophore (at 665 nm). Inhibition of BTK kinase activity resulted in decrease of the TR-FRET signal. The IC$_{50}$ for Compound 1 in Form B was derived from fitting the data to the four-parameter logistic equation by Graphpad Prism software.

The IC50 of Compound 1 in Form B is 1 nM.

(2) Biochemical Kinase Selectivity

Selectivity of Form B was profiled against a panel of 367 kinases at 2 µM at Reaction Biology Corp. Form B displayed less than 70% inhibition against 358 kinases, and greater than 70% inhibition against 9 kinases including BTK.

The invention claimed is:

1. Crystalline Form A of Compound 1:

Compound 1

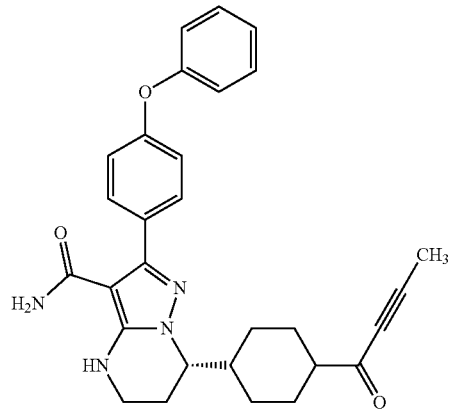

wherein the crystalline form is an ethyl acetate solvate; and
wherein the crystalline form is characterized by an X-ray powder diffraction pattern comprising diffraction peaks having angle values (° 2θ) at 18.6°±0.2° 2θ, 19.8°±0.2° 2θ, and 20.6°±0.2° 2θ.

2. The crystalline form of claim 1, wherein the crystalline form is further characterized by an X-ray powder diffraction pattern comprising additional diffraction peaks having angle values (° 2θ) at 5.3°±0.2° 2θ and 16.90±0.2° 2θ.

3. The crystalline form of claim 1, wherein the crystalline form is further characterized by an X-ray powder diffraction pattern comprising additional diffraction peaks having angle values (° 2θ) at 5.3°±0.2° 2θ, 10.9°±0.2° 2θ, 16.9°±0.2° 2θ, 21.1°±0.2° 2θ, 22.5°±0.2° 2θ, and 22.8°±0.2° 2θ.

4. The crystalline form of claim 1, wherein the crystalline form is further characterized by an X-ray powder diffraction pattern comprising additional diffraction peaks having angle values (° 2θ) at 5.3°±0.2° 2θ, 10.9°±0.2° 2θ, 11.2°±0.2° 2θ, 13.4°±0.2° 2θ, 14.4°±0.2° 2θ, 16.9°±0.2° 2θ, 21.1°±0.2° 2θ, 21.7°±0.2° 2θ, 22.5°±0.2° 2θ, 22.8°±0.2° 2θ, 23.6°±0.2° 2θ, and 24.3°±0.2° 2θ.

5. The crystalline form of claim 1, wherein the crystalline form is further characterized by a differential scanning calorimetry curve in accordance with FIG. 2B.

6. The crystalline form of claim 1, wherein the crystalline form is further characterized by a thermogravimetric analysis curve in accordance with FIG. 2B.

7. A process for preparing crystalline Form A of Compound 1 of claim 1:

Compound 1

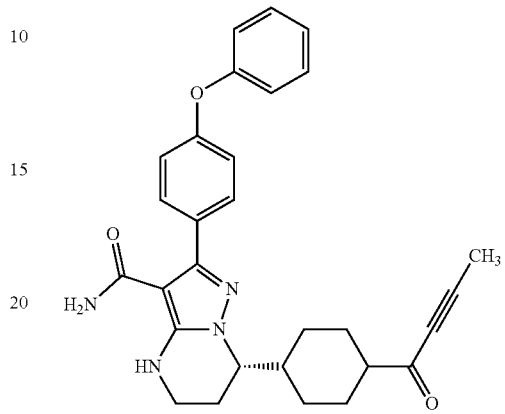

wherein the crystalline form is an ethyl acetate solvate;
wherein the crystalline form is characterized by an X-ray powder diffraction pattern comprising diffraction peaks having angle values (° 2θ) at 18.6°±0.2° 2θ, 19.8°±0.2° 2θ, and 20.6°±0.2° 2θ; and
wherein the process comprises the following steps:
(a) dissolving an amorphous form of Compound 1 in a solvent selected from the group consisting of acetic acid, acetone, acetonitrile, chloroform, dichloromethane, N,N-dimethylacetamide, dimethylsulfoxide, 1,4-dioxane, ethanol, ethyl acetate, isopropanol, isopropyl acetate, methanol, methyl isobutyl ketone, 1-methyl-2-pyrrolidone, tetrahydrofuran, 2-methyltetrahydrofuran, and toluene, or a mixture thereof;
(b) adding an anti-solvent selected from the group consisting of cyclohexane, n-heptane, n-hexane, methyl tert-butyl ether, petroleum ether, and water, or a mixture thereof, to the solution provided in step (a), to induce precipitation; and
(c) maintaining the mixture provided in step (b) at a temperature below 25° C. or at a temperature of 25° C., to precipitate the crystalline Form A of Compound 1 of claim 1.

* * * * *

UNITED STATES PATENT AND TRADEMARK OFFICE
CERTIFICATE OF CORRECTION

| | |
|---|---|
| PATENT NO. | : 11,555,038 B2 |
| APPLICATION NO. | : 16/479709 |
| DATED | : January 17, 2023 |
| INVENTOR(S) | : Guo et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 567 days.

Signed and Sealed this
Seventeenth Day of September, 2024

Katherine Kelly Vidal
*Director of the United States Patent and Trademark Office*